(12) United States Patent
Mayers et al.

(10) Patent No.: US 7,807,136 B2
(45) Date of Patent: **\*Oct. 5, 2010**

(54) METHOD AND COMPOSITION FOR THE TREATMENT OF CANCER BY THE ENZYMATIC CONVERSION OF SOLUBLE RADIOACTIVE TOXIC PRECIPITATES IN THE CANCER

(75) Inventors: George L. Mayers, Gainesville, FL (US); Samuel Rose, Emeryville, CA (US); Lottie Rose, legal representative, Emeryville, CA (US)

(73) Assignee: David S. Rose, Emeryville, CA (US)

( * ) Notice: Subject to any disclaimer, the term of this patent is extended or adjusted under 35 U.S.C. 154(b) by 1478 days.

This patent is subject to a terminal disclaimer.

(21) Appl. No.: 10/898,585

(22) Filed: Jul. 23, 2004

(65) Prior Publication Data

US 2005/0058652 A1    Mar. 17, 2005
US 2010/0062006 A9    Mar. 11, 2010

Related U.S. Application Data

(60) Continuation-in-part of application No. 10/226,288, filed on Aug. 22, 2002, now abandoned, which is a division of application No. 09/314,422, filed on May 18, 1999, now Pat. No. 6,468,503, which is a division of application No. 08/782,219, filed on Jan. 13, 1997, now Pat. No. 6,080,383.

(51) Int. Cl.
    *A61K 49/00* (2006.01)
(52) U.S. Cl. .................................................... 424/9.1
(58) Field of Classification Search .................. None
    See application file for complete search history.

(56) References Cited

U.S. PATENT DOCUMENTS 5,578,287 A  *  11/1996  Theodore et al. ........... 424/1.49
6,080,383 A  *   6/2000  Rose ......................... 424/1.69

OTHER PUBLICATIONS

Rose (J. Theor. Biol. 1998; 195: 111-128).*

* cited by examiner

*Primary Examiner*—Brandon J Fetterolf
(74) *Attorney, Agent, or Firm*—Mintz Levin Cohn Ferris Glovsky and Popeo, P.C.; Cynthia A. Kozakiewicz

(57) ABSTRACT

The invention features compositions and methods for treating or alleviating a symptom of cancer. The compositions and methods of the invention direct supra-lethal doses of radiation, called Hot-Spots, to virtually all cancer cell types.

2 Claims, 52 Drawing Sheets

Time

*Formation of the hydrazone anchoring the Step 3 Bispecific Reagent to the Nano-platform*

*Formation of the thioether anchoring the Step 3 Bispecific Reagent to the Nano-platform*

FIG. 29
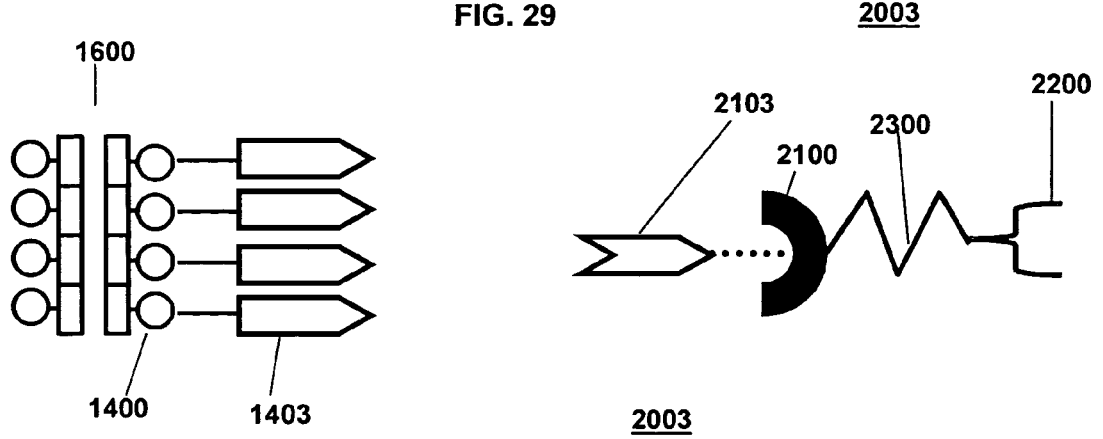
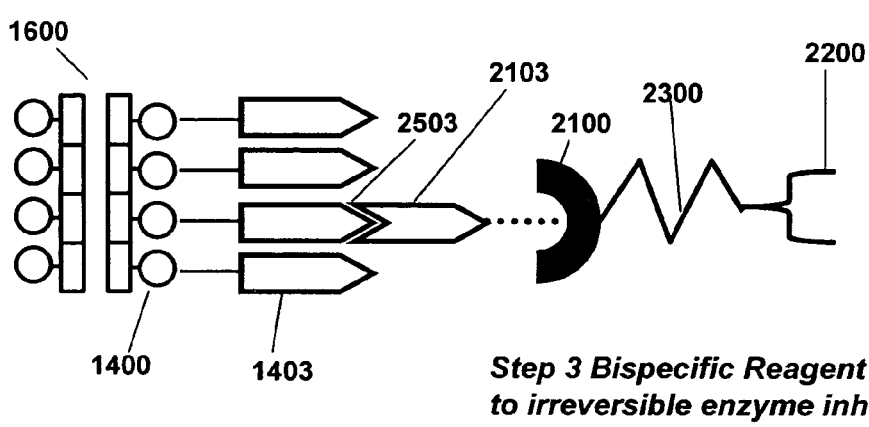
*Step 3 Bispecific Reagent covalently bound to irreversible enzyme inhibitor*

*Step 3 Bispecific Reagent bound to Nano Platform via a specific antibody*

FIG. 35: Synthesis of the Step 3 Bispecific Reagent composed of UDP-N-acetylglucosamine enolpyruvoyl transferase and Streptavidin FIG. 36: Preparation of plasmid for the β-lactamase mutants.

FIG. 37: Preparation of the plasmid for the Step 3 bispecific reagent, mutant β-lactamase—β-D-galactosidase.

FIG. 38: Preparation of Step 3 Bispecific Reagent, Ornithine decarboxylase with aldehyde sidechains FIG. 39: Preparation of Step 3 Bispecific Reagent, mutant β-lactamase-anti-NIP monoclonal antibody FIG. 40: Preparation of Step 3 Bispecific Reagent, mutant β-lactamase-alkaline phosphatase FIG. 42: Preparation of 90Y-Biotin-pentyl-DOTA to be used as a Step 4 Reagent

FIG. 43
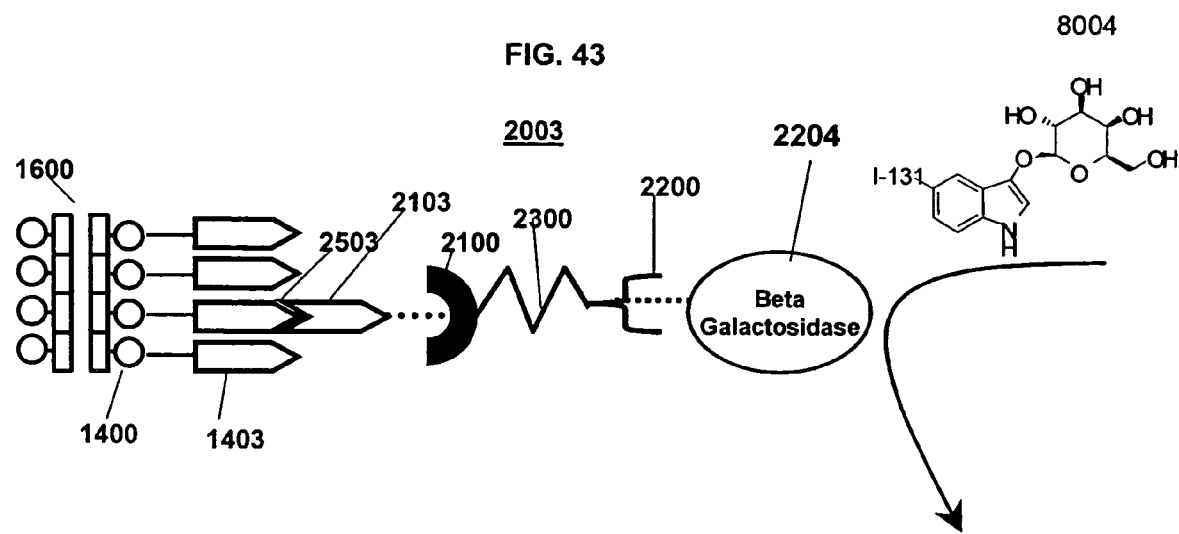
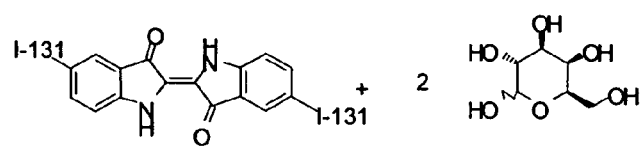

FIG. 44: Preparation of 3-($^{131}$I-5-Iodoindoxyl)galactoside to be used as a Step 4 Reagent FIG. 46: Preparation of $^{131}$I-p-iodobenzoic hydrazide to be used as a Step 4 Reagent FIG. 48: Preparation of $^{131}$I-4-Hydroxyl-3-iodo-5-nitrophenylacetic acid (NIP acid) to be used as a Step 4 Reagent

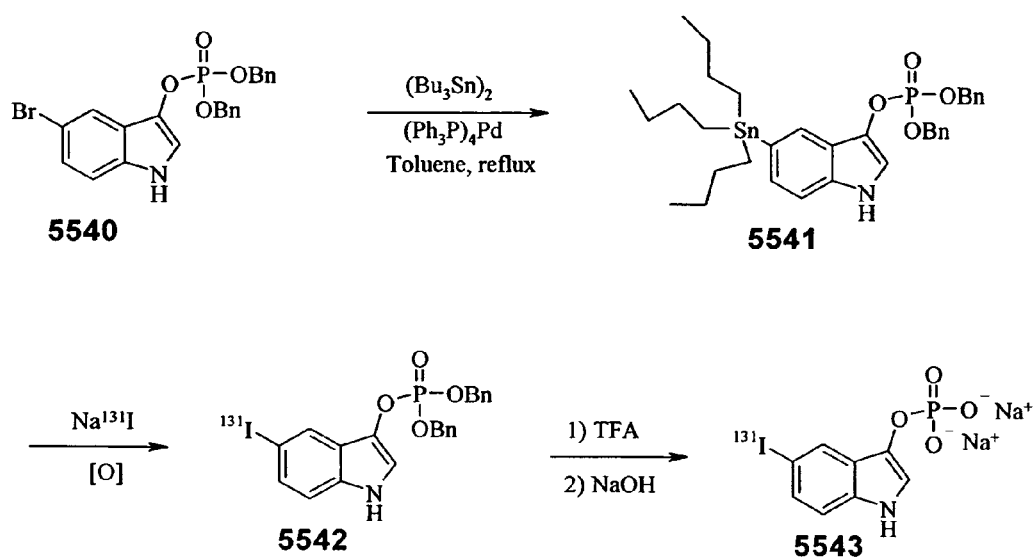
FIG. 50: Preparation of $^{131}$I-5-Iodoindoxylphosphate to be used as a Step 4 Reagent

US 7,807,136 B2

METHOD AND COMPOSITION FOR THE TREATMENT OF CANCER BY THE ENZYMATIC CONVERSION OF SOLUBLE RADIOACTIVE TOXIC PRECIPITATES IN THE CANCER

RELATED APPLICATIONS

This application is a Continuation-in-Part of U.S. Ser. No. 10/226,288, filed Aug. 22, 2002 which is a divisional of U.S. Ser. No. 09/314,422, filed May 18, 1999, now U.S. Pat. No. 6,468,503 issued on Oct. 22, 2002, which is a divisional of U.S. Ser. No. 08/782,219, filed Jan. 13, 1997, now U.S. Pat. No. 6,080,383, issued on Jun. 27, 2000.

FIELD OF THE INVENTION

The invention relates to the treatment of cancer.

BACKGROUND OF THE INVENTION

A considerable portion of worldwide research efforts in the treatment of cancer is currently devoted to killing cancer cells by means of various cell-killing agents. Despite the fact that numerous drugs, including radioactive compounds, have been shown to be capable of killing cancer cells, these agents frequently fail to treat cancer successfully because of their inability to circumvent three universally present obstacles: (1) the agents do not kill all the cancer cells because they do not exhibit cytotoxic specificity for all the cancer cells, (2) the agents also kill normal cells because they do not exhibit cytotoxic specificity exclusively for cancer cells, and (3) the agents are not potent enough at tolerable doses to kill resistant cancer cells or to overcome the ability of cancer cells to adapt and become resistant to the cell-killing agents.

SUMMARY OF INVENTION

The invention provides compositions and methods for treating cancer. The methods of the invention are a multi-step therapy process that directs localized supra-lethal doses of radiation called Hot-Spots to virtually any cancer.

In one aspect the invention provides a Step 1 Reagent containing a cell targeting agent linked, e.g., covalently to a platform building material. The platform building material detaches from the cell targeting agent upon uptake of the reagent into a cell, e.g., a cancer cell. The platform building material once detached from the cell targeting agent becomes aqueous insoluble, forming a nano-platform. Optionally, the cell targeting agent is linked to the platform building material by a carrier moiety. In various aspects of the invention, the platform building material has an additional molecular structure that is capable of specifically binding a second reagent, i.e., a Step 3 Reagent.

A cell targeting agent augments cellular uptake of the reagent and is a polypeptide, a cell surface ligand, a peptide, or a small molecule. A polypeptide is, for example, an antibody such as an EGF receptor antibody or a transferrin receptor antibody, epidermal growth factor or a viral protein such as a human immunodeficiency virus (HIV) 1 TAT protein, a functionally effective portion of (HIV) 1 TAT protein, or VP22. A cell surface ligand is for example transferrin, epidermal growth factor or an interleukin.

A peptide is, for example, a peptide hormone such as oxytocin, growth hormone releasing hormone, glucagon, gastrin, secretin, somatostatin, prolactin, follicle stimulating hormone, insulin, growth hormone, or an arginine-glycine-aspartic acid peptide (RGD).

A small molecule is, for example, a hormone such as estrogen, calciferol, or testosterone, a nucleic acid, a peptidomimetic, a carbohydrate, a lipid, a nicotinic acetylcholine receptor agonist or folic acid or analogue or derivative thereof.

The platform building material is, for example, an indoxyl, a porphyrin, a polymer such as a HPMA derivative, a dendrimer, an opio-melanin or a polysaccharide such as dextran, gum Arabic, cellulose or chitin. The indoxyl is, for example, a substituted indoxyl, i.e., a mono-indoxyl, a bis-indoxyl or a poly indoxyl. The indoxyl forms indigo, a linear indigo polymer or a polyindigo lattice.

A carrier moiety is, for example, a protein; a polysaccharide; a polymer, e.g., synthetic polymer or a biopolymer such as polylysine; a dendrimer; a liposome; a nanoparticle; or a polymeric micelle.

Exemplary Step 1 Reagents include the following: An anti-EGF receptor antibody, derivative or fragment thereof linked to a substituted 3-indoxyl phosphate derivative. The antibody is linked to the 3-indoxyl phosphate derivative by a carrier moiety such as dextran. Additionally, a UDP-N-acetylglucosamine enolpyruvoyltransferase inhibitor such as a phosphoenol pyruvate derivative is linked to the 3-indoxyl phosphate derivative.

A transferrin polypeptide or fragment thereof linked to a glycoside, e.g., a galactoside, a glucoside or a glucuronide or derivative thereof. Preferably, the glycoside is a substituted bis-3-indoxyl glycoside derivative. The transferrin polypeptide is linked to the glycoside by a carrier moiety such as an albumin polypeptide or fragment thereof. Additionally, a mutant β-lactamase inhibitor is linked to the bis-3-indoxyl glycoside derivative. The mutant β-lactamase inhibitor is a lactam derivative such as a carbacephem analog. A carbacephem analog is, for example, Loracarbef.

A folate derivative linked to a porphyrin derivative. The folate derivative is linked to the porphyrin derivative by a carrier moiety such as an immunoglobulin polypeptide or fragment thereof. Additionally, an ornithine decarboxylase inhibitor, e.g., an α-difluoromethylornithine or an arginine decarboxylase inhibitor, e.g., an α-difluoromethylarginine is linked to the porphyrin derivative.

A folate derivative linked to a substituted bis-3-indoxyl galactoside derivative. Additionally, a mutant β-lactamase inhibitor is linked to the substituted bis-3-indoxyl galactoside derivative.

An epidermal growth factor polypeptide or fragment thereof linked to HPMA. Additionally, a substituted indoxyl galactoside derivative and a mutant β-lactamase inhibitor are linked to the HPMA.

Another aspect of the invention provides a Step 3 Reagent that is a bi-specific reagent containing a targeting moiety and an isotope trapping moiety. The targeting moiety and the isotope trapping moiety are linked, e.g., covalently. The targeting moiety is capable of binding the nano-platform. For example, the targeting moiety binds to the additional molecular structures on the nano-platform. The isotope trapping moiety is capable of trapping a radio-labeled aqueous soluble Step 4 Reagent.

The targeting moiety or the isotope trapping moiety is an organic functional group such as a hydrazide, a ketone, a mercaptan, or a maleimidyl; a polypeptide; a peptide; or a lectin. The polypeptide is an enzyme such as a β-lactamase, an arginine decarboxylase, an ornithine decarboxylase, a chloramphenicol acetyltransferase, or a UDP-N-acetylglucosamine enolpyruvoyltransferase; a mutant enzyme such as a mutant β-lactamase; or an antibody or a fragment thereof.

Exemplary Step 3 Reagents include the following: A UDP-N-acetylglucosamine enolpyruvoyltransferase linked to Streptavidin. A mutant β-lactamase linked to a β-D-galactosidase. An ornithine decarboxylase or an arginine decarboxylase linked to 4-carboxybenzaldehyde. A mutant β-lactamase linked to an anti-NIP antibody. A mutant β-lactamase linked to an alkaline phosphatase.

Another aspect of the invention provides a kit packaged in one or more containers containing a Step 1 Reagent and a Step 3 Reagent. Optionally, the kit contains a Step 2 cell-killing Reagent and/or a radiolabeled aqueous soluble Step 4 Reagent. Exemplary Step 4 Reagents include, $^{90}$Y-biotin-pentyl-DOTA, $^{131}$I-5-iodo-3-indoxyl galactoside, $^{131}$I-p-iodobenzoic hydrazide, $^{131}$I-4-hydroxy-3-iodo-5-nitrophenylacetic acid and $^{131}$I-5-iodo-3-indoxyl phosphate.

Cancer is treated or a symptom of cancer is alleviated, by administering to the subject (a) a Step 1 Reagent containing a cell targeting agent linked, e.g., covalently to a platform building material; (b) a Step 3 Reagent containing a targeting moiety and an isotope trapping moiety; and (c) a radiolabeled aqueous soluble Step 4 Reagent. The cell targeting agent augments cellular uptake of the Step 1 Reagent. The platform building material detaches from the cell targeting agent upon uptake of the Step 1 Reagent into the cell and forms an aqueous insoluble nano-platform to which the targeting moiety of the Step 3 Reagent binds. The isotope trapping moiety of the Step 3 Reagent traps the radiolabeled aqueous soluble Step 4 Reagent within the tumor extracellular matrix for the required period of time to create micro-regional radiation fields (Hot Spots) to deliver lethal irradiation to the surrounding tumor cells.

The reagents are administered sequentially. Alternatively, the reagents are administered concurrently. Optionally, a Step 2 cell-killing Reagent is administered to the subject prior to, after or concurrently with the Step 3 Reagent to relocate the nano-platform into the tumor extracellular matrix.

In one aspect, a cancer is treated or a symptom of cancer is alleviated, by administering to the subject (a) a composition containing an anti-EGF receptor antibody, derivative or fragment thereof linked to a substituted 3-indoxyl phosphate derivative with an UDP-N-acetylglucosamine enolpyruvoyltransferase inhibitor linked to the 3-indoxyl phosphate derivative; (b) a composition containing a UDP-N-acetylglucosamine enolpyruvoyltransferase linked to Streptavidin; and (c) a composition containing $^{90}$Y-biotin-pentyl-DOTA.

In another aspect, a cancer is treated or a symptom of cancer is alleviated, by administering to the subject (a) a composition containing a transferrin polypeptide or fragment thereof linked to a substituted bis-3-indoxyl glycoside derivative with a mutant β-lactamase inhibitor linked to the bis-3-indoxyl glycoside derivative; (b) a composition containing a mutant β-lactamase linked to a β-D-galactosidase; and (c) a composition containing $^{131}$I-5-iodo-3-indoxyl galactoside.

In a further aspect, a cancer is treated or a symptom of cancer is alleviated, by administering to the subject (a) a composition containing a folate derivative linked to a porphyrin derivative with either an ornithine decarboxylase inhibitor or arginine decarboxylase inhibitor linked to the porphyrin derivative; (b) a composition containing an ornithine decarboxylase or arginine decarboxylase linked to 4-carboxybenzaldehyde; and (c) a composition containing $^{131}$I-p-iodobenzoic hydrazide.

In yet another aspect, a cancer is treated or a symptom of cancer is alleviated, by administering to the subject (a) a composition containing a folate derivative linked to a substituted bis-3-indoxyl galactoside derivative with a mutant β-lactamase inhibitor linked to the bis-3-indoxyl galactoside derivative; (b) a composition containing a mutant β-lactamase linked to an anti-NIP antibody; and (c) a composition containing $^{131}$I-4-hydroxy-3-iodo-5-nitrophenylacetic acid ($^{131}$I-NIP acid).

In another aspect, a cancer is treated or a symptom of cancer is alleviated, by administering to the subject (a) a composition containing an epidermal growth factor (EGF) polypeptide or fragment thereof linked to HPMA with a substituted indoxyl galactoside derivative linked to the HPMA and a mutant β-lactamase inhibitor linked to the HPMA; (b) a composition containing a β-lactamase linked to an alkaline phosphatase; and (c) a composition containing $^{131}$I-5-iodo-3-indoxyl phosphate.

The subject is a mammal such as human, a primate, mouse, rat, dog, cat, cow, horse, pig, and ferret. The subject is suffering from cancer. The cancer is for example breast cancer, skin cancer, prostate cancer, lung cancer, colon cancer, liver cancer, cervical cancer, brain cancer, ovarian cancer, pancreatic cancer, or stomach cancer. A subject suffering from cancer is identified by methods known in the art such as physical examination; blood test for specific cancer antigens such as PSA; MRI; x-ray; or mammography. Symptoms of cancer include fatigue; nausea; frequent urination; weight loss; lump or thickening in the breast or testicles; a change in a wart or mole; a skin sore or a persistent sore throat that doesn't heal; a change in bowel or bladder habits; a persistent cough or coughing blood; constant indigestion or trouble swallowing; unusual bleeding or vaginal discharge; flu-like symptoms; bruising; dizziness; drowsiness; abnormal eye movements or changes in vision.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 29 is an illustration depicting the Step 3 Bispecific Reagent covalently bound to irreversible enzyme inhibitor.

FIG. 43 is an illustration depicting the Preparation of second example of a Step 4 Reagent.

FIG. 50 is an illustration depicting the preparation of $^{131}$I-5-Iodo-3-indoxylphosphate to be used as a Step 4 Reagent.

DETAILED DESCRIPTION OF THE INVENTION

The present invention provides compositions and methods for treating a heterogeneous population of cancer cells in a subject by the delivery of local irradiation. The present invention is based in part on the observation of the highly successful treatment of thyroid cancer with radio-iodide. The successful treatment of thyroid cancer is due in part to the fact that many malignant thyroid cells have a unique biological function that allows them to trap iodine. Thus, when a patient with thyroid cancer is treated with radio-iodide, a sufficient fraction of the cancer cells takes up sufficient quantities of the radioisotope and stores the radioisotope long enough to generate overlapping micro-regions of intense radiation (referred to as "Hot-Spots") in which all the cells in each micro-region are killed. The radiation field in each of these Hot-Spots extends beyond the cells that take up the radioisotope and kills thousands of neighboring cells. Inside these Hot-Spots, the radiation is so intense that all of the cancer cells in the Hot-Spots are killed, including the cells that do not take up the radioisotope, allowing eradication of the entire tumor. No other tissue or group of cells in the body has this same iodine trapping mechanism, thus Hot-Spots are generated exclusively in the normal and malignant thyroid tissue. The method and compositions of the present invention reproduces these radioisotope delivery and trapping conditions for non-thyroid cancers. The generation of "Hot-Spots" in non-thyroid cancers is a multi-step process that generates overlapping Hot- Spots virtually exclusively in the tumors without causing significant systemic toxicity. All cancer cells within these overlapping Hot-Spots are eradicated. The eradicated cells include cancer cells that are not targeted, cancer cells that are resistant and even super-resistant, and cancer cells that would otherwise adapt and become resistant to therapy. Accordingly, the methods of the invention are not defeated by the heterogeneity of cancer cells and the imperfect nature of current cancer targeting agents.

Figure 1:
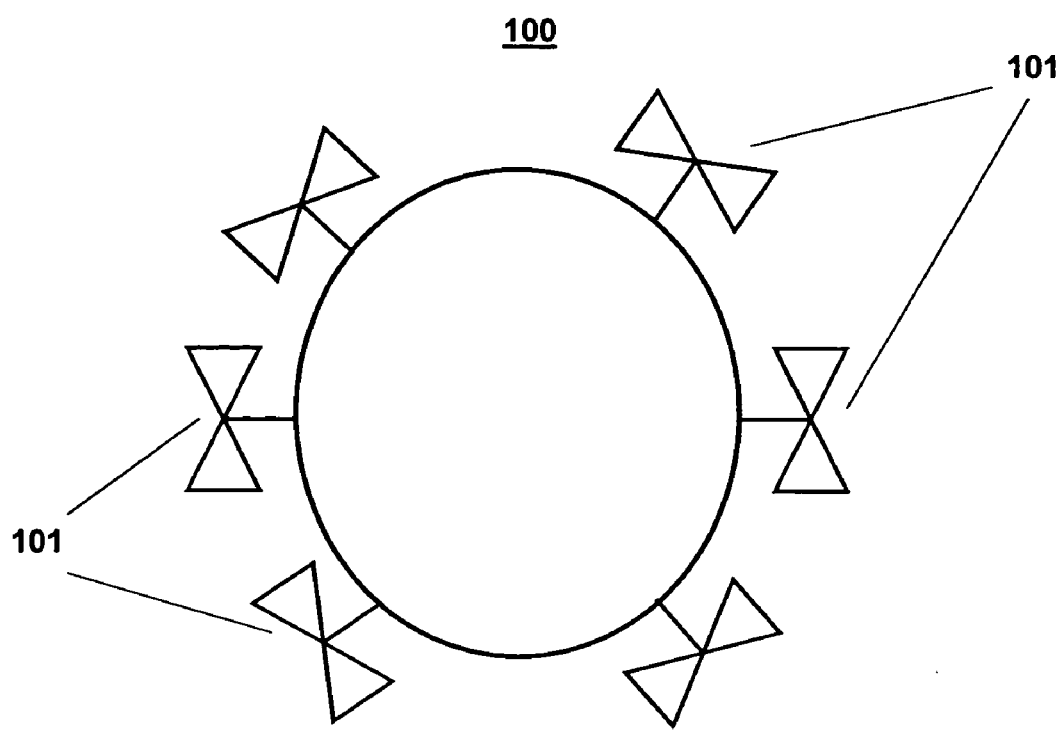
FIG. 1 is an illustration depicting a cancer cell with receptors.

As shown in FIG. 1, cancer contains a population of cancer cells 100 each having internalizing structures 101 which are specific to cancer cells and capable of binding a cell targeting agent. The internalizing structures 101 are capable of internalization when the targeting agent binds to them. Subpopulations of the targeted cancer cells also have a high sensitivity to being killed by the natural system of the subject and/or a high sensitivity to being killed by an administered cell-killing process.

Methods of Treating Cancer

Cancer is treated, or a symptom of cancer is alleviated by administering to a subject multiple reagents in a plurality of steps. All types of cancers are suitable for treatment. Cancers to be treated include for example lung cancer, colon cancer, breast cancer, prostate cancer, liver cancer, pancreatic cancer, bladder cancer, skin cancer (e.g., melanoma), ovarian cancer, cervical cancer, head and neck cancer, hematological cancers, lung cancer, colon/rectal/anal cancer, cervical cancer, brain cancer, ovarian cancer, stomach cancer, kidney cancer, uterine cancer, bone cancer, esophageal cancer, eye cancer, Kaposi's sarcoma, laryngeal cancer, lip cancer, nasopharyngeal cancer, oropharyngeal cancer, oral cavity cancer, testicular cancer, thyroid cancer, sarcomas, lymphomas, adrenocortical cancer, bile duct cancer, bronchial cancer, cancer of unknown primary, gallbladder cancer, germ cell cancer, hypopharyngeal cancer, islet cell cancer, mesothelioma, multiple myeloma, nasal cavity cancer, paranasal sinus cancer, parathyroid cancer, penile cancer, pituitary cancer, salivary gland cancer, small intestine cancer, thymus cancer, ureter cancer, urethral cancer, vaginal cancer, vulvar cancer, and Wilm's tumor.

The subject is a mammal. The mammal is, e.g., a human, non-human primate, mouse, rat, dog, cat, horse, or cow. The steps are administered sequentially. Optionally, one or more steps are administered prior to or concurrently with another. Each step is administered at least once. Alternatively, each step is administered 2, 3, 4, 5, 10, 15 or more times or in a continuous infusion. For example, a Step 2 Reagent is administered in multiple doses using standard therapeutic protocols known in the art. The subject is administered a reagent containing a cell targeting agent which augments cellular uptake of the reagent linked to a platform building material (referred to herein as a Step 1 Reagent); an optional cell-killing reagent (referred to herein as a Step 2 Reagent); a bi-specific reagent comprising a targeting moiety capable of binding to the aqueous insoluble nano-platform and an isotope trapping moiety (referred to herein as a Step 3 Reagent); and a radiolabeled aqueous soluble reagent (referred to herein as a Step 4 Reagent).

Figure 2:
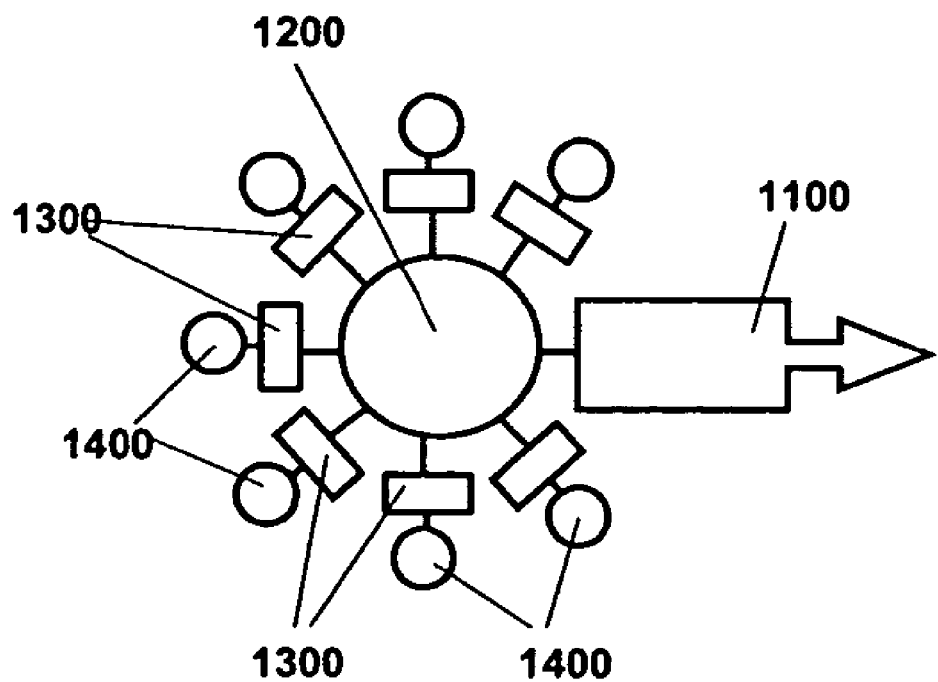
FIG. 2 is an illustration depicting a Step 1 Reagent.
Figure 3:
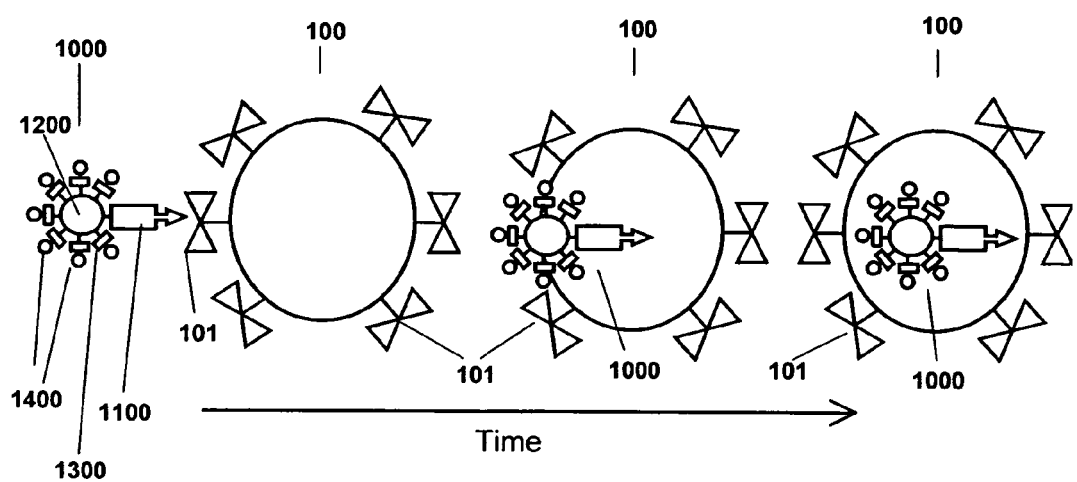
FIG. 3 is an illustration depicting the accumulation of Step 1 Reagent in cancer cells.
Figure 4:
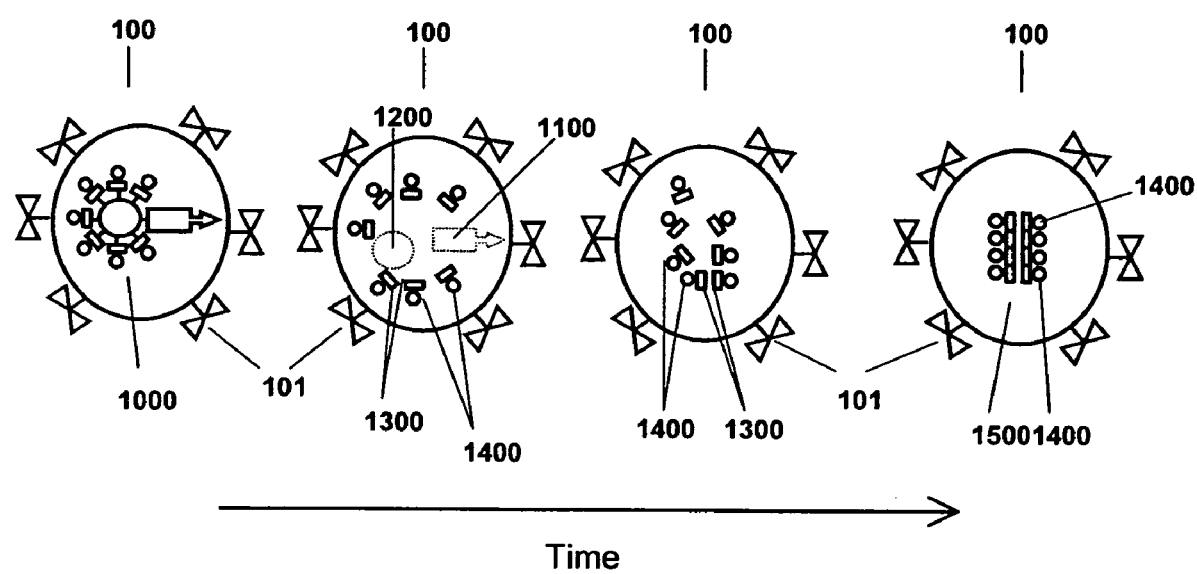
FIG. 4 is an illustration depicting the formation of aqueous insoluble nano-platform in cancer cells.

As shown in FIG. 2, the Step 1 Reagent 1000 comprises cell targeting agent 1100, an optional carrier moiety 1200, and platform building material 1300 with optionally attached additional molecular structures 1400. As shown in FIG. 3, the cell targeting agent portion of the Step 1 Reagent 1100 attaches to the targeted internalizing structure of the cancer cells 101, thereby permitting the Step 1 Reagent 1000 to be transported inside the cancer cells 100. Transport inside the cancer cells results in the Step 1 Reagent being exposed to the intracellular environment. As illustrated in FIG. 4, once inside the targeted cell, the intracellular environment causes the platform building material 1300 with an optionally attached additional molecular structure 1400 to detach from the targeting agent 1100 and the carrier moiety 1200, thereby enabling the platform building material 1300 to be converted into an aqueous insoluble nano-platform 1500 inside the targeted cancer cells. The aqueous insoluble nano-platform 1500 (with or without additional molecular structures 1400) is stable inside the targeted cancer cells and is relatively non-toxic. By stable it is meant that the nano-platform remains trapped in the cancer cell or surrounding extracellular matrix for a 1, 2, 3, 4, 5, 6 or more days to 1, 2, 3, 4 or more weeks. Relatively non-toxic is meant that the nano-platform has no significant deleterious effect on the subject, for example, moderate or minimal inflammation and/or no life threatening effect on the subject. The aqueous insoluble nano-platform with or with out additional molecular structures is referred to herein as the "nano-platform."

Figure 5:
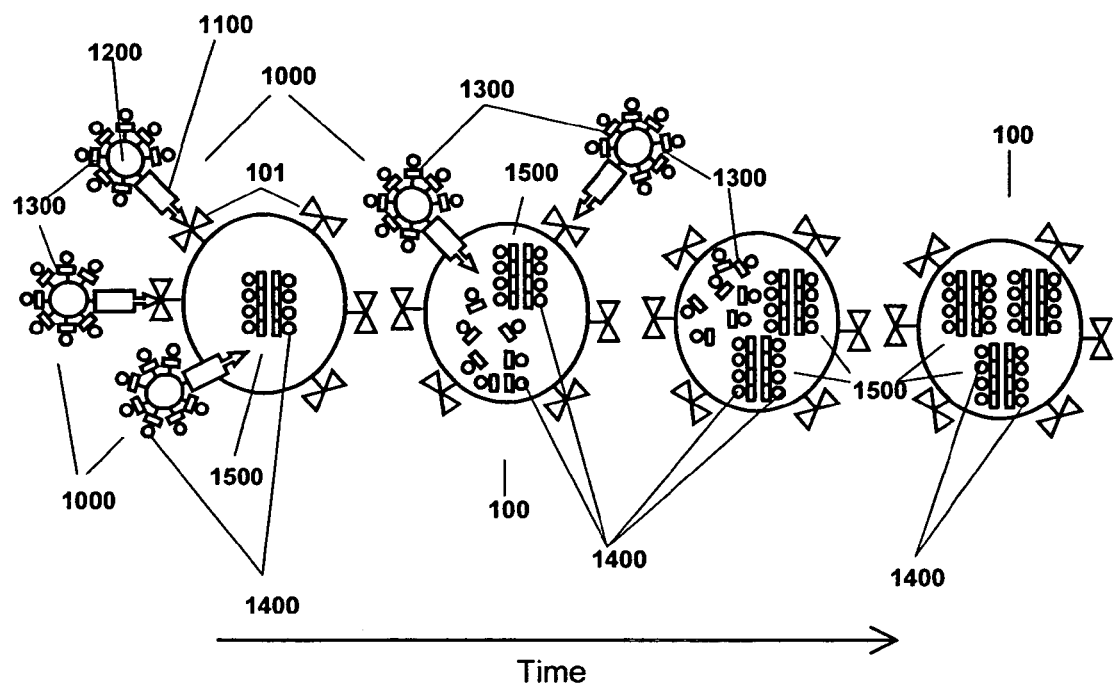
FIG. 5 is an illustration depicting the continued accumulation of the nano-platform in cancer cells.

Accumulation of the intracellular nano-platforms is achieved by continuing the administration of the Step 1 Reagent into the subject, resulting in more platform building material transported into the targeted cancer cells (See, FIG. 5). In contrast to soluble chemicals or drugs, the intracellular nano-platform accumulates over time because it is aqueous insoluble and stable and thus does not leave the targeted cancer cell.

Figure 25:
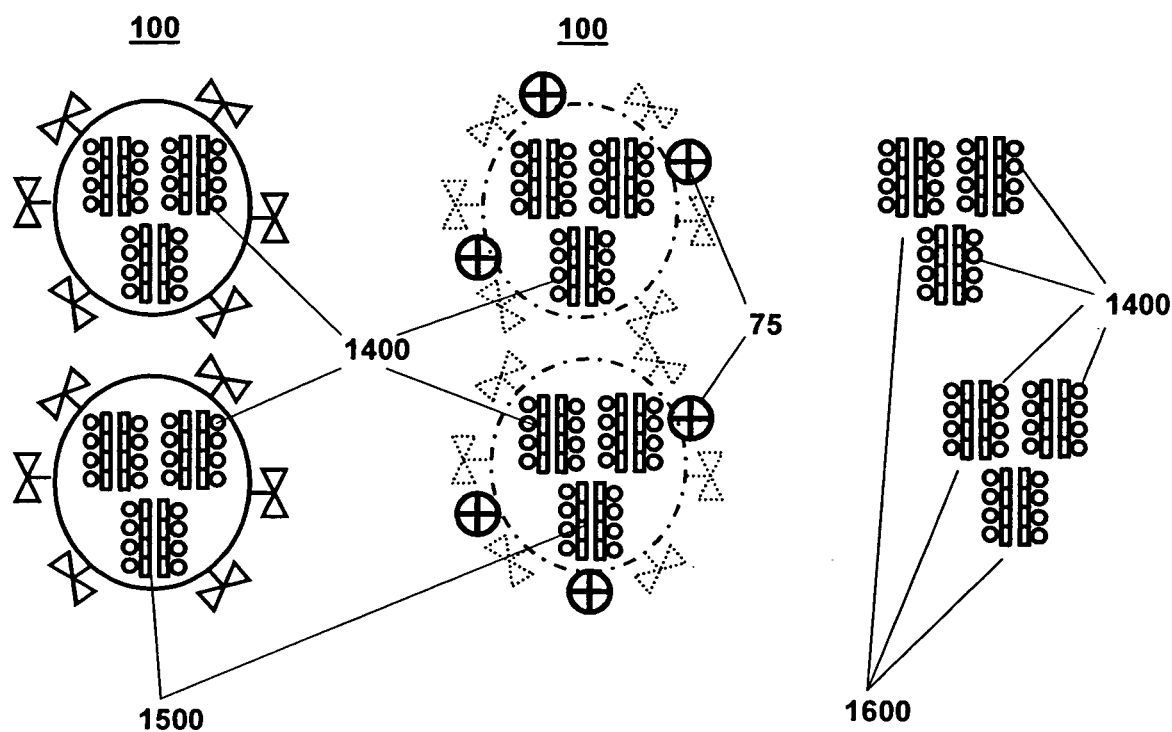
FIG. 25 is an illustration depicting the Step 2 cell-killing process.

As shown in FIG. 25, following the accumulation of the nano-platform in targeted cancer cells, the subject is optionally administered a Step 2 cell-killing Reagent 75. The Step 2 cell-killing Reagent is capable of killing some or all of the targeted cancer cells, causing the nano-platform 1500 to be relocated and retained into the extracellular space of the tumor. Once in the extracellular space the additional molecular structures 1400 on the surface of the nano-platform 1600 are accessible to bind the Step 3 Bispecific Reagent. The Step 2 cell-killing Reagent is optional as the on-going natural killing of cancer cells by the natural immune system of the body or the genetic instability of the cancer cell causing the cells to die spontaneously may be sufficient to relocate enough intracellular nano-platform to the extracellular space of the tumors to ultimately create sufficient numbers of Hot-Spots to destroy the entire tumors. The cancer specificity of the location of the Hot-Spots is enhanced by the application of such very low levels of the Step 2 Reagent that few, if any, normal cells are killed, and systemic toxicity is avoided.

The fourth step includes administering a radiolabeled aqueous soluble Step 4 Reagent that is adapted to carry radioisotopes to the extracellular tumor matrix where they are trapped and retained by the Step 3 Bispecific Reagent. This creates micro-regional radiation fields that deliver lethal irradiation to the surrounding tumor cells.

Although, in many instances, a rest period of 24 to 48 hours between steps will allow for extensive clearance of the previously administered reagent, optionally, prior to administering a reagent of a succeeding step a clearing agent is administered to facilitate the removal of any excess reagent. For example, prior to administering the Step 2 cell-killing Reagent and the Step 3 Bispecific Reagent a clearing agent is administered to facilitate removal of any non-endocytosed Step 1 Reagent. Similarly, prior to administering the Step 4 Reagent, a clearing agent is administered to facilitate removal of any Step 3 Bispecific Reagent that has not bound to the extracellular nano-platform. Clearing agents assist in the recognition of the therapeutic reagents by the subject's macrophages or increase processing by hepatocytes. Clearing agents are known in the art. Clearing agents include mannosylated or galactosylated agents that bind to the Step 1 or Step 3 Reagent. Additional clearing agents include antibodies that are generated against a Step 1 or a Step 3 Reagent to augment opsonization of the reagent by macrophages or other lymphoid cells. Alternatively, an extracorporeal circulation is established using an affinity column to remove these reagents.

Step 1 Reagent

The Step 1 Reagent is an aqueous soluble compound containing a cell targeting agent linked to a platform building material.

The cell targeting agent is any compound that directs a compound in which it is present to a desired cellular destination. The cell targeting agent is capable of being internalized into a cell. The cell targeting agent binds specifically to an endocytosing receptor or other internalizing unit on a tumor cell. For example, the cell targeting agent is a compound that is not typically endocytosed but is internalized by the process of cross-linking and capping. Thus, the cell targeting agent directs the compound across the plasma membrane, e.g., from outside the cell, through the plasma membrane, and into the cytoplasm. Alternatively, or in addition, the cell targeting agent can direct the compound to a desired location within the cell, e.g., the nucleus, the ribosome, the endoplasmic reticulum, a lysosome, or a peroxisome. Cell targeting agents include, polypeptides such as antibodies; viral proteins such as human immunodeficiency virus (HIV) 1 TAT protein or VP22; cell surface ligands; peptides such as peptide hormones; or small molecules such as hormones or folic acid. Optimally, the receptor for the cell targeting agent is expressed at a higher concentration on a tumor cell compared to a normal cells. For example, the receptor is expressed at a 2, 3, 4, 5, or more-fold higher concentration on a tumor cell compared to a non-tumor cell.

The term "antibody" as used herein refers to immunoglobulin molecules and immunologically active portions of immunoglobulin molecules, i.e., molecules that contain an antigen binding site that specifically binds (immunoreacts with) an antigen. Such antibodies include, polyclonal, monoclonal, chimeric, single chain, $F_{ab}$ and $F_{(ab')2}$ fragments, and an $F_{ab}$ expression library or polypeptides engineered therefrom. Suitable antibodies include antibodies to well characterized receptors such as the transferrin receptor (TfR) and the epidermal growth factor receptor (EGFR) as well as antibodies to other receptors, such as for example the interleukin 4 receptor (IL-4R), the insulin receptor, CD30, CD34, and the CCK-A, B, C/Gastrin receptor. Additionally, the antibody is specific for mucin epitopes; glycopeptides and glycolipids, such as the Le$^y$-related epitope (which is present on the majority of human cancers of the breast, colon and lung); the hyaluronan receptor/CD44; the BCG epitope; integrin receptors; the JL-1 receptor; GM1 or other lipid raft-associated molecules; and $G_{D2}$ on melanomas. Tumor-specific internalizing human antibodies are also selected from phage libraries as described by Poul, et al. (J. Mol. Biol. 301: 1149-1161, 2000).

A cell surface ligand is a natural ligand or some synthetic analog adapted to be specific for an internalizing structure on the targeted cancer cells. Exemplary cell surface ligands include transferrin, epidermal growth factor, interleukins, integrins, angiotensin II, insulin, growth factor antagonist, β-2-adrenergic receptor ligands or dopamine releasing protein. For example, epidermal growth factor (EGF) is used to target the epidermal growth factor receptor (EGFR) or transferrin (Tf) is used to target the transferrin receptor (e.g. TfR and TfR2).

Suitable peptide cell targeting agents include peptide hormones such as oxytocin, growth hormone-releasing hormone, somatostatin, glucagon, gastrin, secretin, growth hormone (somatotropin), insulin, prolactin, follicle stimulating hormone or arginine-glycine-aspartic acid (RGD) peptides. Methods to identify peptides that bind to internalizing receptors and are internalized are known in the art (Hart, et al., J. Biol. Chem. 269: 12468-12474, 1994).

Cell targeting agents include small molecules. A "small molecule" as used herein, is meant to refer to a composition that has a molecular weight of less than about 5 kD and most preferably less than about 4 kD. Small molecules are, e.g., nucleic acids, peptides, polypeptides, peptidomimetics, carbohydrates, lipids or other organic or inorganic molecules. For example, a small molecule is a hormone, such as estrogen, testosterone, and calciferol; folic acid or an analogue that binds to the folic acid receptor; nicotinic acetylcholine receptor agonists; or oligonucleotide receptor agonists.

The cell targeting agent is derived from a known membrane-translocating sequence. For example, the trafficking peptide includes the sequences from the human immunodeficiency virus (HIV) 1 TAT protein. This protein is described in, e.g., U.S. Pat. Nos. 5,804,604 and 5,674,980, each incorporated herein by reference. The cell targeting agent is some or all of the entire 86 amino acids that make up the TAT protein. For example, a functionally effective fragment or portion of a TAT protein that has fewer than 86 amino acids, which exhibits uptake into cells, and optionally uptake into the cell nucleus, is used. A TAT peptide that includes the region that mediates entry and uptake into cells can be further defined using known techniques. See, e.g., Franked et al., Proc. Natl. Acad. Sci, USA 86: 7397-7401 (1989).

The amino acid sequence of naturally-occurring HIV TAT protein can be modified, for example, by addition, deletion and/or substitution of at least one amino acid present in the naturally-occurring TAT protein, to produce modified TAT protein (also referred to herein as TAT protein). Modified TAT protein or TAT peptide analogs with increased or decreased stability can be produced using known techniques. In some embodiments TAT proteins or peptides include amino acid sequences that are substantially similar, although not identical, to that of naturally-occurring TAT protein or portions thereof. In addition, cholesterol or other lipid derivatives can be added to TAT protein to produce a modified TAT having increased membrane solubility.

Variants of the TAT protein can be designed to modulate intracellular localization of the Step 1 Reagent. When added exogenously, such variants are designed such that the ability of TAT to enter cells is retained (i.e., the uptake of the variant TAT protein or peptide into the cell is substantially similar to that of naturally-occurring HIV TAT). For example, alteration of the basic region thought to be important for nuclear localization (see, e.g., Dang and Lee, J. Biol. Chem. 264: 18019-18023 (1989); Hauber et al., J. Virol. 63: 1181-1187 (1989); Ruben et al., J. Virol. 63: 1-8 (1989)) can result in a cytoplasmic location or partially cytoplasmic location of TAT, and therefore, of the platform building material. Alternatively, a sequence for binding a cytoplasmic or any other component or compartment (e.g., endoplasmic reticulum, mitochondria, Golgi apparatus, lysosomal vesicles) can be introduced into TAT in order to retain TAT and the platform building material in the cytoplasm or any other compartment to confer regulation upon uptake of TAT and the platform building material.

Other sources for cell targeting moieties include, e.g., VP22 (described in, e.g., WO 97/05265; Elliott and O'Hare, Cell 88: 223-233 (1997)), or non-viral proteins (Jackson et al, Proc. Natl. Acad. Sci. USA 89: 10691-10695 (1992)).

A platform building material is a compound that when internalized into the cell via the cell targeting agent detaches from the cell targeting agent and becomes aqueous insoluble. By aqueous insoluble it is meant that the concentration of the nano-platform in an aqueous solution is less than 0.01 mM at room temperature. The concentration of an aqueous solution is less than 0.001 mM, 0.0001 mM, 0.00001 mM, or 0.000001 mM at room temperature. The platform building material forms an aqueous insoluble nano-platform spontaneously. Alternatively, the platform building material forms an aqueous insoluble nano-platform following a further chemical reaction. Chemical reactions include reactions facilitated by enzymes or other conditions present within the cellular environment such as, for example, action of an endogenous lysosomal enzyme, the acidic pH of the lysosomes, other intracellular enzymes, other conditions within another appropriate area within the cell, or attachment or intercalation into biological macrostructures inside the cell.

The platform building material once released from the cell targeting agent inside the targeted cell, forms molecular complexes that precipitate, or forms other aqueous insoluble substances such as, an insoluble polymer, a colloid, a wax, an oil, or a material that attaches or intercalates into biological macrostructures. For example, porphyrin complexes with or without appropriate metals chelated within the porphyrins will spontaneously form molecular complexes that precipitate. In addition, indoxyl glycosides produce aqueous insoluble indigo micro-precipitates, bis-indoxyl glycosides produce aqueous insoluble polymeric indigos and poly-indoxyl glycosides produce aqueous insoluble indigoid lattices.

Suitable platform building materials include for example substituted indoxyls; porphyrins; polymers such as HPMA derivatives; polysaccharides such as dextrans, gum Arabic, and chitin; dendrimers; and opio-melanins.

The cell targeting agent is linked directly to the platform building material. Alternatively, the cell targeting agent is attached indirectly to the platform building material, e.g., via a carrier moiety or a cross-linking agent. The linkage is covalent. Alternatively, the linkage is non-covalent. The linkage is such that it permits the platform building material to detach (i.e. separate) from the cell targeting agent after internalization into the cell. For example the linkage: (1) is cleaved by an intracellular enzyme or the acidic environment found within lysosomes inside the targeted cells, (2) is released by enzymatic or other actions in other environments inside targeted cells, and/or (3) attaches or intercalates into biological macrostructures inside targeted cells.

Carrier moieties allow for a higher number of platform building materials to be delivered inside the targeted cancer cells with each cell targeting agent. A carrier moiety includes for example, proteins such as serum albumin; polysaccharides, especially those modified to have functional groups; synthetic polymers and copolymers such as HPMA derivatives; dendrimers; other biopolymers including polypeptides such as polylysine; liposomes; nanoparticles; and polymeric micelles. Any substance that (a) is biologically compatible, (b) has a number of functional groups (e.g., amino groups, carboxyl groups, thiol groups, and the like) to which multiple platform building materials are attached, and (c) has a place for linking a cell targeting agent, is useful as a carrier moiety.

Optionally, the platform building materials contain an additional molecular structure such that the resulting aqueous insoluble nano-platform expresses the additional molecular structures that can bind a subsequently administered Step 3 Bispecific Reagent. Suitable additional molecular structures include for example, antigenic epitopes, neo-antigenic epitopes, ligands that bind proteins, peptides lectins, or organic structures including those prepared by combinatorial chemistry. Preferably, the additional molecular structure enables the formation of a covalent bond between the additional molecular structures on the nano-platform and the targeting moiety of the subsequently administered Step 3 Bispecific Reagent.

An example of an additional-molecular-structure: Step 3 Reagent-targeting-moiety system occurs when the additional molecular structure on the nano-platform is an irreversible inhibitor of an enzyme, and the targeting moiety of the Step 3 Bispecific Reagent is that enzyme, such that the irreversible inhibitor forms a covalent bond with one of the amino acid residues of that enzyme, thus binding the Step 3 Bispecific Reagent covalently to the aqueous insoluble nano-platform.

Alternatively, the additional molecular structure on the nano-platform is an irreversible inhibitor substrate of an enzyme that is the targeting moiety of the Step 3 Bispecific Reagent, because that enzyme is specifically modified or altered such that the enzymatic reaction is not completed and the substrate becomes covalently bound to the modified enzyme as a stable complex. Such methods are known to those skilled in the art. The mutant β-lactamase described is an example of such a modified enzyme.

Optimally, irreversible enzyme inhibitors useful as additional molecular structures on the platform building materials of the Step 1 Reagent have one or more of the following characteristics: (1) a functional group distant to the active binding portion that can be used to attach the irreversible enzyme inhibitor to the platform building material; (2) relative stability in the circulation, intracellularly and extracellularly; (3) stability properties that facilitate the chemical synthesis of the Step 1 Reagent, including the synthesis of the platform building material, as well as during the attachment of the platform building material with additional molecular structures to the carrier moiety and cell targeting agent.

Exemplary enzyme/irreversible enzyme inhibitor pairs include, mutant β-lactamase/penicillin analog or Loracarbef; UDP-N-acetylglucosamine enolpyruvoyltransferase/fosfomycin or phosphoenolpyruvate; ornithine decarboxylase/α-difluoromethyl amino acids; arginine decarboxylase/α-difluoromethyl amino acids; yeast S-adenosylmethionine decarboxylase/1,1'-(methylethanediylididenedinitrilo)-bis (3-aminoguanidine); and β-lactamase PSE-4/clavulanic acid, sulbactam, and tazobactam.

The various components of the Step 1 Reagent are selected from the repertoires of those components to suit a particular type of cancer. Having this versatility in the selection of the various components of the Step 1 Reagent allows this invention to be applied to almost all types of cancer. Exemplary targets for cell targeting agents for particular tumor types are listed in Table 1, wherein “x” denotes that the target has been identified on the particular tumor.

TABLE 1

| Target | Breast | Lung | Colon | Pancreas | Prostate | Liver | Ovary | Bladder | Stomach | Cervix |
|---|---|---|---|---|---|---|---|---|---|---|
| Transferrin - 1 & 2 Receptor | x | x | x | x | x | x | x | x | x | x |

TABLE 1-continued

| Target | | | | | | | | | | |
|---|---|---|---|---|---|---|---|---|---|---|
| EGF Receptor | x | x | x | x | x | x | x | x | x | x |
| IL-4 Receptor | x | x | x | x | x | x | x | x | x | |
| Insulin Receptor | x | x | x | x | x | x | x | ? | | x |
| CD34 | | x | | | x | x | x | x | x | ? |
| CCK-A,B,C/ Gastrin Receptor | | x | x | x | | x | x | | x | |
| Mucin | x | x | x | x | x | x | x | x | x | x |
| Le-Y | x | x | x | ? | x | x | x | x | x | x |
| Hyaluronan/ CD44 | x | x | x | x | x | x | x | x | x | x |
| IL13 Receptor | | | x | | | | x | | | |
| G-D2 on melanomas | | x | | | | | | | | |
| Somatotropin Receptor | x | | | x | | | | | | |
| Growth factor antagonists | x | x | x | x | x | x | x | x | x | x |
| Beta-2-adrenergic Receptor | x | x | | | | | | | | |
| Folic acid receptor | x | x | x | | | x | x | x | x | |

| Target | Uterus | Kidney | Melanoma | Brain | Head/Neck | Gastric | Adenomatoid Odontogenic | Pituitary Adenoma | Thyroid |
|---|---|---|---|---|---|---|---|---|---|
| Transferrin - 1 & 2 Receptor | x | x | x | x | x | x | x | x | X |
| EGF Receptor | x | x | x | x | x | | | | |
| IL-4 Receptor | | x | x | x | x | | | | |
| Insulin Receptor | x | x | x | x | | | | | |
| CD34 | x | x | x | | | | | | |
| CCK-A,B,C/ Gastrin Receptor | | ? | | | | | | | |
| Mucin | | x | ? | | x | x | | | X |
| Le-Y | x | | | | | | | | X |
| Hyaluronan/ CD44 | x | x | x | x | x | | | | |
| IL13 Receptor | | | | x | | | | | |
| G-D2 on melanomas | | | x | | | | | | |
| Somatotropin Receptor | | | | | | | | | |
| Growth factor antagonists | x | x | x | x | x | x | x | x | X |
| Beta-2-adrenergic Receptor | | | | | | | | | |
| Folic acid receptor | x | x | x | | | | | | |

Step 2 Reagent

A Step 2 Reagent is a cell-killing reagent. A cell-killing reagent or cytotoxic compound is any agent capable of causing cell death. Preferably the cell death is a result of apoptosis or results in cell lysis causing the nano-platform to be relocated to the tumor extracellular space, allowing the extracellular nano-platform to be exposed and accessible to the subsequently, previously, or concurrently administered reagents.

A cell-killing agent is any cytotoxic compound. For example, the cell-killing agent is a chemotherapeutic agent; a toxin (e.g., an enzymatically active toxin of bacterial, fungal, plant, or animal origin, or fragments thereof); a radioactive isotope (i.e., a radioconjugate); or externally applied energies such as external radiation therapy, thermal heating, or ultrasound.

Alternatively, the cell-killing agent is a non-toxic agent, such as a hormone, an anti-hormone, or a procedure such as orchidectomy, which leads to an alteration in the hormonal status of the subject and results in a cell-killing process called apoptosis that is directed against cells of a particular cell lineage that are sensitive to the hormonal status of the subject. For example, orchidectomy and/or the administration of anti-androgens causes the apoptotic killing of a large number of normal prostate cells and a variable number of prostatic cancer cells.

The chemotherapeutic compound is for example, paclitaxel, taxol, lovastatin, minosine, tamoxifen, gemcitabine, 5-fluorouracil (5-FU), methotrexate (MTX), docetaxel, vincristin, vinblastin, nocodazole, teniposide, etoposide, adriamycin, epothilone, navelbine, camptothecin, daunonibicin, dactinomycin, mitoxantrone, amsacrine, epirubicin or idarubicin.

Enzymatically active toxins and fragments thereof that can be used as the Step 2 Reagent include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

A variety of radionuclides are available for the production of radioconjugated antibodies. Examples include $^{212}$Bi, 131I, $^{111}$In, $^{90}$Y, and $^{186}$Re.

Regardless of which Step 2 cell-killing Reagent is employed, the cell-killing reagent is capable of selectively killing at least targeted cancer cells with the characteristic of being super-sensitive to being killed by the cell-killing reagent.

Step 3 Reagent

Figure 26:
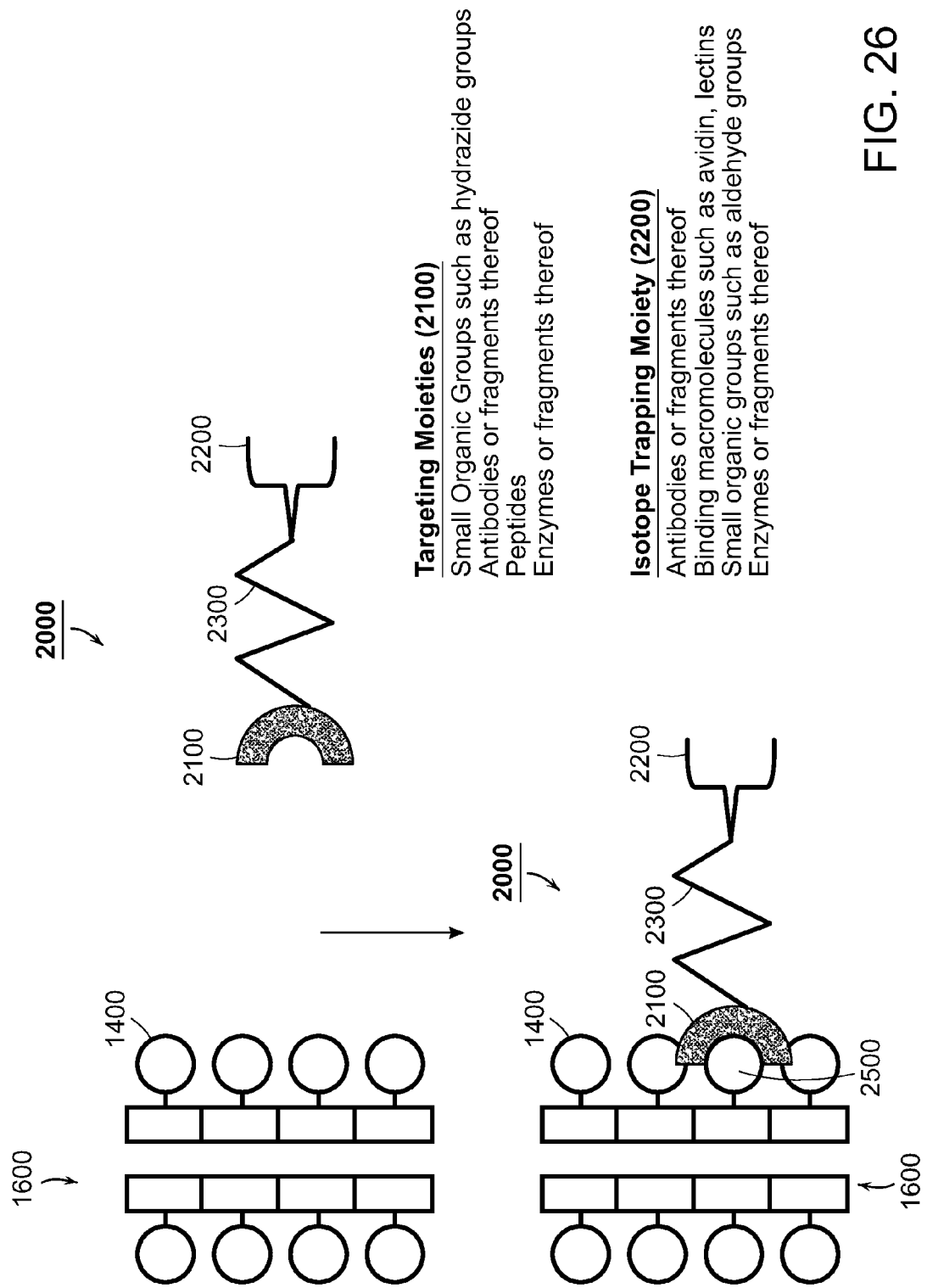
FIG. 26 is an illustration depicting the Step 3 Bispecific Reagent.

The present invention further includes introducing into the subject a Step 3 Bispecific Reagent 2000 (FIG. 26). The Step 3 Reagent is a compound containing a targeting moiety 2100 and an isotope trapping moiety.

A targeting moiety is capable of binding, with specificity and affinity, to the additional molecular structures 1400 on the aqueous insoluble nano-platform 1600.

The isotope trapping moiety 2200 is capable of trapping a radiolabeled aqueous soluble Step 4 Reagent.

Targeting moieties of the Step 3 Reagent are, for example, organic functional groups such as hydrazides, ketones, mercaptans, maleimidyls; polypeptides such as antibodies, fragments or derivatives thereof, or peptides that have been bio-technically engineered to behave like antibody combining sites; peptides, enzymes or fragments thereof, lectins; or molecules bio-technically engineered to bind to an additional molecular structure on the extracellular nano-platform.

Figure 30:
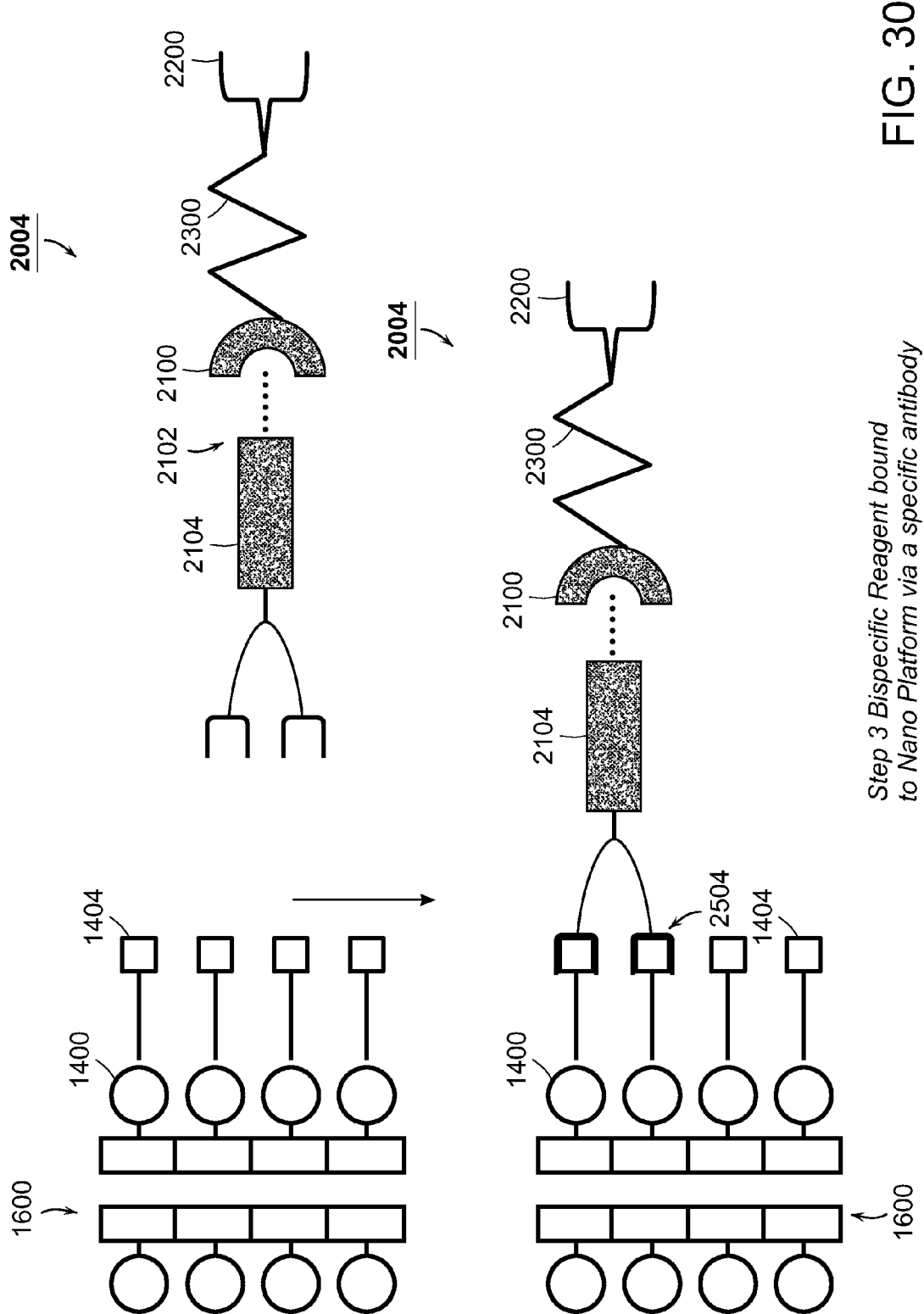
FIG. 30 is an illustration depicting the Step 3 Bispecific Reagent bound to the nano-platform via a specific antibody.

The selection of the targeting moiety is a function of the selection of the additional molecular structures on the Step 1 Reagent and its resulting nano-platform. For example, if the additional molecular structure on the nano-platform is a neo-antigen or other antigenic epitope, then the targeting moiety is an antibody or antibody fragment or peptide that has been bio-technically engineered to behave like an antibody combining site, adapted to bind the neo-antigen or other antigenic epitope with specificity and affinity. Targeting of the targeting moiety of the Step 3 Bispecific Reagent to the additional molecular structures on the extracellular nano-platform can also be the result of non-covalent high affinity and/or high avidity binding between the targeting moiety of the Step 3 Bispecific Reagent and antigenic epitopes as the additional molecular structures on the surface of the extracellular nano-platform. FIG. 30 shows an extracellular nano-platform 1600 with a number of antigenic epitopes 1404 as additional molecular structures 1400 on the surface. An antibody 2104 with specificity for these antigenic epitopes 1404 as the targeting moiety 2100 of the Step 3 Bispecific Reagent 2004 binds with high affinity and/or avidity 2504 to the antigenic epitopes 1404 as additional molecular structures 1400 on the surface of the extracellular nano-platform 1600, thus binding the Step 3 Bispecific Reagent 2004 to the extracellular nano-platform 1600.

Alternatively, if the additional molecular structure on the nano-platform is an irreversible enzyme inhibitor, then the targeting moiety is the corresponding enzyme, a mutant enzyme, a protein, or a peptide that binds to the irreversible enzyme inhibitor. As shown in FIG. 29, the Step 3 Reagent 2003 is introduced with the appropriate enzyme 2103 as the targeting moiety 2100 and comes in contact with the irreversible enzyme inhibitor 1403 as the additional molecular structure 1400 on the nano-platform 1600. The enzyme 2103 targeting moiety 2100 of the Step 3 Bispecific Reagent 2003 interacts with the irreversible enzyme inhibitor 1403, enabling the enzyme 2103 (and thus the Step 3 Bispecific Reagent) to become covalently attached 2503 to the extracellular nano-platform 1600 by a covalent bond to the irreversible enzyme inhibitor. Enzymes suitable for the targeting moiety of the Step 3 Bispecific Reagent include for example, β-lactamases, mutant β-lactamases, arginine decarboxylase, ornithine decarboxylase, chloramphenicol acetyltransferase, UDP-N-acetylglucosamine enolpyruvoyltransferase, or any specifically mutated enzyme that has its active site modified or altered so that the substrate as the additional molecular structure on the nano-platform becomes covalently attached to the enzyme but is unable to complete the catalytic reaction that causes the substrate to be released.

Figure 27:
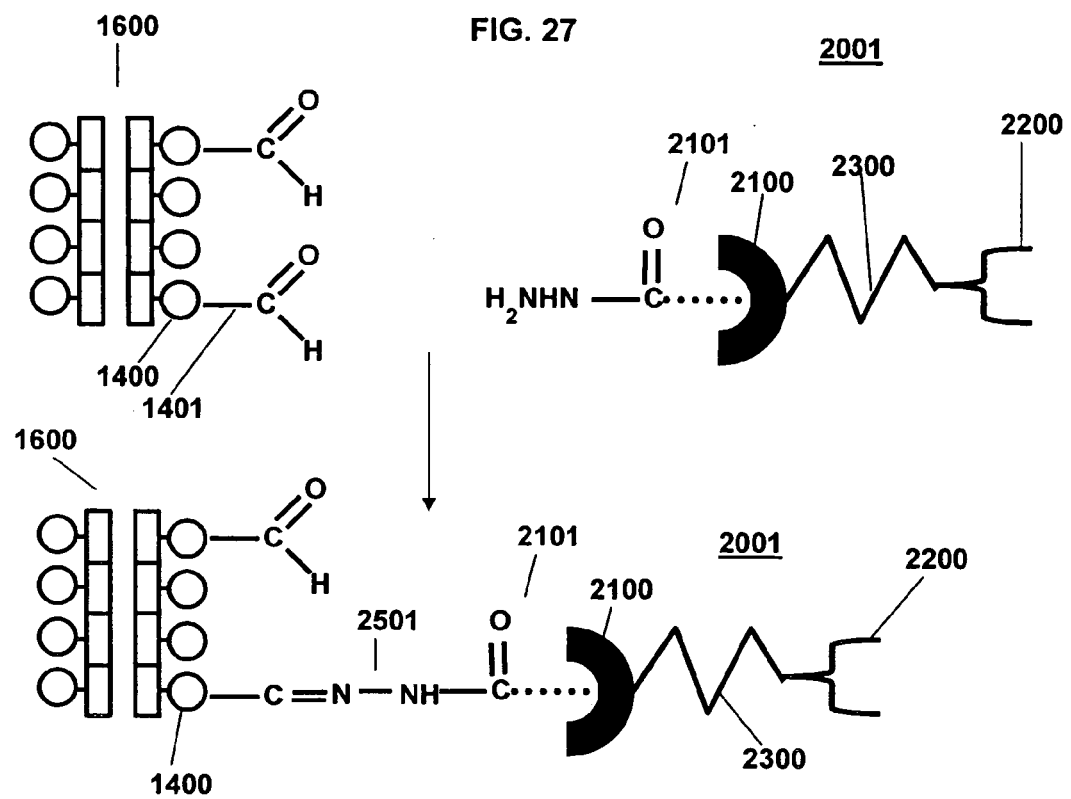
FIG. 27 is an illustration depicting the formation of the hydrazone anchoring the Step 3 Bispecific Reagent to the nano-platform.
Figure 28:
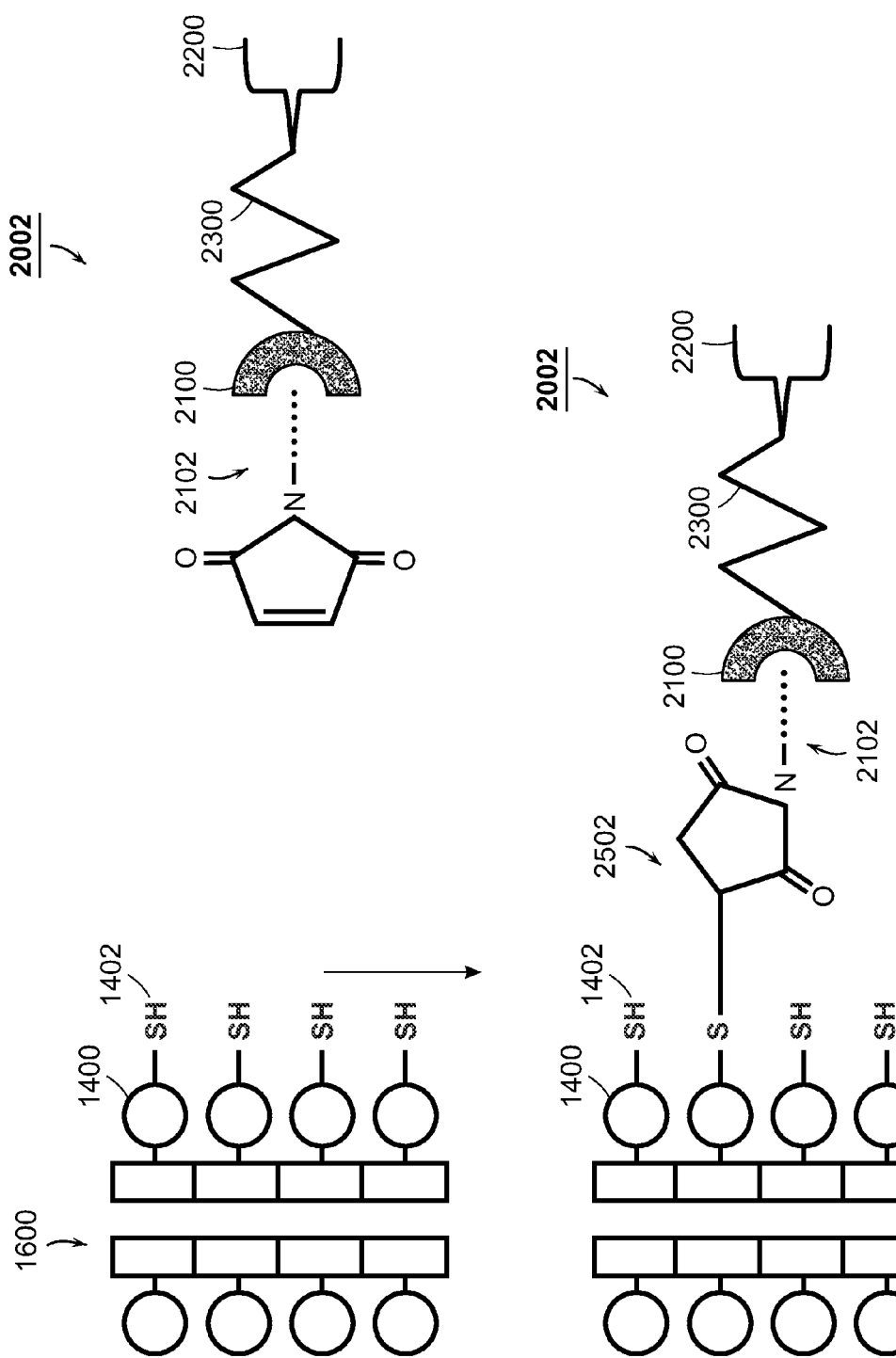
FIG. 28 is an illustration depicting the formation of the thioether anchoring the Step 3 Bispecific Reagent to the nano-platform.

If the additional molecular structure on the nano-platform is a reactive organic functional group such as an aldehyde or ketone group, then the targeting moiety of the Step 3 Reagent is a reactive organic functional group such as a hydrazide group, so the aldehyde or ketone groups are allowed to react with the hydrazide groups to form hydrazones, thereby covalently binding the Step 3 Reagent to the nano-platform. As shown in FIG. 27, the aldehyde groups are incorporated into the platform building materials either as free aldehydes or protected as acetals; if the latter, then during its residence inside the cell, the protecting group would be removed from the acetals, allowing free aldehyde groups to be present as the additional molecular structures 1401. Other organic reactive functional groups include mercaptan groups and maleimidyl groups as depicted in FIG. 28. A protected mercaptan such as an S-acetyl protected mercaptan is the additional molecular structure on the Step 1 Reagent, and is attached to the platform building material. During residence inside the cell, the acetyl group will be removed by hydrolytic enzymes so that the nano-platform 1600 will have free mercapto groups 1402 on its surface. (See, in FIG. 28). The corresponding targeting moiety 2100 of the Step 3 Reagent 2002 is a maleimidyl group 2102 which, when it comes into contact with the mercapto groups 1402 on the nano-platform 1600, forms a thioether linkage 2502, thereby covalently attaching the Step 3 Reagent to the nano-platform.

An isotope trapping moiety of the Step 3 Bispecific Reagent is capable of binding the radiolabeled Step 4 Reagent. The chemical composition of the isotope trapping moiety 2200 is determined by the radiolabeled Step 4 Reagent. The isotope trapping moiety is adapted to trap the radiolabeled aqueous soluble Step 4 Reagent within the matrix of the tumors adjacent to the region of the nano-platform.

Trapping the radiolabeled aqueous soluble Step 4 Reagent within the tumors is achieved by direct binding of the radiolabeled aqueous soluble Step 4 Reagent to the isotope trapping moiety of the Step 3 Bispecific Reagent on the extracellular nano-platform, and keeping it bound for the required period of time to create Hot-Spots. An appropriate period of time is dependent upon the radio-isotope used and is apparent to those skilled in the art. For example, for radio-labeled iodine such as $^{131}$I, an appropriate period is at least 5, 6, 7, 8, 9 10 or more days. For radiolabeled yittrium such as $^{90}$Y, an appropriate period of time is 3, 4, 5, 6 or more days.

Figure 31:
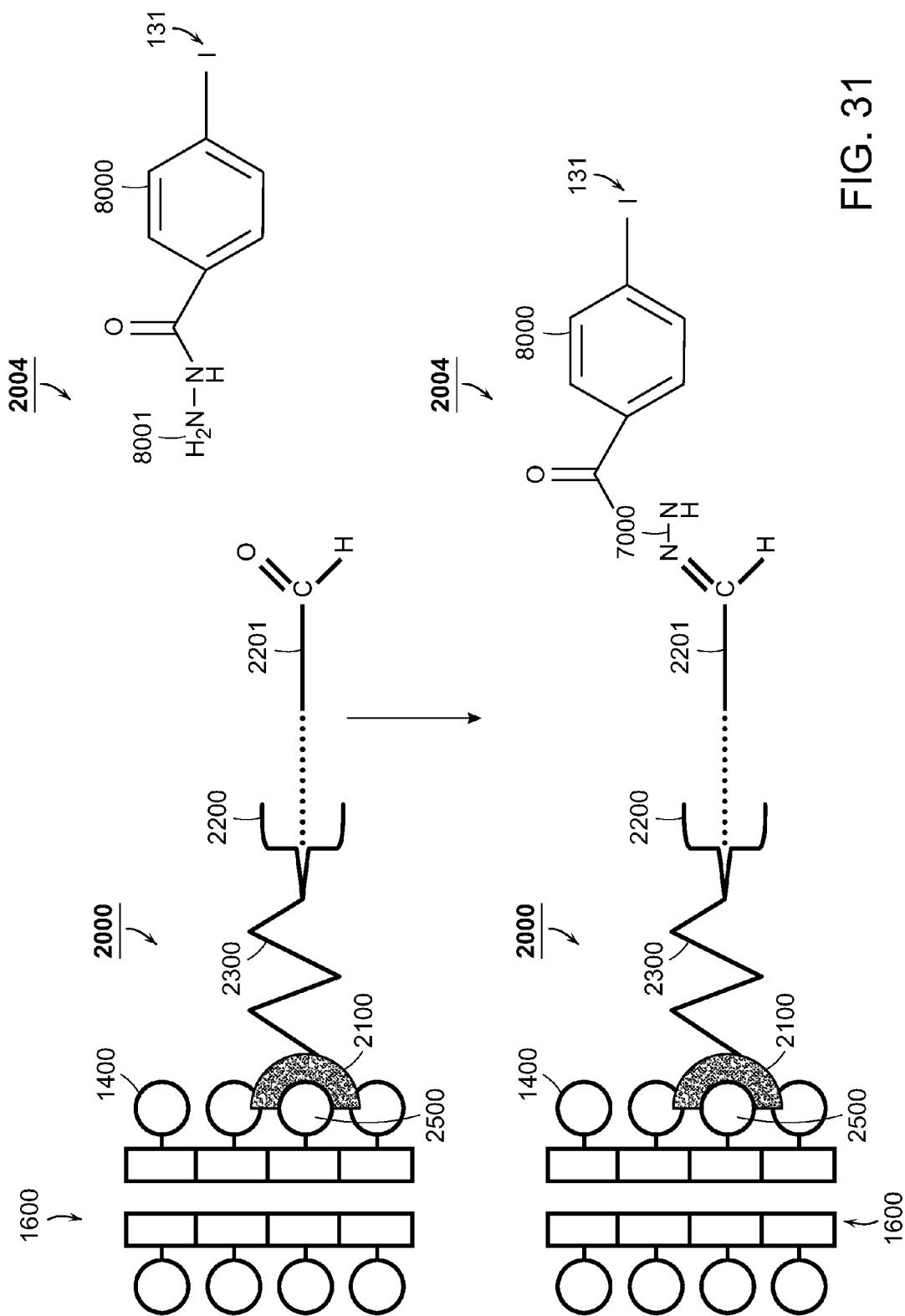
FIG. 31 is an illustration depicting the Step 3 Bispecific Reagent binding a Step 4 Reagent that is a hydrazide.

Step 4 Reagents capable of binding to the isotope trapping moiety of the Step 3 Reagent on the extracellular nano-platform include the reactive organic functional groups discussed above for the targeting moiety of the Step 3 Bispecific Reagent, such as hydrazide groups that bind to aldehyde groups to form hydrazones. For example, as shown in FIG. 31, the Step 3 Bispecific Reagent 2005, which becomes attached 2500 to the surface of the extracellular nano-platform 1600, can have aldehyde groups 2201 as the isotope trapping moieties 2200, and the radiolabeled aqueous soluble Step 4 Reagent 8000 can attach to the aldehyde groups 2201 via a hydrazide group 8001 that is present in its molecular structure to form a hydrazone 7000, thereby covalently attaching the radiolabeled aqueous soluble Step 4 Reagent to the extracellular nano-platform, thus causing the radioisotopes (for example, $^{131}$I) to be retained on the extracellular nano-platform in the tumors for an extended period of time, for example 5-10 days, during which time the radioisotopes create Hot-Spots that expose the tumor cells within a radius of 1-2 mm to lethal irradiation.

Figure 32:
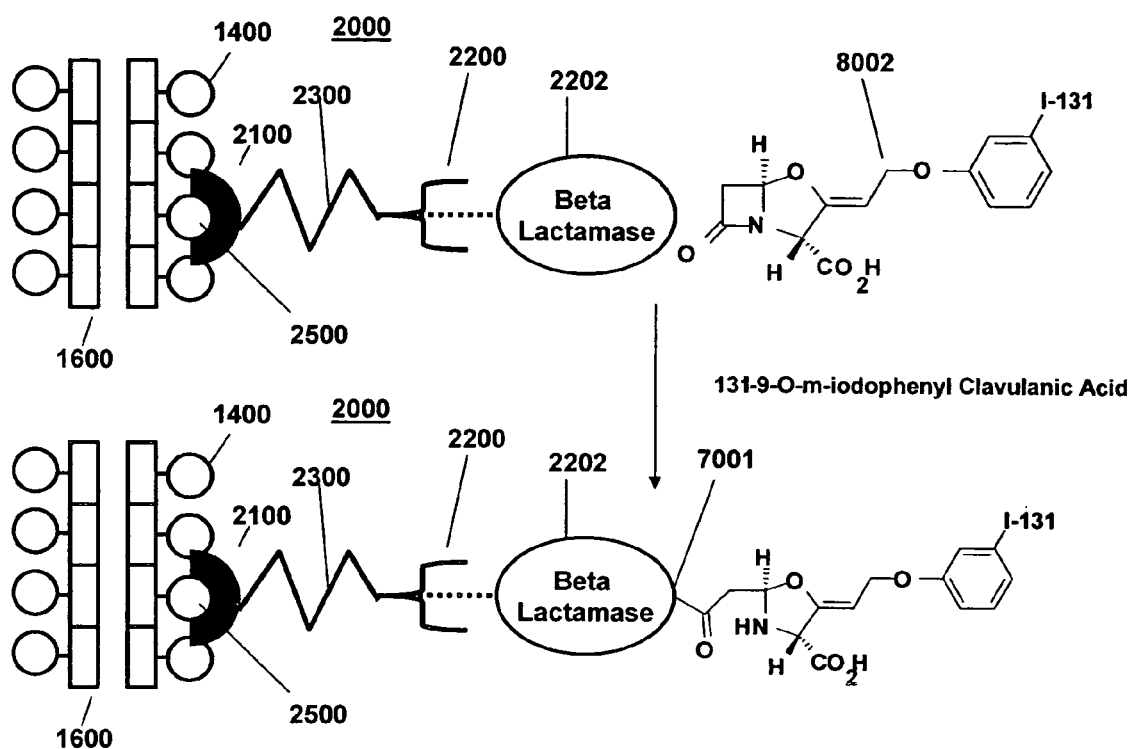
FIG. 32 is an illustration depicting the Step 3 Bispecific Reagent binding a Step 4 Reagent that is an irreversible enzyme inhibitor.

Alternatively, the isotope trapping moiety of the Step 3 Bispecific Reagent is an enzyme, and the radiolabeled aqueous soluble Step 4 Reagent is a radiolabeled irreversible inhibitor of that enzyme. For example, as shown in FIG. 32 the isotope trapping moiety 2200 of the Step 3 Bispecific Reagent 2006 is a β-lactamase enzyme 2202 that is attached 2500 to the additional molecular structures 1400 on the surface of the nano-platform 1600 by the targeting moiety 2100 of the Step 3 Bispecific Reagent. In this example the radiolabeled aqueous soluble Step 4 Reagent 8002 is an $^{131}$I-iodo derivative of penicillanic acid or lithium $^{131}$I-9-O-m-iodophenyl clavulanate (J. Enzyme Inhibition, 1: 83-104, 1986), which, when introduced into the circulation, comes in contact with the β-lactamase 2202 attached to the extracellular nano-platform 1600, interacts with the binding site on the β-lactamase, and becomes bound to the β-lactamase as an irreversible enzyme inhibitor 7001, thereby attaching the aqueous soluble Step 4 Reagent radioisotopes to the extracellular nano-platform 1600 in the tumors for the required period of time to create Hot-Spots that expose the surrounding tumor cells to lethal irradiation.

Figure 33:
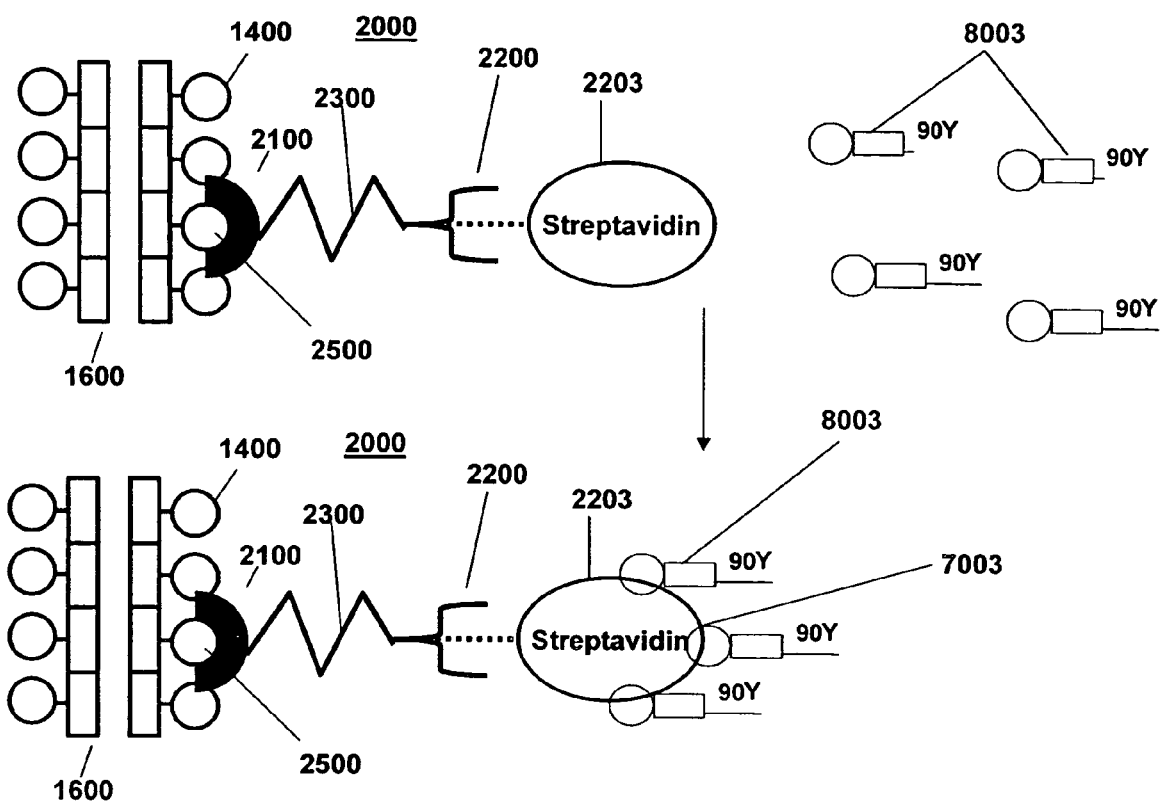
FIG. 33 is an illustration depicting the Step 3 Bispecific Reagent binding a Step 4 Reagent via a high affinity receptor.

Alternatively, the isotope trapping moiety of the Step 3 Bispecific Reagent is also an antibody or antibody fragment or derivative thereof, a lectin, or other protein or structure capable of binding a radiolabeled aqueous soluble Step 4 Reagent with high affinity and/or high avidity. As shown in FIG. 33, the isotope trapping moiety 2200 of the Step 3 Bispecific Reagent 2007 is Streptavidin 2203, the Step 3 Bispecific Reagent 2007 being attached to the extracellular nano-platform 1600 by a targeting moiety 2100 of the Step 3 Bispecific Reagent. In this example, the radiolabeled aqueous soluble Step 4 Reagent 8003 can be a biotin derivative such as a $^{90}$Y-biotin derivative (Weiden and Breitz, Crit. Rev. Oncol. Hematol. 40: 27-51, 2001; Paganelli, et al., Cancer Biother. Radiopharm. 16: 227-235, 2001). When the radiolabeled aqueous soluble Step 4 Reagent 8003 is introduced into the circulation, it becomes bound 7003 to the Streptavidin attached to the extracellular nano-platform within the tumors with very high affinity, thereby trapping the radiolabeled Step 4 Reagent $^{90}$Y radioisotopes as bound to the extracellular nano-platform in the tumors for the required period of time to generate Hot-Spots that expose the surrounding tumor cells to lethal irradiation. Since Streptavidin has four binding sites for biotin (Chalet and Wolf, Arch. Biochem. Biophys. 106: 1, 1964), a four-fold amplification of the amount of radioisotopes trapped within the tumors is achieved by using Streptavidin as the isotope trapping moiety of the Step 3 Bispecific Reagent to bind and trap the radiolabeled biotin Step 4 Reagent.

Since antibodies can be used as both the targeting moiety of the Step 3 Reagent to bind to antigenic epitopes as the additional molecular structures on the extracellular nano-platform, and as the isotope trapping moiety of the Step 3 Reagent to bind the radiolabeled aqueous soluble Step 4 Reagent, the two binding activities can be achieved in one molecule by using a Step 3 Reagent that is a bispecific antibody. One half of the bispecific antibody can be an antibody specific for antigenic epitopes as the additional molecular structures on the extracellular nano-platform, and the other half of the bispecific antibody can be an antibody specific for a hapten structure on the radiolabeled aqueous soluble Step 4 Reagent.

Alternatively, trapping the radiolabeled aqueous soluble Step 4 Reagent within the tumors is achieved by converting a radiolabeled aqueous soluble Step 4 Reagent into a radiolabeled aqueous insoluble product, most advantageously through the catalytic action of an appropriate enzyme that is the isotope trapping moiety of the Step 3 Bispecific Reagent. This method provides a great amplification of the amount of radioisotopes that can be trapped within the tumors. The amplification will be governed by the concentration of the radiolabeled aqueous soluble Step 4 Reagent and the turnover number of the enzyme for the radiolabeled aqueous soluble Step 4 Reagent substrate.

Figure 34:
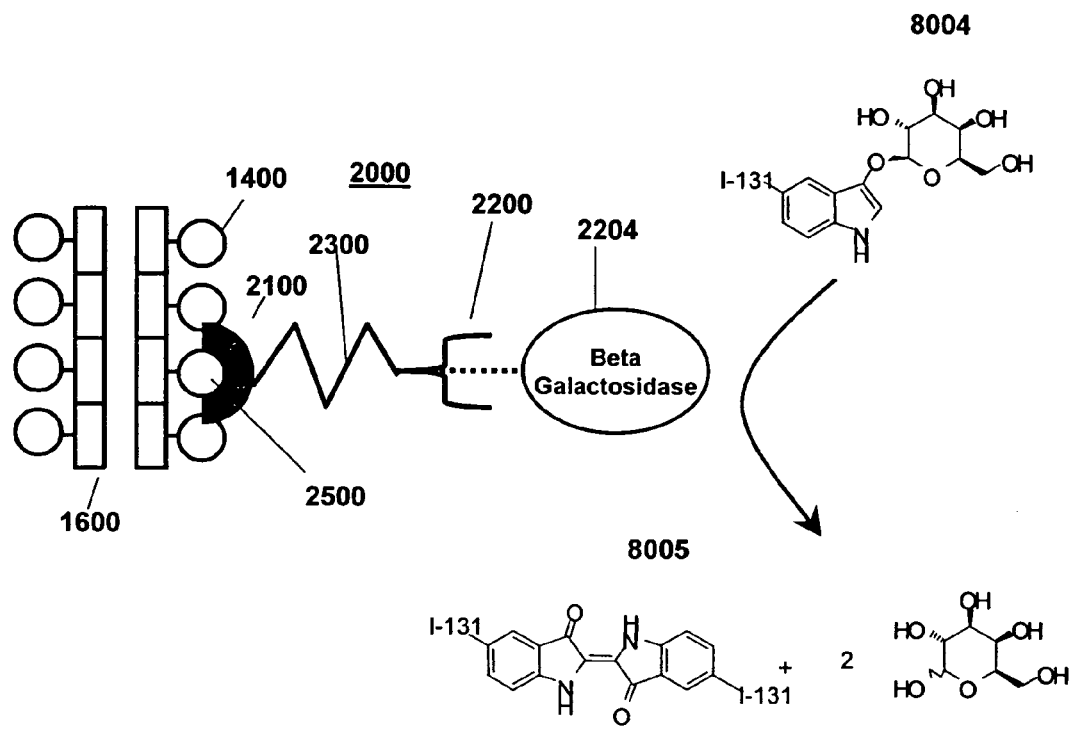
FIG. 34 is an illustration depicting the Step 3 Bispecific Reagent which has an enzyme as its isotope trapping moiety that converts an indoxyl galactoside to an indigo derivative

Preferably, the isotope trapping moiety of the Step 3 Bispecific Reagent is an enzyme that is capable by its catalytic action of converting a subsequently administered radiolabeled aqueous soluble Step 4 Reagent into a radiolabeled aqueous insoluble product that is trapped within the tumor matrix. As shown in FIG. 34, the enzyme as the isotope trapping moiety 2200 of the Step 3 Bispecific Reagent 2008 is, for example, a glycosidase such as β-D-galactosidase 2204 that is attached to the extracellular nano-platform 1600 through the targeting moiety 2100 of the Step 3 Bispecific Reagent 2008, and converts a radiolabeled aqueous soluble Step 4 Reagent 8004 such as $^{131}$I-5-iodoindoxyl-3-galactoside 8004 to a radiolabeled aqueous insoluble product such as $^{131}$I-5,5'-diiodoindigo 8005 via the catalytic action of the enzyme in cleaving the galactoside moiety from the indoxyl moiety. This results in an intermediate that is a radiolabeled aqueous soluble indoxyl derivative that undergoes spontaneous oxidative dimerization to form a radiolabeled aqueous insoluble indigo derivative product 8005. These compounds rapidly form precipitates within close proximity of the enzyme as the isotope trapping moiety 2200 of the Step 3 Bispecific Reagent 2008 that is attached to the extracellular nano-platform 1600 (Holt, Nature 169: 271-273, 1952; Holt and Sadler, Proc. Roy. Soc. B, 148: 495-505, 1958), trapping the radioisotopes within the tumors to create Hot-Spots to deliver lethal irradiation to the surrounding tumor cells. The precipitate remains in place within the tumor matrix for an extended period of time because it is aqueous insoluble, and because of the absent or restricted lymphatics found within tumors (Jain, Adv. Drug Deliv. Rev. 26: 71-90, 1997; Jain, Cancer Res. 50: 814s-819s, 1990; Butler, et al., Cancer Res. 35: 3084-3088, 1975) and the absent, limited number of, or ineffective macrophages found within tumors, which might otherwise remove the precipitate by phagocytosis (Balm, et al., Cancer 54: 1010-1015, 1984; Vaage, Int. J. Cancer 50: 69-74, 1992; Bingle, et al., J. Pathol. 196: 254-265, 2002). The use of an enzyme as the isotope trapping moiety of the Step 3 Bispecific Reagent in this catalytic manner has the advantage over the methods of direct binding of the radiolabeled aqueous soluble Step 4 Reagent in being able to amplify the amount of radioisotopes that is trapped within the tumors, thereby increasing the effective dose of lethal radiation that can be delivered to the tumor cells, increasing the likelihood of an effective treatment for the tumors. The enzyme used as the isotope trapping moiety of the Step 3 Bispecific Reagent in this catalytic manner is preferably a non-mammalian enzyme for which there is no comparable enzyme reaction found in the human circulation and for which there are no substrates found in the human circulation; these enzymes include, for example, β-lactamases, penicillin acylases, arginine decarboxylases, and sialidases. However, even mammalian enzymes, including human enzymes, are used in this catalytic manner if they do not catalyze any host reactions in the human circulation in significant amount, and provided there is none or a limited amount of natural substrates to compete for the enzyme, and that there are no circulating enzymes that can react in significant amounts with the substrate that will be used as the radiolabeled aqueous soluble Step 4 Reagent. Several enzymes that represent specificities found in mammalian cells are known in the art and include, alkaline phosphatase, β-glucuronidase, and β-galactosidase. Human enzymes have some advantages over non-mammalian enzymes for use in this catalytic manner, since they may reduce potential host immunological reactions (Wolfe, et al., Bioconjugate Chem. 10: 38-48, 1999; Smith, et al., J. Biol. Chem. 272: 15804-15816, 1997; Laethem, et al., Arch Biochem. Biophys. 332: 8-18, 1996; Houba, et al., Biochem. Pharm. 52: 455-463, 1996). The most important aspect of selecting a suitable enzyme for use as the isotope trapping moiety of the Step 3 Bispecific Reagent in this catalytic manner is to be sure that the Step 4 reaction that is catalyzed causes the formation of a radiolabeled aqueous insoluble product that remains trapped within the matrix of the tumor (most likely in the form of a precipitate or a highly hydrophobic product that becomes enmeshed in the tumor matrix) for the required period of time to create Hot-Spots that expose the surrounding tumor cells to lethal irradiation. Catalytic enzymes suitable as the isotope trapping moiety of the Step 3 Bispecific Reagent in this invention include, for example, β-lactamase; penicillin-G and -V amidase; nitroreductase; glycosidases of all types, for example β-galactosidase, β-glucosidase, β-glucuronidase, sialidase, and the like; carboxypeptidase A; carboxypeptidase G2; cytosine deaminase; alkaline phosphatase; sulfatase; or genetically engineered mutants of such enzymes.

The targeting moiety and the isotope trapping moiety of the Step 3 Bispecific Reagent are linked covalently (See, FIG. 26). Alternatively, the targeting moiety and the isotope trapping moiety are linked non-covalently. When reactive organic functional groups (for example, aldehyde or hydrazide groups) are used in either the targeting or isotope trapping moiety, the targeting moiety or isotope trapping moiety as a reactive functional group will also require a suitable functionality for attaching the reactive organic functional group to the other moiety, respectively, of the Step 3 Bispecific Reagent, which most often will be a macromolecule, often a protein. This suitable functionality attaches the reactive organic functional group as the targeting moiety or isotope trapping moiety to one of the amino acid residues of the other moiety as a protein without affecting the binding or enzymatic activity of the protein (Hermanson, *Bioconjugate Techniques*, Part I, Academic Press, San Diego, 1996). In many of the other selections for the Step 3 Bispecific Reagent, the formation of the Step 3 Bispecific Reagent involves joining two different macromolecules to create hetero-conjugates. Coupling procedures are known in the art (Hermanson, *Bioconjugate Techniques*, Part II, Academic Press, San Diego, 1996). It is also possible to use bio-engineering and recombinant biology techniques to generate fusion proteins, which, upon expression and purification, can provide suitable Step 3 Bispecific Reagents.

Step 4 Reagent

The Step 4 Reagent contains a radiolabeled molecule. The radioisotope is attached to the Step 4 Reagent directly, i.e., covalently. Alternatively, the radioisotope is attached to the Step 4 Reagent indirectly, for example, via a chelating agent. Radioisotopes include for example, Iodine-131 ($^{131}$I), Yttrium-90 ($^{90}$Y), Copper-67 ($^{67}$Cu), Rhenium-186 ($^{186}$Re), Rhenium-188 ($^{188}$Re), Lutetium-177 ($^{177}$Lu), Astatine-211 ($^{211}$As), Bismuth-212 ($^{212}$Bi), Bismuth-213 ($^{213}$Bi), Rhodium-103m ($^{103m}$Rh), Iodine-125 ($^{125}$I), and Indium-111 ($^{111}$In) (Carlsson, et al., Radiother Oncol. 66(2): 107-117, 2003).

Preferably the radiolabeled Step 4 Reagent is of low molecular weight. Low molecular weight compounds provide better circulation, biodistribution, tumor penetration, and a reduction in potential immunogencity. Additionally, a low molecular weight radiolabeled aqueous soluble Step 4 Reagent that is not trapped within the tumor extracellular matrix is more rapidly excreted thereby minimizing systemic toxicity.

By low molecular weight it is meant that the compound is less that 25 kD, preferably less than 10 kD, more preferably less than 5 kD and most preferably less than 1 kD.

The Step 4 Reagent is adapted to be trapped by the isotope trapping moiety of the Step 3 Reagent by binding directly and specifically to the isotope trapping moiety of the Step 3 Bispecific Reagent. Alternatively, the Step 4 Reagent is enzymatically converted by the isotope trapping moiety of the Step 3 Reagent into a radiolabeled aqueous insoluble product that becomes trapped within the tumor extracellular matrix adjacent to the nano-platform. Immobilization of the Step 4 Reagent radioisotopes within the tumor extracellular matrix creates micro-regional radiation fields (Hot-Spots) that deliver lethal irradiation to the surrounding tumor cells.

The Step 4 reagent binds to the isotope trapping moiety via a reactive functional group capable of binding to the isotope trapping moiety of the Step 3 Reagent, for example as an irreversible enzyme inhibitor that binds directly to the isotope trapping moiety or as a small molecule such as a hapten or peptide that is adapted to bind with very high affinity or high avidity to the isotope trapping moiety. High avidity is defined by a Ka of at least ~$10^{10}$ mol$^{-1}$ or more. Preferably the Ka is ~$10^{12}$ mol$^{-1}$. Most preferably, the Ka is ~$10^{15}$ mol$^{-1}$.

Reactive organic functional groups include for example aldehydes, ketones, hydrazides, mercaptans, or maleimide groups that react with the corresponding organic reactive functional group on the other reagent, but do not react readily with molecular structures present within the circulation of the subject on the paths that the two reagents traffic. For example, if the isotope trapping moiety of the Step 3 Bispecific Reagent is an aldehyde group, the radiolabeled aqueous soluble Step 4 Reagent has a hydrazide functional group. When the hydrazide group on the radiolabeled aqueous soluble Step 4 Reagent comes into contact with the aldehyde group as the isotope trapping moiety of the Step 3 Reagent, it forms a hydrazone, and thus covalently attaches the radiolabeled aqueous soluble Step 4 Reagent to the nano-platform.

Suitable enzymes as the isotope trapping moiety of the Step 3 Reagent and irreversible enzyme inhibitors as the Step 4 Reagent are well known in the art as discussed supra. Preferably, the specificities of the enzymes are for substrates not found in significant quantities in the host species' circulation or extracellular matrix or on the paths that the Step 3 Bispecific Reagents traffic during their use in the invention. Advantageously, the isotope trapping moiety of the Step 3 Bispecific Reagent is a non-mammalian enzyme with specificity for substrates generally not found in the host species, such as a penicillinase or a penicillin amidase.

The Step 4 Reagent includes haptens such as 2-nitro-5-iodo-phenol (NIP), 4-(4'-iodophenyl)benzoate, and 4-(4'-iodophenyl)benzenearsonate, in which the iodo groups are radioactive. Alternatively, peptides are radiolabeled to include radioisotopes. Radiolabeled organic molecules can be readily attached to the peptides. For example, $^{131}$I-p-iodobenzoic acid can be attached to the α-amino group on a peptide through the formation of an amide, and chelating agents such as 1,4,7,10-tetraazacyclododecane-N,N',N'',N'''-tetraacetic acid (DOTA) that bind $^{90}$Y and other metal radioisotopes with very high affinity can be conjugated to peptides.

The peptides are polymers of L-amino acids, D-amino acids, or a combination of both. For example, the peptides are D retro-inverso peptides. The term "retro-inverso isomer" refers to an isomer of a linear peptide in which the direction of the sequence is reversed; the term "D-retro-inverso isomer" refers to an isomer of a linear peptide in which the direction of the sequence is reversed and the chirality of each amino acid residue is inverted. See, e.g., Jameson et al., Nature, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Exemplary Step 4 Reagent/isotope trapping moiety pairs include radiolabeled biotin/Streptavidin or radiolabeled FITC/anti-FITC antibody.

Step 4 Reagents include compounds composed of a hydrophobic core with an attached hydrophilic group that are enzymatically altered by the isotope trapping moiety. For example, a hydrophilic group is attached to an aromatic OH (hydroxy) group, which may be most advantageous when the OH group is in a position to hydrogen bond to a heteroatom in another part of the radiolabeled aqueous soluble Step 4 Reagent. In addition, this type of radiolabeled aqueous soluble Step 4 Reagent contains a radioisotope, most advantageously one, such as an iodo group, that maintains the hydrophobicity of the radiolabeled aqueous insoluble product produced by the reaction of the radiolabeled aqueous soluble Step 4 Reagent substrate with the enzyme as the isotope trapping moiety of the Step 3 Bispecific Reagent.

A common feature of many of the potential radioisotope-containing molecular structures for this class of radiolabeled aqueous soluble Step 4 Reagents, but not meant to be exclusive, is an OH (hydroxyl) group on an aromatic nucleus, which is used to prepare a suitable enzyme substrate by attaching, for example, a phosphate group as the substrate group for a phosphatase, a sulfate for a sulfatase, a galactose for galactosidase, a glucose for a glucosidase, a glucuronide 2 for a glucuronidase, etc. It is even more desirable if the OH group, once it is liberated by enzymatic cleavage of the attached substrate, can form an internal hydrogen bond with an appropriately situated heteroatom that is part of the molecular structure. For example, these core structures, to which a radiolabel and an appropriate substrate group are added, include, but are not limited to, derivatives of alkylsalicylates, N-benzylsalicylamides, 2-(2"-hydroxyphenyl)benzimidazoles, 5,6,7,8-β-tetralol carboxylic acid-β-naphthylamides, 2-hydroxybenzophenones, 3-hydroxy-2-naphthoic acid anilides, dihydroquinophthalones, menahydroquinones, 2-(2'-hydroxyphenyl)-4(3H)-quinazolinones, 2-(2'hydroxyphenyl)-benzotriazoles, porphyrin derivatives, and the like.

Another way to make use of the catalytic action of the isotope trapping moiety of the Step 3 Bispecific Reagent, as an enzyme, is the enzymatic conversion of a radiolabeled aqueous soluble Step 4 Reagent into an active intermediate that spontaneously reacts to form a radiolabeled aqueous insoluble product, and thereby again takes advantage of the great amplification potential of a high enzyme turnover number to vastly increase the amount of radioisotopes that can be trapped within the tumor extracellular matrix for the required period of time to create micro-regional radiation fields (Hot-Spots) to deliver lethal irradiation to the surrounding tumor cells. Many molecular structures are suitable to make this kind of radiolabeled aqueous soluble Step 4 Reagent, including enzyme substrates whose enzymatic cleavage produces monomers that are active intermediates for forming aqueous insoluble polymers. Examples of suitable enzyme substrates that could be used as such radiolabeled aqueous soluble Step 4 Reagents include, but are not limited to, 1) radiolabeled aqueous soluble indoxyl derivatives whose enzymatic cleavage of pendant groups yields a reactive indoxyl that rapidly undergoes oxidative dimerization to form radiolabeled aqueous insoluble indigo derivative products and 2) derivatives of penicillins whose cleavage by penicillinase leads to an electronic rearrangement that releases a radiolabeled aqueous insoluble product.

Reagent Preparation

The compositions of the invention are prepared by joining the components from each of the above described groups by chemical coupling in any suitable manner known in the art. Many known chemical cross-linking methods are non-specific, i.e., they do not direct the point of coupling to any particular site on the targeting moiety. As a result, use of non-specific cross-linking agents may attack functional sites or sterically block active sites, rendering the conjugated proteins biologically inactive.

One way to increasing coupling specificity is to direct chemical coupling to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a cross-linking reaction would not otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. There are several intermolecular cross-linking reagents which can be utilized, See for example, Means and Feeney, CHEMICAL MODIFICATION OF PROTEINS, Holden-Day, 1974, pp. 39-43. Among these reagents are, for example, succinimidyl 3-(2-pyridyldithio) propionate (SPDP) or N,N'-(1,3-phenylene) bismaleimide (both of which are highly specific for sulfhydryl groups and form irreversible linkages); N,N'-ethylene-bis-(iodoacetamide) or other homologs having 6 to 11 carbon methylene bridges (which are relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonyl-chloride (which reacts principally with amino groups); hexamethylenediisocyanate or diisothiocyanate, or azophenyl-p-diisocyanate (which reacts principally with amino groups); glutaraldehyde (which reacts with several different side chains) and bisdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl) cyclohexane-1-carboxylate ("SMCC"), m-maleimidobenzoyl-N-hydroxysuccinimide ester ("MBS"), and succinimide 4-(p-maleimidophenyl) butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis (succinimidylpropionate) ("DSP"), and N-succinimidyl 3-(2-pyridyldithio) propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, CHEMISTRY OF PROTEIN CONJUGATION AND CROSS-LINKING, CRC Press (1991).

Chemical cross-linking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the cross-linking reagent, such as in "long-chain SPDP" (Pierce Chem. Co., Rockford, Ill., cat. No. 21651 H).

Alternatively, the compositions of the invention are produced as a fusion peptide which can conveniently be expressed in known suitable host cells. Fusion peptides, as described herein, can be formed and used in ways analogous to or readily adaptable from standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene is synthesized by conventional techniques including automated DNA synthesizers. Alternatively, PCR amplification of gene fragments is carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain).

Pharmaceutical Compositions

The compositions of the invention can be incorporated into pharmaceutical compositions suitable for administration. Such compositions typically comprise the Step 1, Step 2, Step 3 or Step 4 Reagent, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, intramuscular, intraperitoneal, intravenous, subcutaneous, intranasal, epidural, transdermal (topical), transmucosal, rectal administration and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PDX polypeptide or PDX encoding nucleic acid) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery. In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to cancer cells with monoclonal antibodies or other cell targeting agents) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specifications for the dosage unit forms of the invention are dictated by and directly dependent on the unique characteristics of the active compound and the particular therapeutic effect to be achieved.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of the Therapeutics of the invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of protein reagents of the present invention with which to treat each individual patient. Initially, the attending physician may administer low doses of the reagents of the present invention and observe the patient's response. Larger doses of the reagents of the present invention may be administered until the optimal therapeutic effect is obtained for the patient, and at that point the dosage is not increased further. However, suitable dosage ranges for intravenous administration of the Therapeutics of the present invention are generally about 0.020 milligrams (mg) to 1 gram of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

The duration of intravenous therapy using the Therapeutics of the present invention will vary, depending on the severity of the disease being treated and the condition and potential idiosyncratic response of each individual patient. It is contemplated that the duration of each application of the reagents of the present invention will be in the range of 1-2 hours to 15 days of continuous intravenous administration. Ultimately the attending physician will decide on the appropriate duration of intravenous therapy using the pharmaceutical compositions of the present invention.

The pharmaceutical compositions can be included in a kit, container, pack, or dispenser together with instructions for administration.

The invention will be further illustrated in the following non-limiting examples.

Example 1

Figure 6:
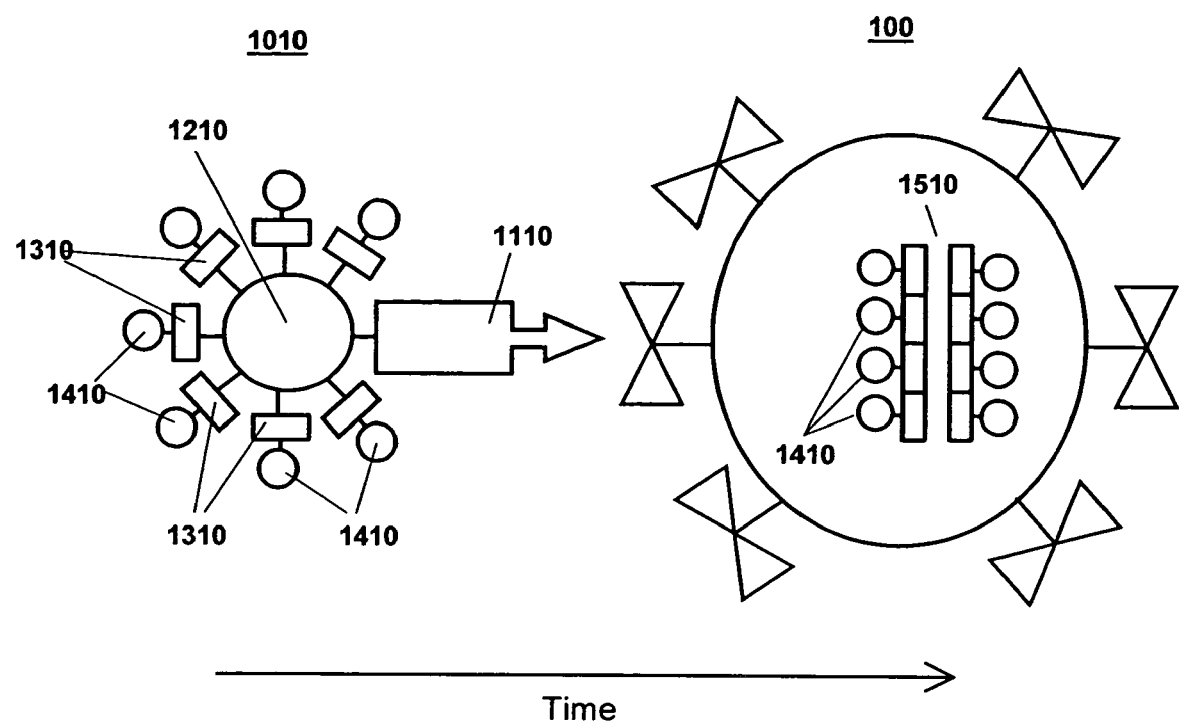
FIG. 6 is an illustration depicting the Step 1 Reagent for the first example of a Step 1 Reagent.

Synthesis of an
Anti-EGF-Antibody-Dextran-3-Indoxyl
Phosphate-Phosphoenol Pyruvate Conjugate A Step 1 Reagent is shown in FIG. 6. The cell targeting agent 1110, is a monoclonal antibody to the EGF receptor; the carrier moiety 1210, is the polysaccharide dextran; and the platform building material 1310, is a substituted 3-indoxyl phosphate derivative that has attached to it an additional molecular structure 1410 of a phosphoenol pyruvate derivative.

As shown in FIG. 6, the Step 1 Reagent 1010 forms the intracellular aqueous insoluble nano-platform 1510 by linking aggregates of indigo to form micro-precipitates. Some or all of the platform building materials include the additional molecular structure 1410, a derivative of phosphoenolpyruvate, which is an irreversible inhibitor of the enzyme UDP-N-acetylglucosamine enolpyruvoyltransferase that is the targeting moiety of the Step 3 Bispecific Reagent. The indoxyl phosphate platform building materials are linked to the targeting moiety by a dextran carrier moiety. The linker molecule is attached to the phosphate group of the indoxyl phosphate derivative platform building material so it does not interfere with the release of the indoxyl intermediates and their dimerization to form the indigo derivative intracellular aqueous insoluble nano-platform.

Figure 7:
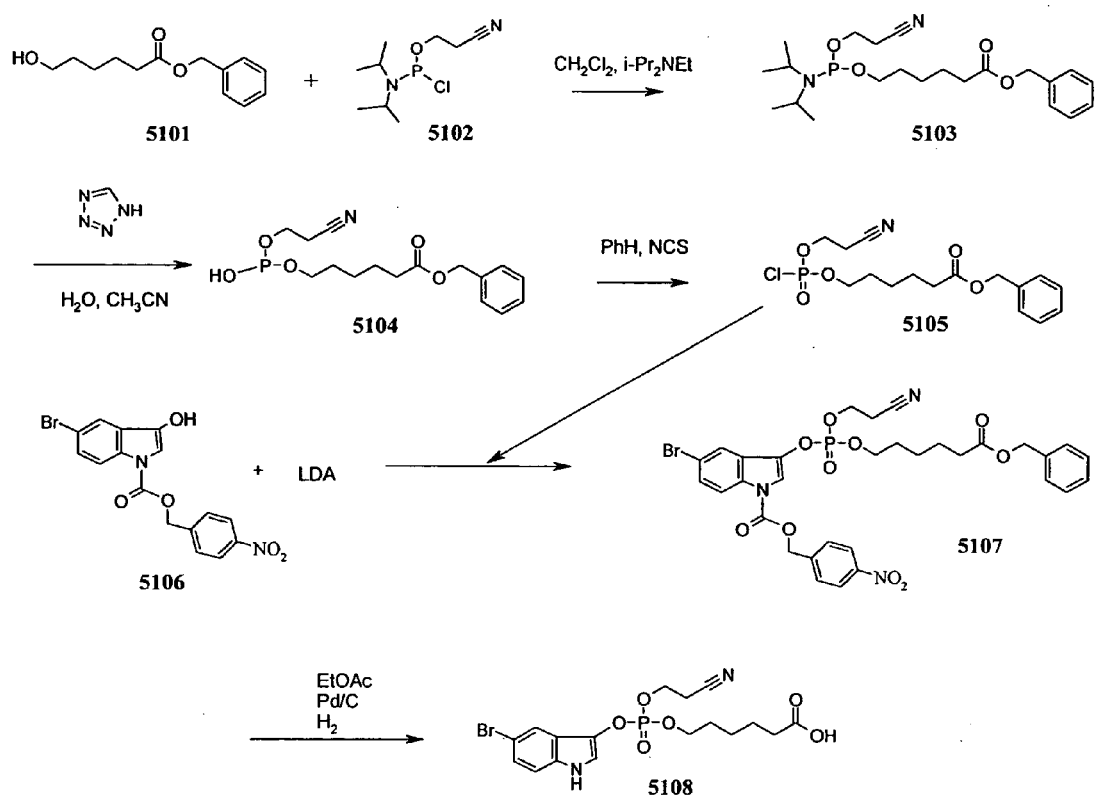
FIG. 7 is an illustration depicting the synthesis of Bromo-indoxyl phosphate with linker molecule.

Synthesis of the Step 1 Reagent proceeds in the following manner: As shown in FIG. 7, 2-cyanoethyl diisopropylchlorophosphoramidate 5102 was allowed to react with benzyl 6-hydroxyhexanoate 5101 in the presence of a tertiary amine in methylene chloride at 0° C. for 1½ hours and then at room temperature for ½ hour to yield 5103. Following hydrolysis of the diisopropylamine group on compound 5103 with 1H-tetrazole and water, the phosphite 5104 was oxidized with N-chlorosuccinimide in benzene for 15 hours at room temperature to generate the chlorophosphate 5105. The lithium salt of N-p-nitrobenzyloxycarbonyl-5-bromo-3-hydroxyindole 5106 was generated while the reaction mixture was cooled in a dry ice/acetone bath followed by the addition of 5105. The reaction mixture was allowed to slowly come to room temperature to yield 5-benzyloxycarbonylpentyl-2'-cyanoethyl-N-p-nitrobenzyloxycarbonyl-5''-bromo-3''-indolyl phosphate 5107. The benzyl and nitrobenzyl carbamate protecting groups were removed by catalytic hydrogenation using 10% palladium on charcoal and hydrogen at atmospheric pressure for 1 hour at room temperature to yield 5-carboxypentyl 2'-cyanoethyl 5''-bromo-3''-indolyl phosphate 5108.

Figure 8:
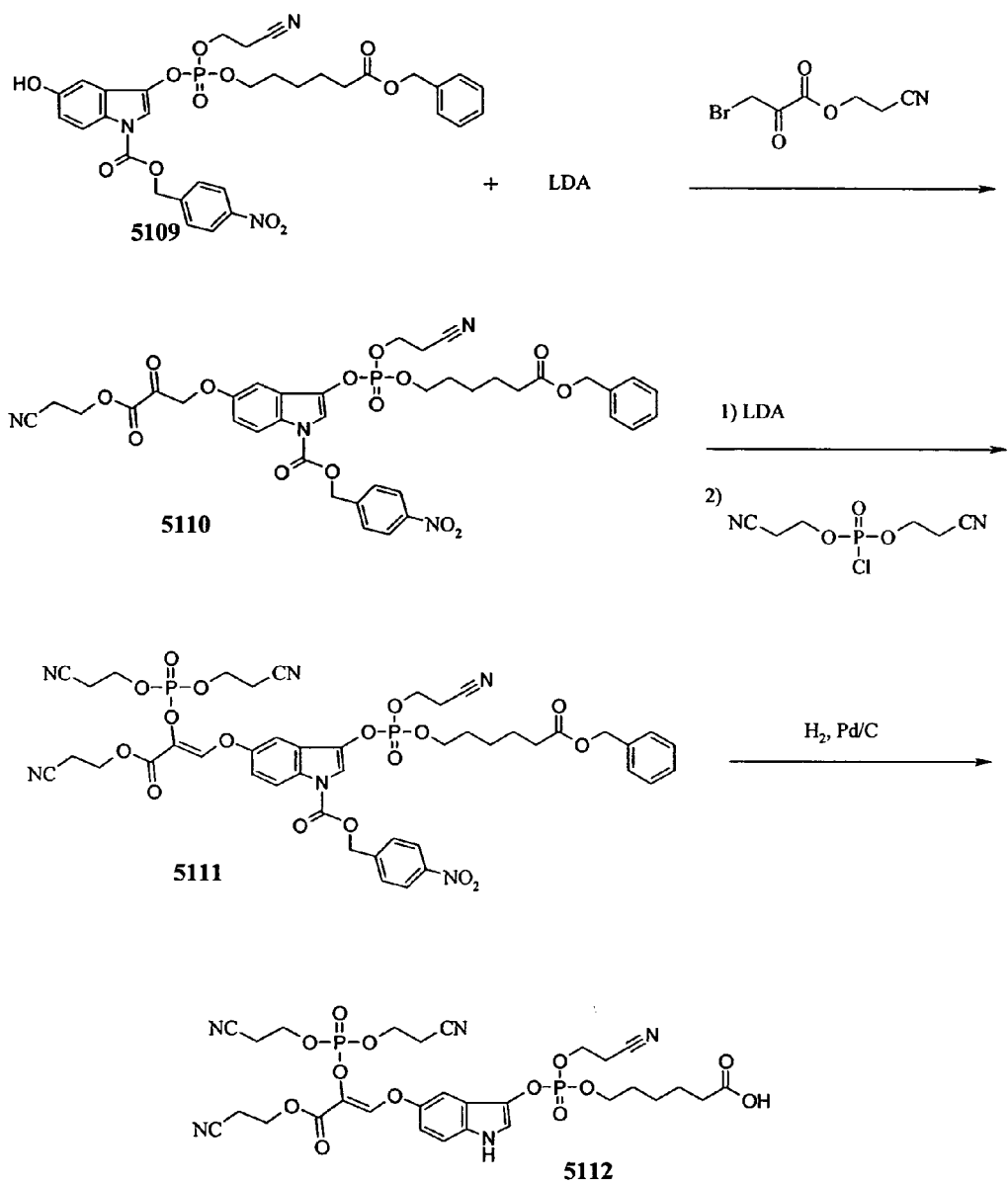
FIG. 8 is an illustration depicting the synthesis of platform building material with irreversible enzyme inhibitor for the first example of a Step 1 Reagent.

The additional molecular structure on the platform building material, a derivative of phosphoenolpyruvate, is an irreversible enzyme inhibitor which forms a covalent adduct with the enzyme UDP-N-acetylglucosamine enolpyruvoyltransferase (Schonbrunn, et al., Eur. J. Biochem. 253: 406-412, 1998; Samland, et al., Biochemistry 38: 13162-13169, 1999; Brown, et al., Biochemistry 33: 10638-10645, 1994), which is the targeting moiety of the subsequently administered Step 3 Bispecific Reagent. As shown in FIG. 8, when an analog of the indoxyl compound described above, 5-benzyloxycarbonylpentyl 2'-cyanoethyl N-p-nitrobenzyloxycarbonyl-5''-hydroxy-3''indolyl phosphate 5109, is allowed to react with lithium diisopropylamide in a dry ice/acetone bath, cyanoethyl 3-bromopyruvate is added and the reaction allowed to come to room temperature slowly to produce 5110. This product 5110 is then allowed to react with lithium diisopropylamide in a dry ice/acetone bath followed by biscyanoethylchlorophosphate to yield the protected phosphoenolpyruvate indoxyl phosphate derivative 5111. The nitrobenzyl carbamate and benzyl protecting groups are then removed by catalytic hydrogenation using 10% palladium on charcoal and hydrogen at atmospheric pressure for 1 hour at room temperature to make the protected platform building material with the irreversible enzyme inhibitor attached 5112.

Figure 9:
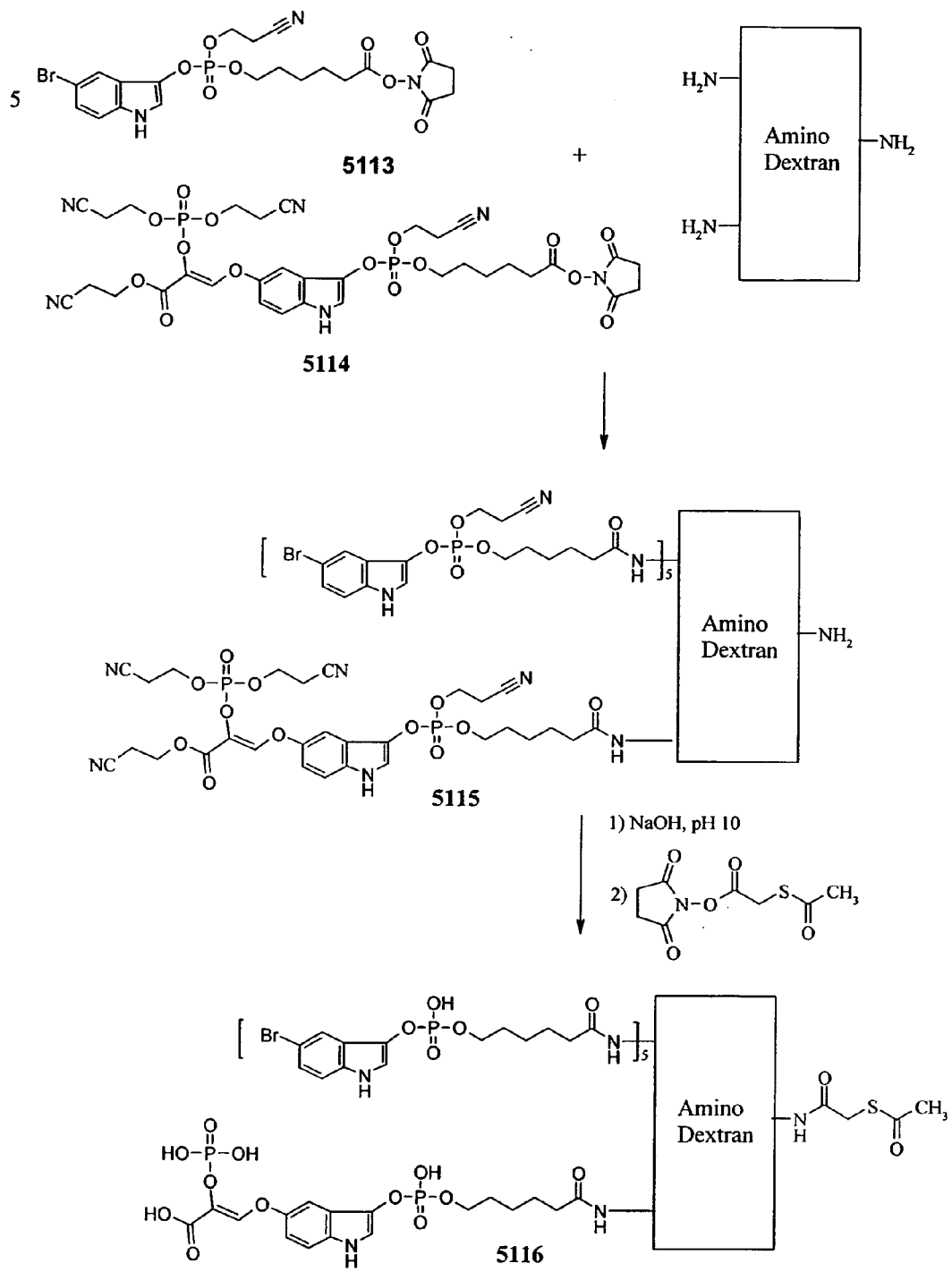
FIG. 9 is an illustration depicting conjugating the platform building materials for the first example of a Step 1 Reagent.
Figure 9B:
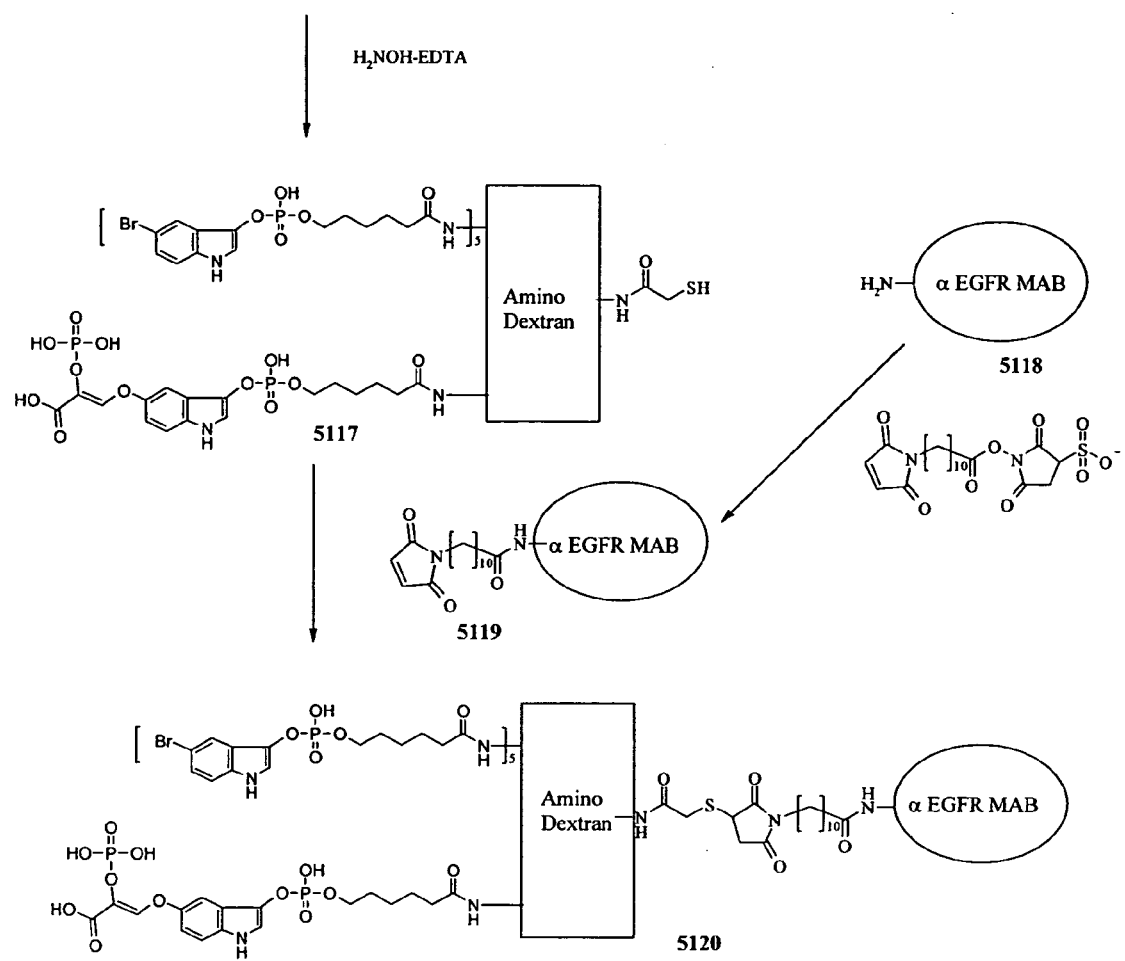
FIG. 9b Step 1 Reagent for the first example of a Step 1 Reagent.

Amino-Dextran was prepared from dextran following the procedure described by Kamizura, et al. (Invest. Ophthalmol. Vis. Sci. 42: 2664-2672, 2001). Dextran (64,000-76,000 MW, Sigma Chemical Co., St. Louis, Mo.) was dissolved in 4N sodium hydroxide and allowed to react with 6-bromohexanoic acid at 80° C. for 3 hours. Low molecular weight reagents were removed by dialysis and the solution was concentrated in vacuo. The carboxyl groups were activated by the addition of 1-ethyl-3-[3-(dimethylamino)propyl]carbodiimide and then a 15M excess of ethylenediamine over dextran was added stepwise and the reaction was allowed to proceed for 12 hours at room temperature in the dark. The pH of the solution was maintained between 5.0 and 5.5 with 0.1N hydrochloric acid throughout the procedure. The solution was dialyzed against 0.1M phosphate buffer (pH 7.4) and concentrated by ultrafiltration. The number of amino groups on Amino-Dextran was assayed by using trinitrobenzene sulfonic acid (Bubnis and Ofner, Anal. Biochem. 207: 129-133, 1992; Sashidhar, et al., J. Immunol. Methods 167: 121-127, 1994; Habeeb, Anal. Biochem. 47: 654-660, 1966). Based on the number of amino groups, 80% can be used for attaching indoxyl phosphate compounds. As shown in FIG. 9, a mixture of 4 parts 5-carboxypentyl 2'-cyanoethyl 5''-bromo-3''-indolyl phosphate and 1 part of 5-carboxypentyl 2'-cyanoethyl 5''-phosphoenolpyruvate-3''-indolyl phosphate (that is, one in five platform building materials has the additional molecular structure that is an irreversible enzyme inhibitor) is dissolved in DMSO and converted to the N-hydroxysuccinimide esters 5113 and 5114, respectively, by addition of N-hydroxysuccinimide and 1-ethyl-3-[3-(dimethylamino)propyl]carbodiimide at room temperature for 2 hours. The solution of the active esters is then added stepwise to the solution of Amino-Dextran while maintaining the pH of the reaction mixture between 7 and 8 with 1N sodium hydroxide over the period of an hour to yield 5115. Low molecular weight by-products are removed by exhaustive dialysis against phosphate buffered saline (pH 7.2). The pH of the solution is then raised to and maintained at 10 with 5N sodium hydroxide for 1 hour to effect removal of the cyanoethyl groups. The pH is lowered to 7.5 and some of the residual amino groups on the Amino-Dextran conjugate react with the N-hydroxysuccinimide ester of S-acetyl thioacetic acid. One hundred mg of N-hydroxysuccinimidyl S-acetylthioacetate is dissolved in DMSO and added stepwise to 1 gram of derivatized Amino-Dextran while maintaining the pH of the reaction mixture between 7 and 8 to yield 5116. Following the reaction, the sample is dialyzed against phosphate buffered saline (pH 7.2) overnight. As shown in FIG. 9b, fifty mg of the Dextran conjugate in 5 mL of phosphate buffered saline (pH 7.2) is mixed with 0.5 mL of hydroxylamine-EDTA solution (pH 7.4) and allowed to react for 2 hours to remove the acetyl group from S-acetyl thioacetyl side chain to yield 5117, providing free sulfhydryl groups for coupling with the heterobifunctional reagent on the anti-EGFR monoclonal antibody targeting agent. One hundred mg of Anti-EGFR monoclonal antibody 5118, dissolved in 8 mL of phosphate buffered saline (pH 7.4), is reacted with 5 mg of N-[κ-maleimidoundecanoyloxy] sulfosuccinimide ester for 30 min. at room temperature while maintaining the pH between 7 and 7.5 with 0.1N sodium hydroxide to yield 5119. The protein is separated from reactants by passage through a NAP25 column. The solution of 5119 is added to the solution of 5117 and diluted until the concentration of 5117 is 3 mg/mL. The reaction is allowed to proceed for 2 hours at room temperature to yield 5120 that is the Step 1 Reagent. The reaction mixture is dialyzed overnight against cold phosphate buffered saline (pH 7.2). The conjugate is evaluated on Sephacryl 300 chromatography. Similar preparations show 60-95% as protein-dextran conjugate 5120 based on absorption units at 280 nm.

Example 2

Synthesis of a Transferrin-Albumin-Bis-3-Indoxyl Glycoside-Loracarbef Conjugate

Figure 10:
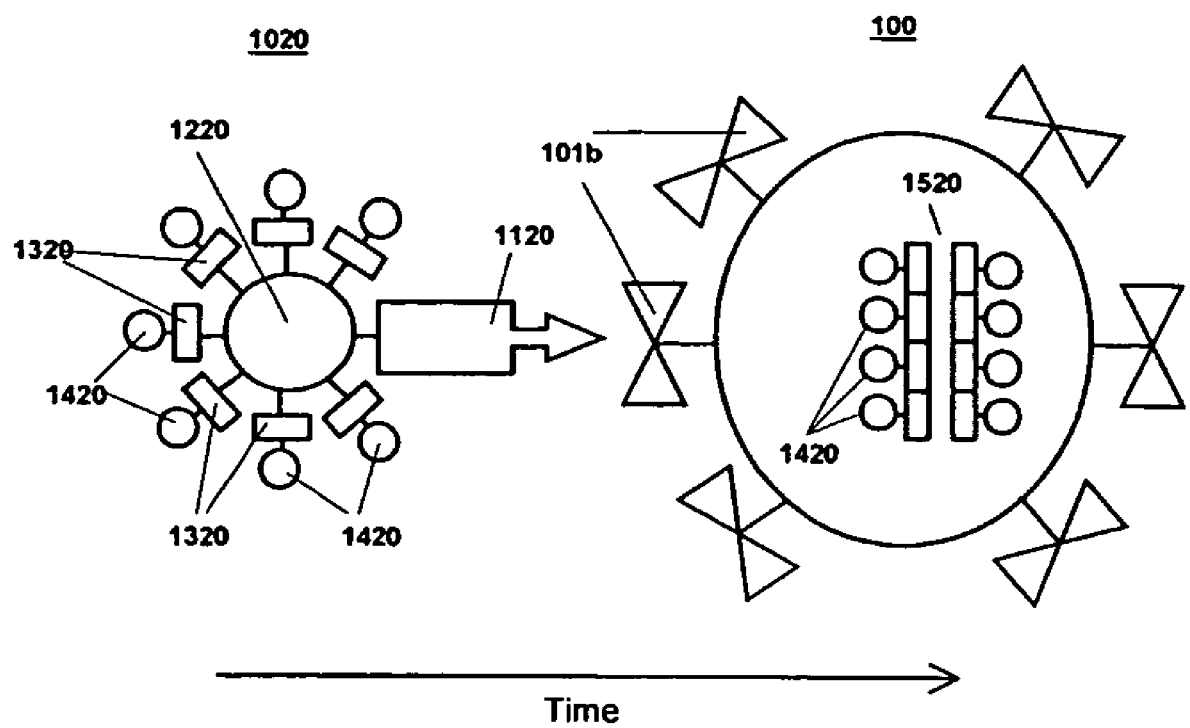
FIG. 10 is an illustration depicting the Step 1 Reagent for the second example.

A Step 1 Reagent is shown in FIG. 10. The cell targeting agent 1120, is human transferrin; the carrier moiety 1220, is human serum albumin; and the platform building material 1320, is a substituted bis-3-indoxyl glycoside (e.g., glucoside or galactoside) derivative that has attached to it an additional molecular structure 1420 of the carbacephem analog, Loracarbef.

Figure 11:
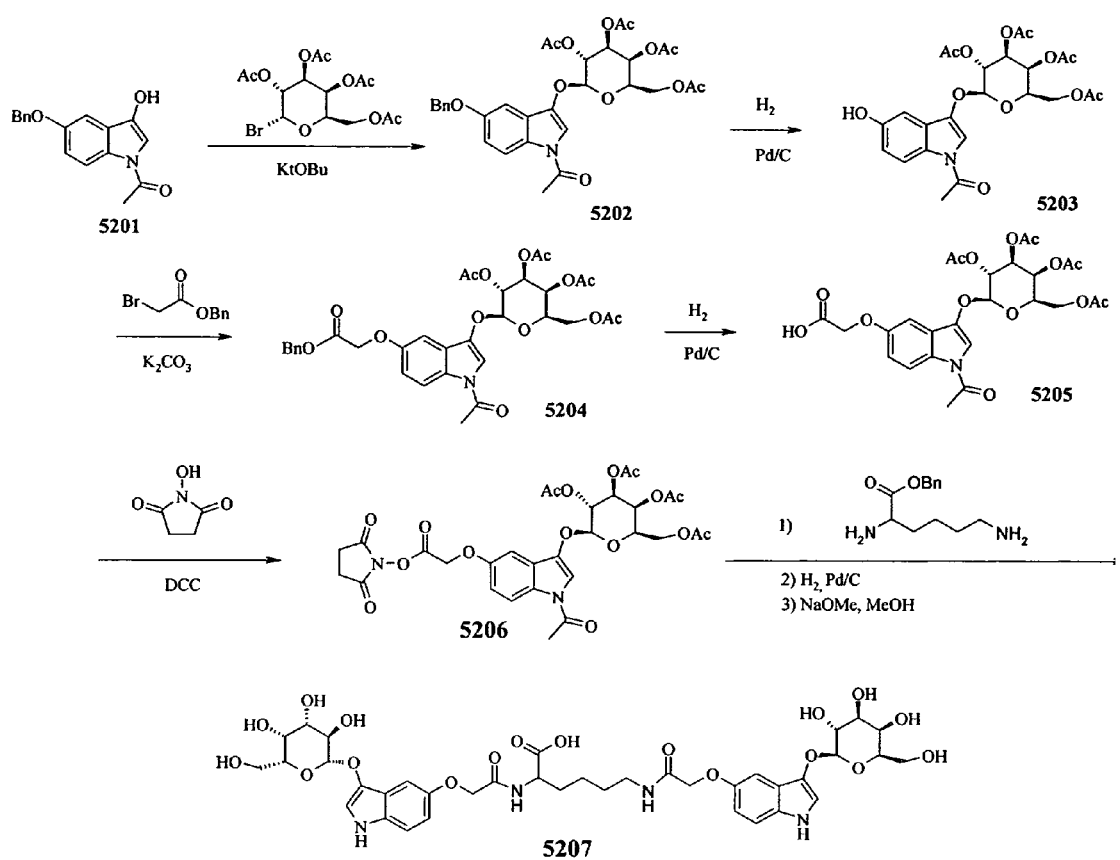
FIG. 11 is an illustration depicting the synthesis of Bis-indoxyl for the platform building materials for the second example of a Step 1 Reagent.

As further in FIG. 10, once inside the targeted cells, the Step 1 Reagent in the second example forms the intracellular aqueous insoluble nano-platform 1520 by linking aggregates of polyindigo to form micro-precipitates. The platform building materials are bisindoxyl lysine derivatives. Some or all of the platform building materials include the additional molecular structure 1420, a derivative of Loracarbef, which is an irreversible inhibitor of a mutant β-lactamase that is the targeting moiety of the Step 3 Bispecific Reagent. These bisindoxyl lysine platform building materials are attached to amino groups on the carrier moiety 1220, human serum albumin, via the carboxyl group in the amino acid backbone of the platform building materials (lysine or lysylglutamic acid). The targeting agent 1120, human transferrin, which binds to the transferrin receptor 101b on the cancer cells 100, is attached to the human serum albumin carrier moiety complex via a heterobifunctional linker molecule. In this example the polymerizing group of the platform building materials is an indoxyl glycoside and the linkage to the lysine is through a substituent in the 5 position on the indoxyl ring. Synthesis of this second example of a Step 1 Reagent can proceed in the following manner: As shown in FIG. 11, N-acetyl-5-benzyloxy-1,2-dihydro-3H-indol-3-one 5201 dissolved in acetonitrile was allowed to react with potassium t-butoxide at 0° C. for 1 hour, and then acetobromogalactose or acetobromoglucose dissolved in acetonitrile was added and allowed to react for 4 hours at 0° C. to yield the 1-acetyl-3-(2',3',4',6'-tetra-O-acetyl-β-D-galactosidoxy)-5-benzyloxyindole 5202 or 1-acetyl-3-(2',3',4',6',-tetra-O-acetyl-β-glucosidoxy)-5-benzyloxyindole. The benzyl group was removed by catalytic hydrogenation using 10% palladium on charcoal and hydrogen at atmospheric pressure to yield 5203. The free hydroxyl group on 5203 was allowed to react with benzyl bromoacetate to yield 5204. The benzyl group was removed by catalytic hydrogenation using 10% palladium on charcoal to yield 5205, and then the carboxyl group was converted to an active ester with N-hydroxysuccinimide and dicyclohexylcarbodiimide to yield 5206. The active ester compound 5206 was allowed to react with each of the amino groups on benzyl-L-lysine to yield the benzyl ester of bispentaacetylindoxylgalactoside-L-lysine or bispentaacetylindoxylglucoside-L-lysine. The benzyl protecting group was removed by catalytic hydrogenation using 10% palladium on charcoal and hydrogen at atmospheric pressure. The acetyl protecting groups were removed by transesterification with sodium methoxide in methanol to yield the bisindoxylgalactosyl-L-lysine 5207 or bisindoxylglucosyl-L-lysine.

Figure 12:
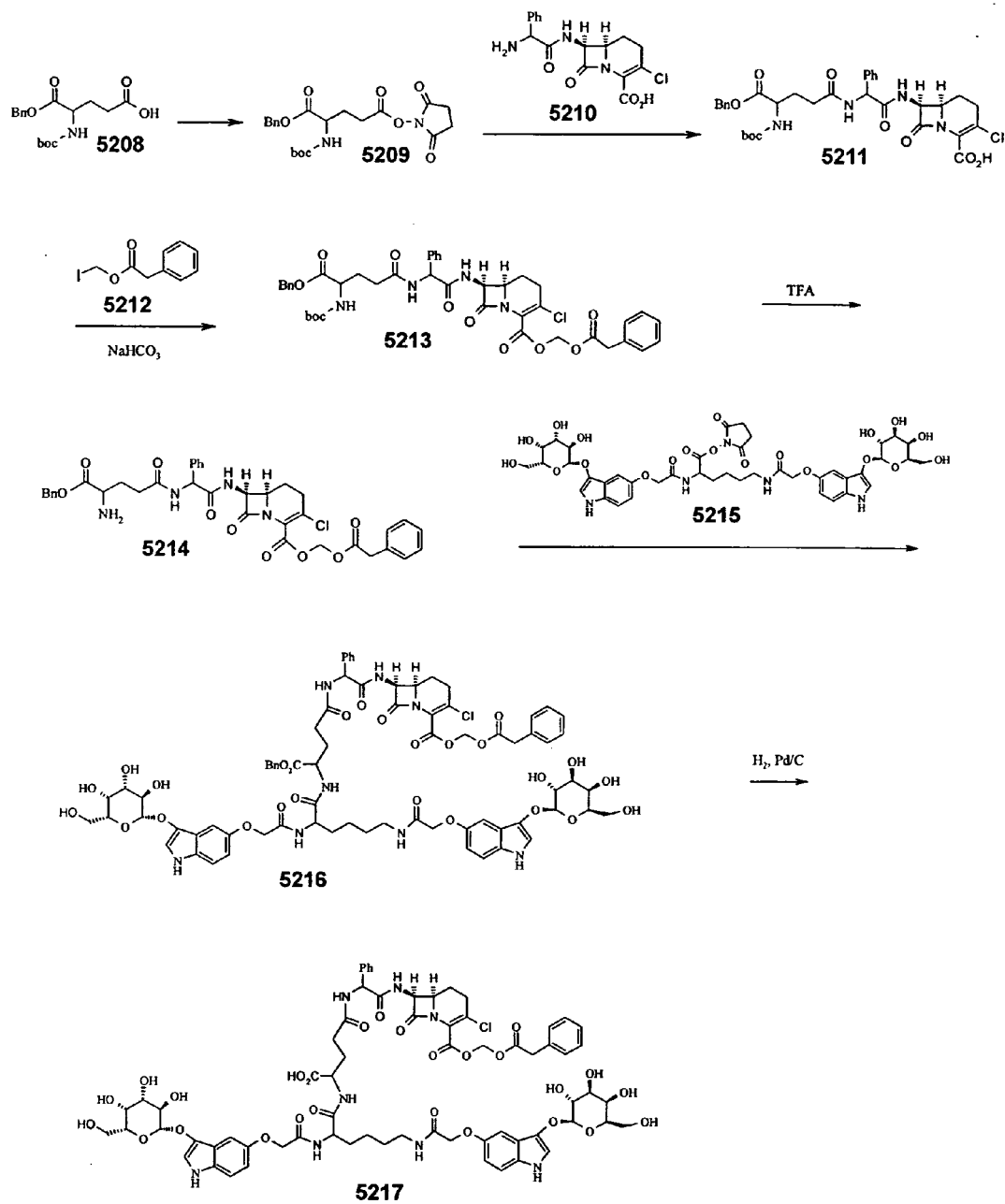
FIG. 12 is an illustration depicting the synthesis of platform building material with irreversible enzyme inhibitor for the second example of a Step 1 Reagent.

As shown in FIG. 12, the irreversible enzyme inhibitor used as the additional molecular structure on the platform building material is the antibiotic Loracarbef 5210. Loracarbef 5210 was first allowed to react with Nα-BOC-Oα-benzyl-Oγ-N-hydroxysuccinimidyl glutamate 5209 that had been prepared from the protected glutamic acid 5208 to yield the Loracarbef-glutamate conjugate 5211. The carboxyl group on the Loracarbef-glutamate conjugate 5211 was protected as the phenyl acetoxy methyl ester 5213 using phenyl acetoxy methyl iodide 5212. The BOC protecting group was removed by trifluoroacetic acid to yield the phenyl acetoxy methyl ester 5214. This derivative of Loracarbef 5214 was allowed to react with the active ester of bisindoxylgalactosyl lysine 5215 or bisindoxylglucosyl-L-lysine, which had been prepared from reaction of (5207, FIG. 11) with N-hydroxysuccinimide and dicyclohexylcarbodiimide, to yield the Loracarbef-bisindoxylgalactosyl lysine derivative 5216 or Loracarbef-bisindoxylglucosyl lysine derivative. The benzyl group was removed by catalytic hydrogenation with 10% palladium on charcoal and hydrogen at atmospheric pressure to yield 5217, which is the platform building material with the irreversible enzyme inhibitor prepared for coupling to the carrier moiety.

Figure 13:
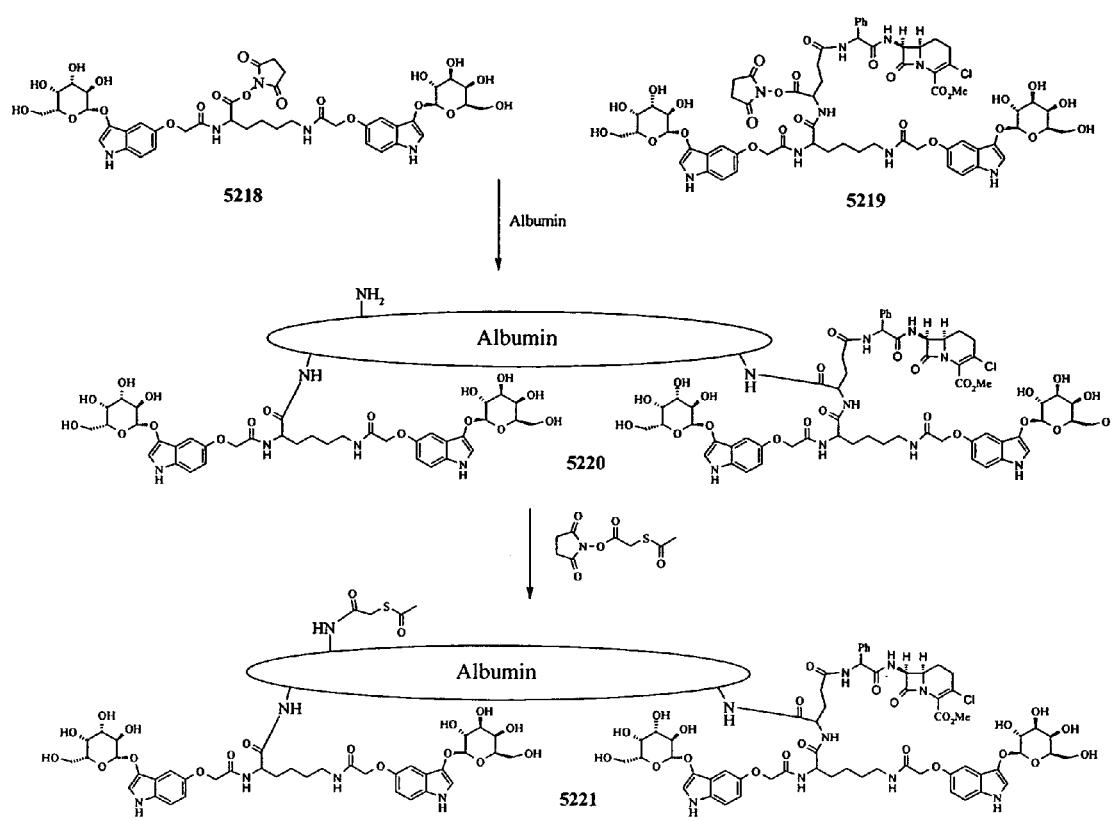
FIG. 13 is an illustration depicting conjugating the platform building materials for the second example of a Step 1 Reagent.
Figure 13B:
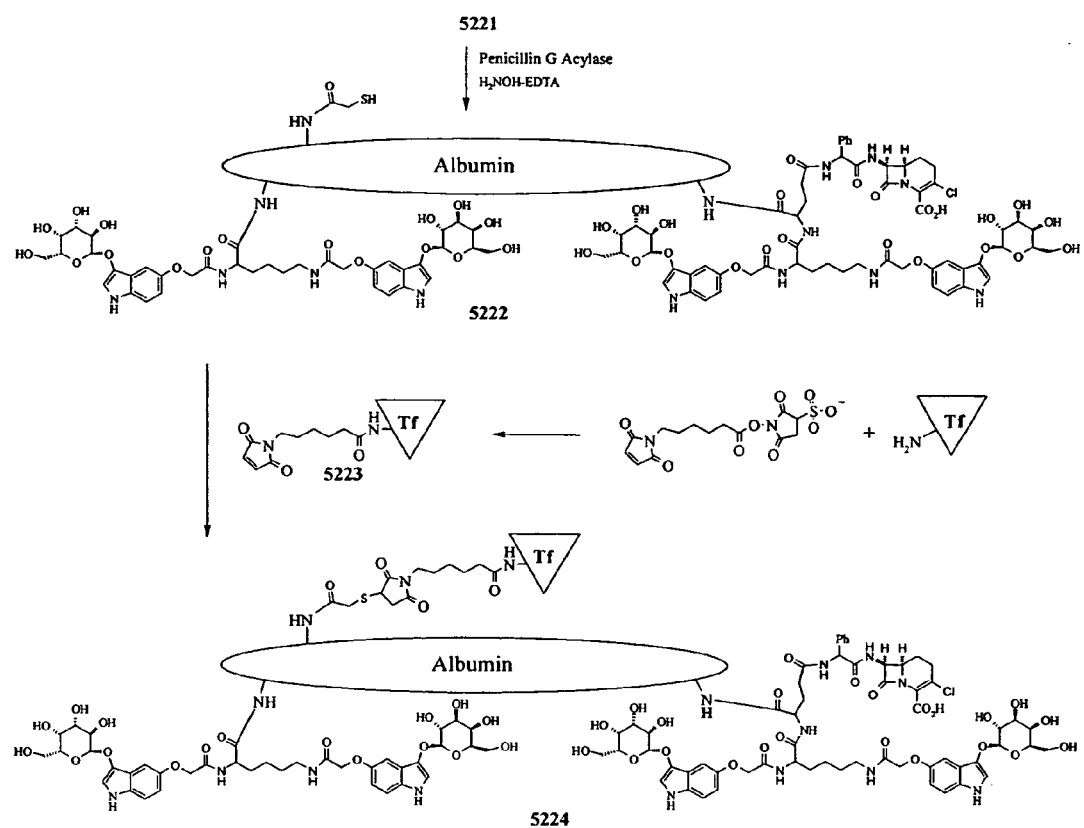
FIG. 13b Step 1 Reagent for the second example of a Step 1 Reagent.

Multiple platform building materials were attached to the carrier moiety (human serum albumin), as shown in FIG. 13, to increase the delivery of the platform building materials to the tumors. It was determined that only one Loracarbef binding site would be needed for every fifth indigo unit on the resulting indigo polymer aqueous insoluble nano-platform, so the platform building materials were attached to the albumin carrier moiety in a ratio of 4 (bisindoxylgalactosyl-L-lysines) to 1 (Loracarbef-bisindoxylgalactosyl-L-lysine derivative). Similar conjugates have been prepared with the glucoside derivatives. As shown in FIG. 13, the two platform building materials totaling an amount capable of modifying 80% of the amino groups on the human serum albumin carrier moiety were mixed in the ratio of 4 to 1, dissolved in DMSO, and activated by the addition of N-hydroxysuccinimide and 1-ethyl-3-[3-(dimethylamino)propyl]carbodiimide, which was allowed to proceed for 2-4 hours at room temperature to yield 5218 and 5219, respectively. A solution of human serum albumin (20 mg/mL in phosphate buffered saline pH 7.4) was maintained between pH 7 and 8 with 1N sodium hydroxide during the stepwise addition of the active ester solution of the two platform building materials 5218 and 5219. After the addition, the reaction was continued for an additional hour at room temperature. Conjugates have also been prepared using the active ester of a Loracarbef-lysyl-bisindoxylgalactosyl-L-lysine derivative to modify 80% of the amino groups on albumin. Reaction by-products were removed by exhaustive dialysis against phosphate buffered saline (pH 7.2) to yield a solution of the human serum albumin carrier moiety-platform building material complex 5220. A similar carrier conjugate has been made with the Loracarbef-lysyl-bisindoxylglucosyl-L-lysine derivative. Twenty-five mg of N-hydroxysuccinimidyl S-acetylthioacetate were dissolved in DMSO and added stepwise to the solution of the albumin complex while maintaining the pH between 7 and 8 with 0.5N sodium hydroxide. Following reaction, the solution was dialyzed overnight against phosphate buffered saline (pH 7.2) to yield a solution of 5221.

Following dialysis, 1000 units of penicillin G acylase were added and the solution was incubated at 37° C. overnight to remove the phenyl acetoxy methyl protecting group from the Loracarbef side chains (additional molecular structures). The acetyl group was removed from the S-acetyl thioacetyl side chain by the addition of hydroxylamine at room temperature to yield 5222, which provides free sulfhydryl groups for coupling with the heterobifunctional reagent on the human transferrin cell targeting agent. Human transferrin (200 mg) was dissolved in 8 mL of phosphate buffered saline (pH 7.2) and allowed to react with N-(ε-maleimidocaproyloxy) sulfosuccinimide ester (12 mg) while maintaining the pH between 7.0 and 7.5. After 30 minutes, the modified human transferrin 5223 was separated from the reactants using a NAP25 column. The human transferrin with maleimidyl groups 5223 was mixed with the albumin-platform building materials complex 5222 at a final dilution of 3 mg/mL for each protein. After allowing the proteins to form a conjugate 5224 that is the Step 1 Reagent for 2 hours at room temperature, the protein solution was dialyzed against phosphate buffered saline at 4° C. overnight. The Step 1 Reagent 5224 was characterized by chromatography on Sephacryl 200 (Pharmacia, Inc. Piscataway, N.J.). Typically 90-95% of the transferrin and albumin have become conjugated as estimated from the peak absorption at 280 nm. A Step 1 Reagent with the indoxyl glucoside derivative has also been prepared.

Example 3

Figure 14:
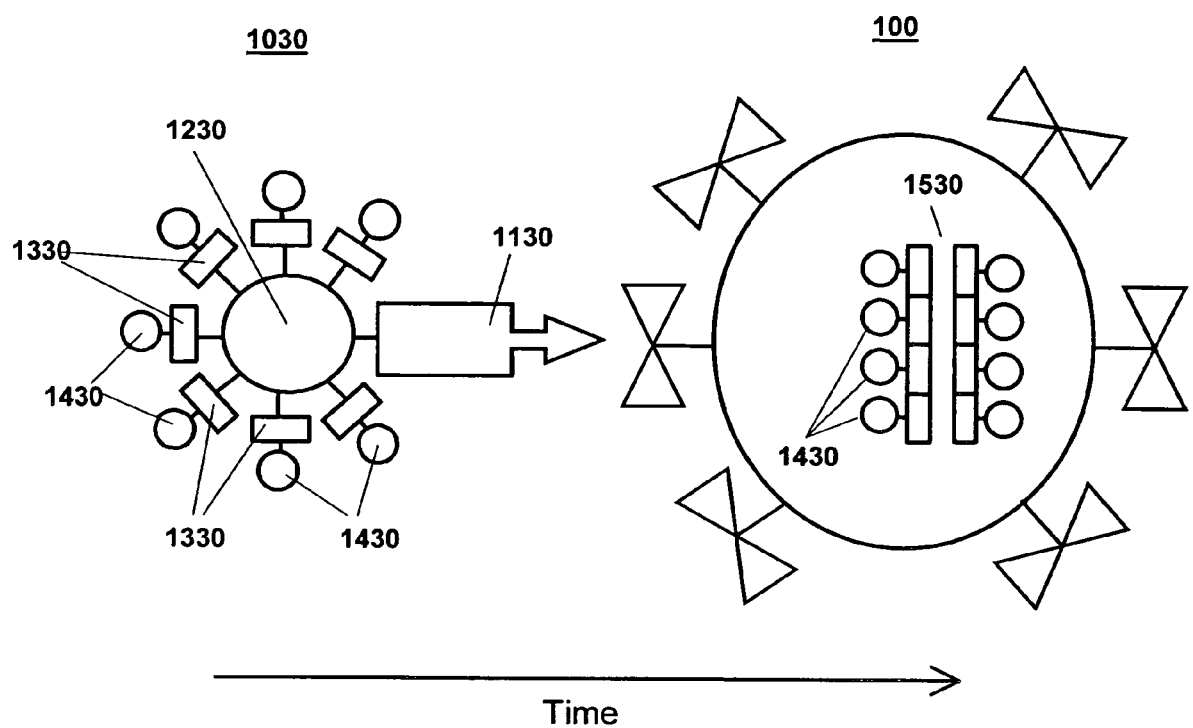
FIG. 14 is an illustration depicting the Step 1 Reagent for the third example of a Step 1 Reagent.

Synthesis of a Folate-Immunoglobulin-Porphyrin-α-Difluoromethylornithine Conjugate A Step 1 Reagent is shown in FIG. 14. In this example, the Step 1 Reagent 1030 is comprised of a cell targeting agent 1130, which is a folate derivative; a carrier moiety 1230, which is human immunoglobulin; a platform building material 1330, which is an appropriate porphyrin derivative that has attached to it an additional molecular structure 1430 that is an α-difluoromethylornithine analog (Metcalf, et al., J. Am. Chem. Soc. 100: 2551-2553, 1978), which is an irreversible inhibitor for the enzyme ornithine decarboxylase. Alternatively, a similar system would use an additional molecular structure that is α-difluoromethylarginine, which is an irreversible inhibitor for the enzyme arginine decarboxylase.

As shown in FIG. 14, the Step 1 Reagent forms the intracellular aqueous insoluble nano-platform 1530 by the aggregation of porphyrin platform building materials released from the Step 1 Reagent. The platform building materials are porphyrin derivatives. Some or all of the platform building materials include the additional molecular structure 1430, an α-difluoromethylornithine analog (Metcalf, et al., J. Am. Chem. Soc. 100: 2551-2553, 1978), which is an irreversible inhibitor of the enzyme ornithine decarboxylase that is the targeting moiety of the Step 3 Bispecific Reagent. These porphyrin derivative platform building materials are attached to a carrier moiety, human immunoglobulin, which is attached to the cell targeting agent that is folic acid.

Figure 15:
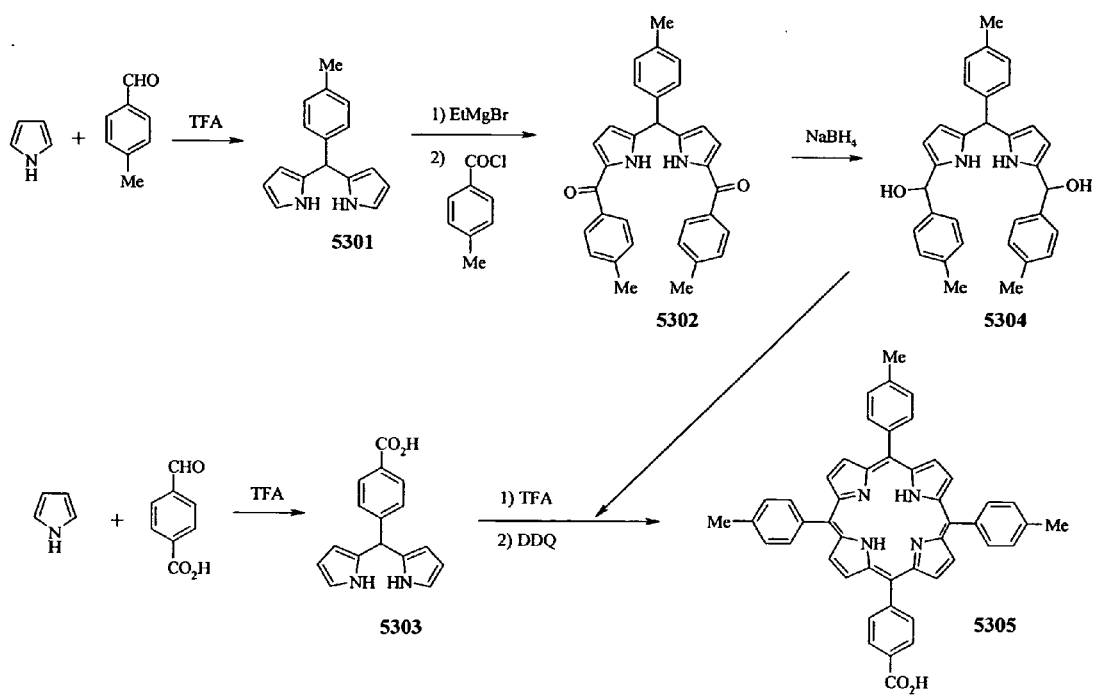
FIG. 15 is an illustration depicting the synthesis of a porphyrin-derivative for the platform building materials for the third example of a Step 1 Reagent.

Synthesis of the Step 1 Reagent proceeds in the following manner: As shown in FIG. 15, the synthesis of porphyrin derivatives follows procedures outlined by J. Lindsey and his colleagues (Littler, et al., J. Org. Chem. 64: 1391-1396, 1999; Rao, et al., J. Org. Chem. 65: 7323-7344, 2000). Experience has shown that a mixture of pyrrole and 4-methylbenzaldehyde can react with trifluoroacetic acid under an atmosphere of argon to yield 5-(4-methylphenyl) dipyrromethane 5301. A solution of ethyl magnesium bromide is slowly added to a cooled solution of 5-(4-methylphenyl) dipyrromethane 5301 in toluene, and after reaction for an additional 30 minutes, a solution of p-toluoyl chloride in toluene is added over 10 minutes to yield 1,9-Bis(4-methylbenzoyl)-5-(4-methylphenyl) dipyrromethane 5302. Using a similar reaction to the one described above, a mixture of pyrrole and 4-carboxybenzaldehyde can react with trifluoroacetic acid to yield 5-(4-carboxyphenyl) dipyrromethane 5303. Small amounts of sodium borohydride are added stepwise to a solution of 1,9-Bis(4-methylbenzoyl)-5-(4-methylphenyl) dipyrromethane 5302 in tetrahydrofuran/methanol (3:1) to produce the dicarbinol 5304. The dicarbinol 5304 and 5-(4-carboxyphenyl) dipyrromethane 5303 in equimolar amounts are dissolved in acetonitrile and allowed to react with trifluoroacetic acid for 5 minutes followed by oxidation with 2,3-dichloro-5,6-dicyano-1,4-benzoquinone (DDQ) to yield 5-(4-carboxyphenyl)-10,15,20-tris(4-methylphenyl) porphyrin 5305.

Figure 16:
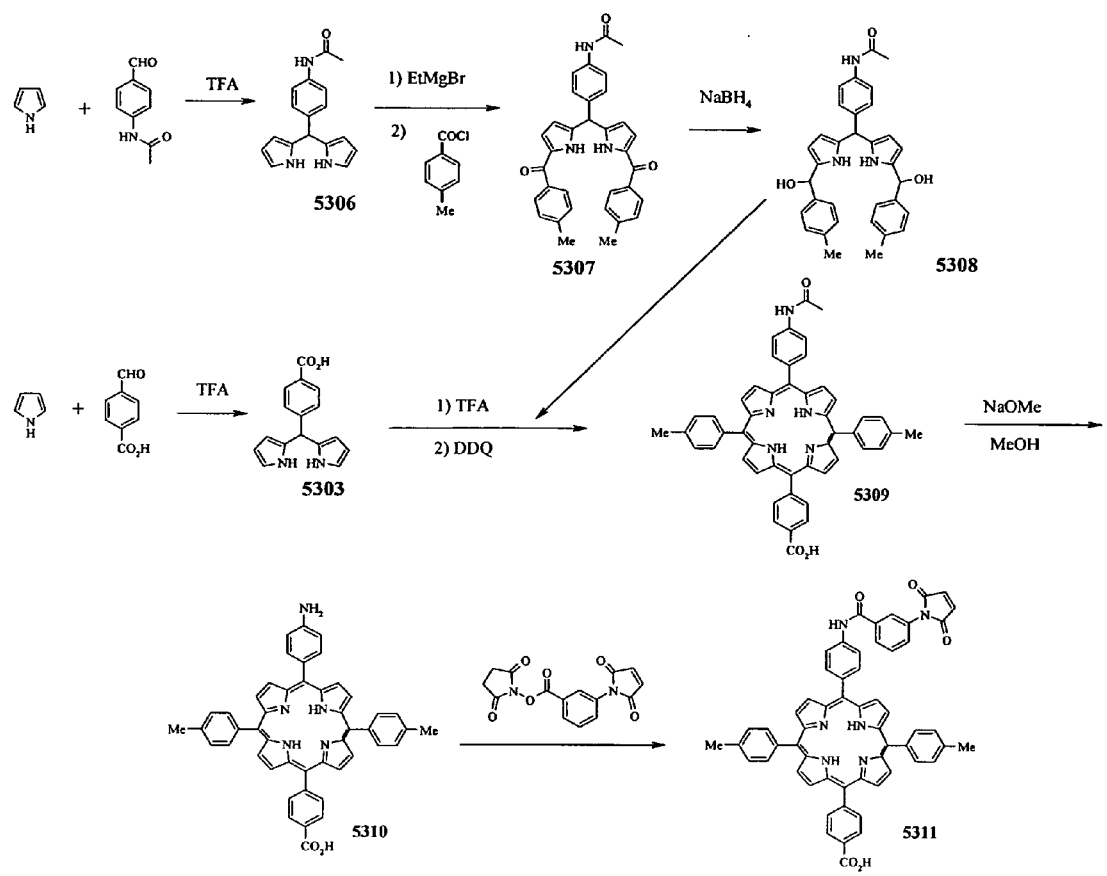
FIG. 16 is an illustration depicting the synthesis of platform building material with irreversible enzyme inhibitor for the third example of a Step 1 Reagent.

A second porphyrin derivative is developed with an additional functional group for attaching the irreversible enzyme inhibitor as the additional molecular structure for binding to the Step 3 Bispecific Reagent. As shown in FIG. 16, a mixture of pyrrole and 4-acetamidobenzaldehyde is allowed to react with trifluoroacetic acid under an atmosphere of argon to yield 5-(4-acetamidophenyl) dipyrromethane 5306. A solution of ethyl magnesium bromide is slowly added to a cooled solution of 5-(4-acetamidophenyl) dipyrromethane 5306 in toluene, and after reaction for an additional 30 minutes, a solution of p-toluoyl chloride in toluene is added over 10 minutes to yield 1,9-Bis(4-methylbenzoyl)-5-(4-acetamidophenyl) dipyrromethane 5307. Small amounts of sodium borohydride are added stepwise to a solution of 1,9-Bis(4-methylbenzoyl)-5-(4-acetamidophenyl) dipyrromethane 5307 in tetrahydrofuran/methanol (3:1) to produce the dicarbinol 5308. The dicarbinol 5308 and 5-(4-carboxyphenyl) dipyrromethane 5303 (the synthesis of which is described above) in equimolar amounts are dissolved in acetonitrile and allowed to react with trifluoroacetic acid for 5 minutes, followed by oxidation with DDQ to yield 5-(4-acetamidophenyl)-10,20-bis(4-methylphenyl)-15-(4-carboxyphenyl) porphyrin 5309. The acetyl protecting group is removed by using sodium methoxide in methanol to yield 5310, which is allowed to react with m-maleimidobenzoyl-N-hydroxysuccinimide ester to yield the maleimidyl substituted porphyrin 5311, providing an appropriate side chain for attaching the irreversible enzyme inhibitor, an α-difluoromethylornithine analog, after the folic acid-human immunoglobulin-porphyrin conjugate has been prepared.

Figure 17:
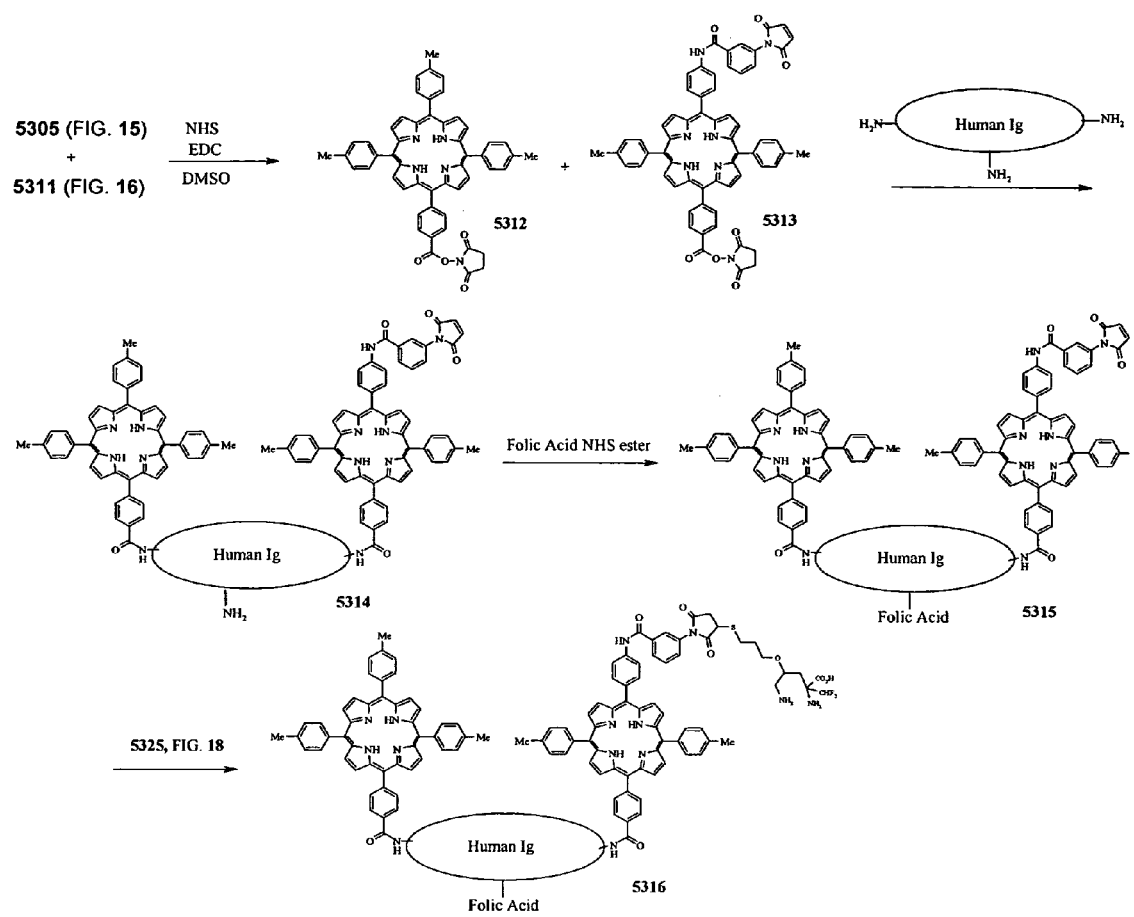
FIG. 17 is an illustration depicting the Step 1 Reagent for the third example of a Step 1 Reagent.

As shown in FIG. 17, a mixture of the porphyrin derivatives, 4 parts of 5-(4-carboxyphenyl)-10,15,20-tris(4-methylphenyl) porphyrin 5305, FIG. 15, and 1 part of the maleimidyl porphyrin derivative 5311, FIG. 16, is dissolved in DMSO and converted to the respective active esters 5312 and 5313 using N-hydroxysuccinimide and 1-ethyl-3-[3-(dimethylamino)propyl]carbodiimide. Human immunoglobulin is dissolved in phosphate buffered saline (10 mg/mL) and then the active ester solution of 5312 and 5313, using a total of 56 moles of active esters per mole of protein, is added stepwise over a period of one hour while maintaining the pH between 7 and 8 with 1N sodium hydroxide to yield the porphyrin-immunoglobulin conjugate 5314. Folic acid is converted to an active ester by dissolving in dimethyl sulfoxide and incubating with N-hydroxysuccinimide and 1-ethyl-3-[3-(dimethylamino)propyl]carbodiimide for 1 hour at room temperature. A 30-fold molar excess of the active ester solution (Laemon and Low, Proc. Natl. Sci. USA 88: 5572-5576, 1991) is added to the porphyrin-immunoglobulin conjugate 5314 stepwise while maintaining the pH between 7 and 8 with 1 N sodium hydroxide over a period of an hour at room temperature to yield a folic acid-immunoglobulin-porphyrin conjugate 5315. Unconjugated material and reagents are removed by dialysis against phosphate buffered saline (pH 6.0). The maleimido group on the porphyrin of the folic acid-immunoglobulin-porphyrin conjugate 5315 reacts with the mercapto derivative of α-difluoromethylornithine 5325, FIG. 18, the synthesis of which is described below, to yield the folate-targeted porphyrin-carrying immunoglobulin with attached irreversible enzyme inhibitor (additional molecular structure) 5316, which is the Step 1 Reagent ready for infusion into a tumor-bearing host.

Figure 18:
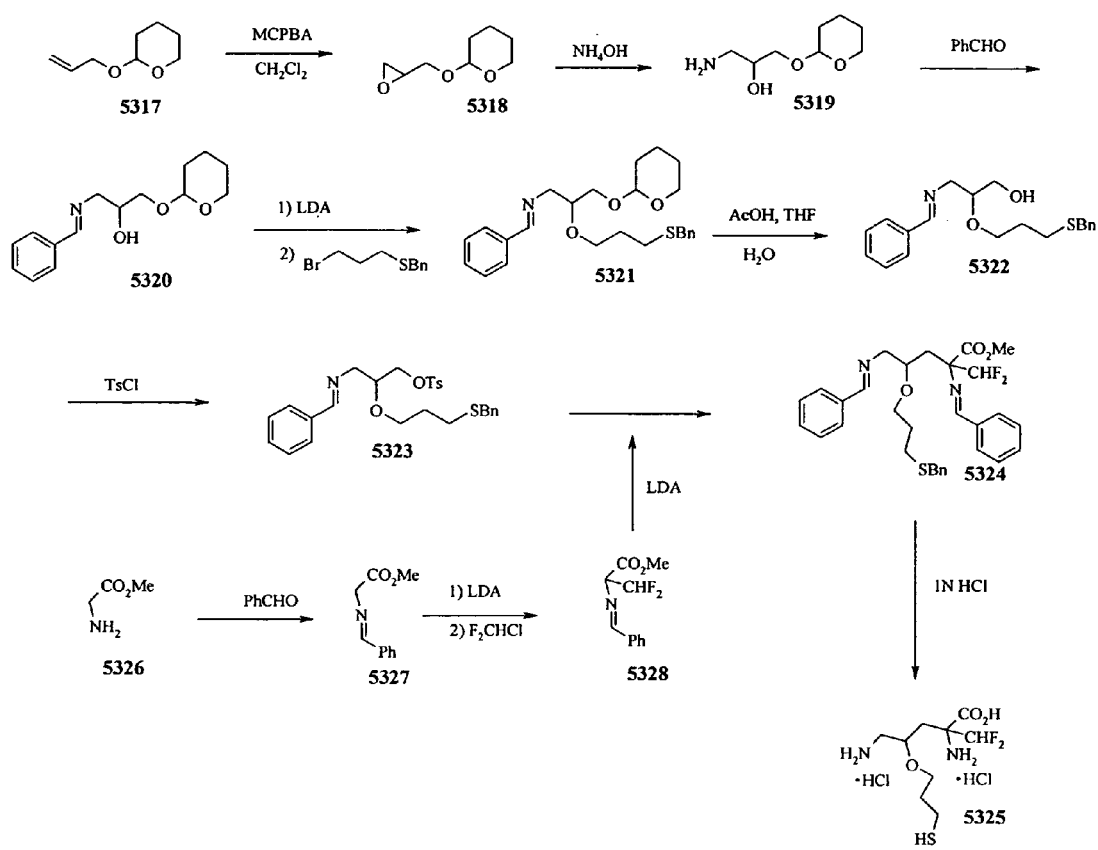
FIG. 18 is an illustration depicting the synthesis of irreversible enzyme inhibitor derivative for the third example of a Step 1 Reagent.

The mercapto derivative of α-difluoromethylornithine is prepared as shown in FIG. 18 as follows: The tetrahydropyranyl ether of allyl alcohol 5317 can be oxidized to the epoxide 5318 using m-chloroperbenzoic acid. The epoxide ring is opened with ammonium hydroxide to yield the amino alcohol derivative 5319, the amino group on which can then be protected by forming a Schiff base with benzaldehyde to yield 5320. The hydroxyl group on 5320 reacts with lithium diisopropylamide while being cooled in a dry ice/acetone bath followed by the addition of S-benzyl-n-propylbromide to yield 5321. The tetrahydropyranyl group is hydrolyzed with acetic acid and water to yield 5322, and then the hydroxyl group is converted to the tosyl derivative 5323 using tosyl chloride. The amino group on methyl glycine 5326 is protected as a Schiff base using benzaldehyde to yield 5327, which is then treated with lithium diisopropylamide cooled in a dry ice/acetone bath followed by reaction with chlorodifluoromethane to yield the protected difluoromethyl derivative of glycine 5328. The difluoromethyl derivative 5328 reacts with lithium diisopropylamide while being cooled in a dry ice/acetone bath followed by addition of the tosyl derivative 5323 to yield the protected ornithine derivative 5324. The protected α-difluoromethylornithine 5324 is deprotected by hydrolysis with 1N hydrochloric acid to yield the ornithine derivative with a mercapto side chain 5325.

Example 4

Synthesis of a Folate-Bis-3-Indoxyl Galactoside-Loracarbef Conjugate

Figure 19:
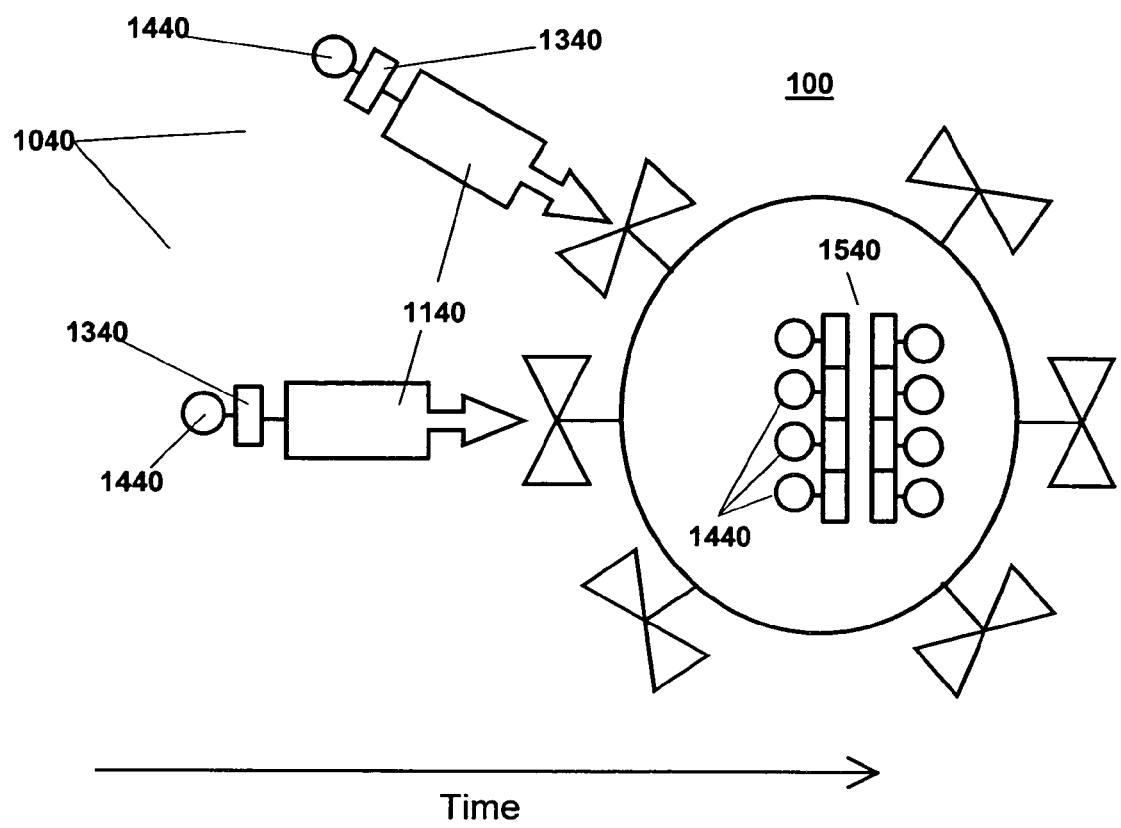
FIG. 19 is an illustration depicting the Step 1 Reagent for the fourth example of a Step 1 Reagent.

An example of a Step 1 Reagent is shown in FIG. 19. The Step 1 Reagent 1040 is comprised of a cell targeting agent 1140, which is a folate derivative, and a platform building material 1340, which is a substituted bis-3-indoxyl galactoside derivative that has attached to it an additional molecular structure 1440 that is the carbacephem analog, Loracarbef, which is an irreversible inhibitor for a mutant β-lactamase. The platform building material is attached directly to the cell targeting agent, providing a low molecular weight Step 1 Reagent that has improved biodistribution, circulation, and tumor penetration, and is small enough to reduce potential immunogenicity.

Figure 20:
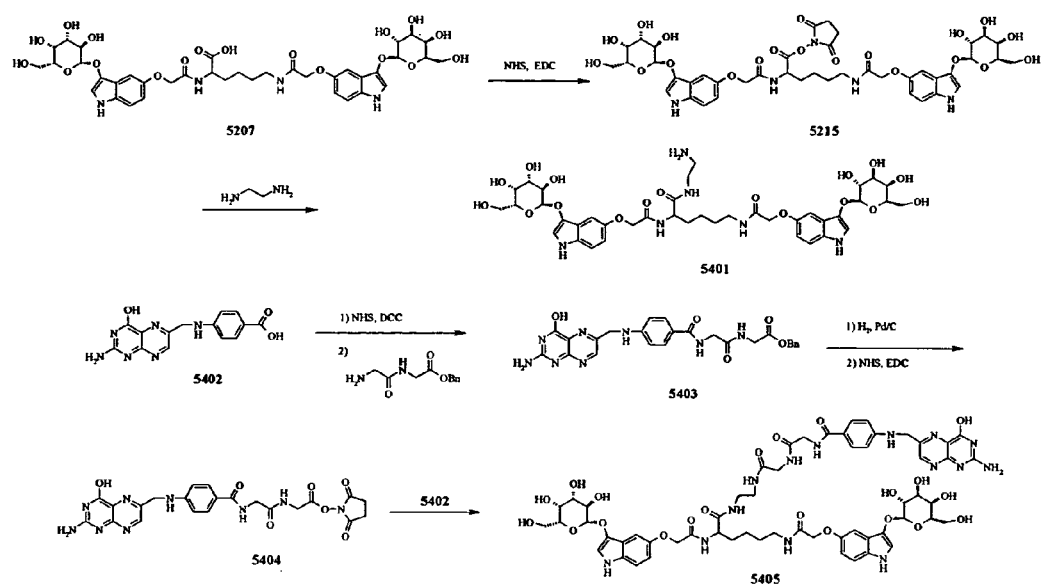
FIG. 20 is an illustration depicting the synthesis of the platform building materials with cell targeting agent attached for the fourth example of a Step 1 Reagent.
Figure 21:
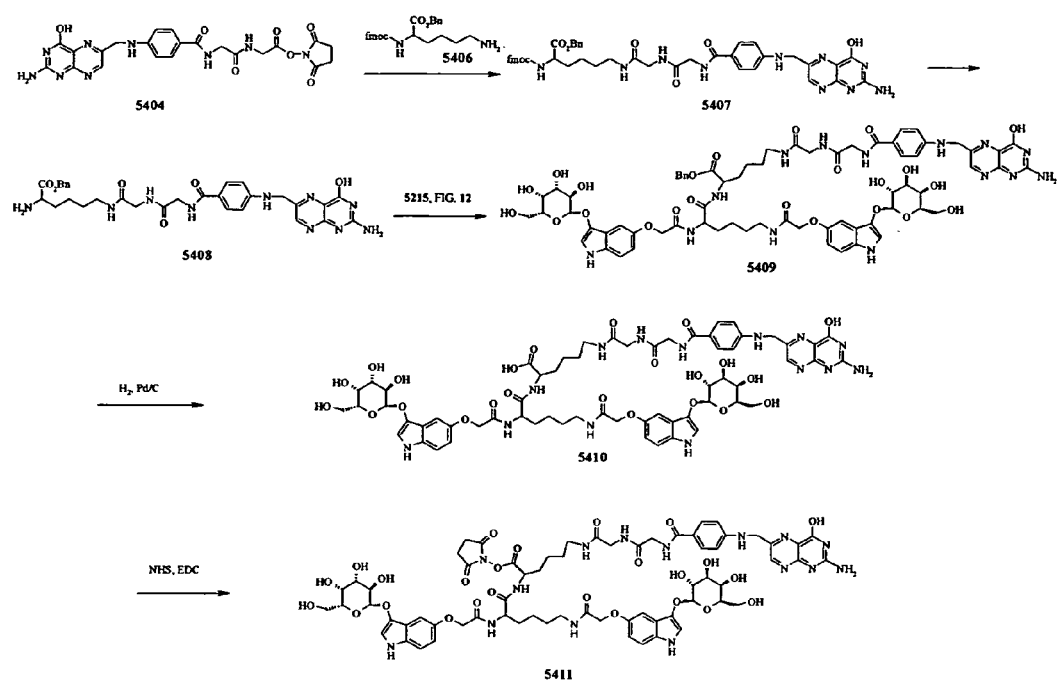
FIG. 21 is an illustration depicting the synthesis of platform building material with cell targeting agent and position for the irreversible enzyme inhibitor for the fourth example of a Step 1 Reagent.
Figure 22:
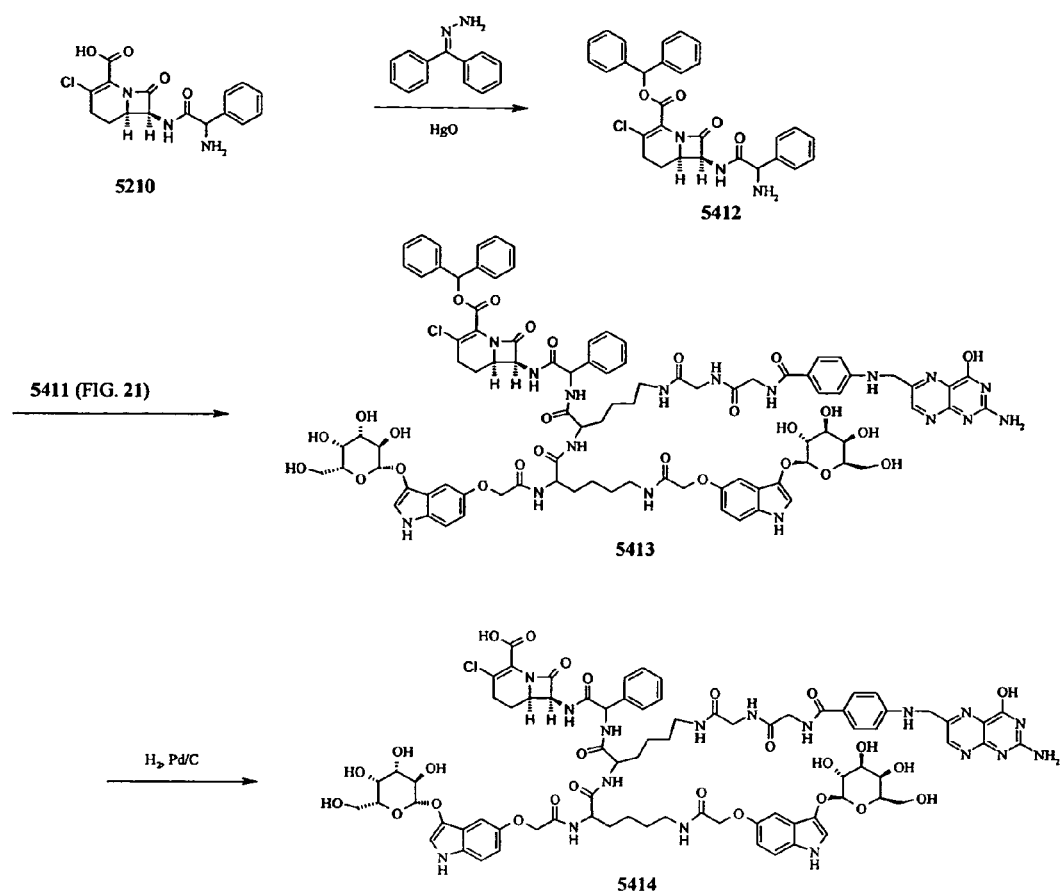
FIG. 22 is an illustration depicting synthesis of the Step 1 Reagent for the fourth example of a Step 1 Reagent.

As shown in FIG. 19, the Step 1 Reagent forms the intracellular aqueous insoluble nano-platform 1540 by linking aggregates of polyindigo to form micro-precipitates. The platform building material is bisindoxylgalactosyl-L-lysine. Some or all of the platform building materials include the additional molecular structure 1440, a Loracarbef-L-lysyl group, which is an irreversible inhibitor of a mutant β-lactamase that is the targeting moiety of the Step 3 Bispecific Reagent. In this fourth example of a Step 1 Reagent there is no carrier moiety, and the cell targeting agent 1140 is a folic acid derivative that is attached directly to the platform building material. Maintenance of reasonable plasma levels of folic acid conjugates for 4 hours can deliver approximately 70 million conjugate molecules per cell into cancer cells 100 expressing fewer than one million receptors per cell (Reddy and Low, Crit. Rev. Therapeut. Drug Deliver. Sys. 15: 587-627, 1998), which shows that there is rapid turnover of the folic acid receptors 101 (FIG. 1).

The synthesis of the Step 1 Reagent proceeds in the following manner: As shown in FIG. 20, the bisindoxylgalactosyl-L-lysine 5207, is prepared as described supra and dissolved in dimethyl sulfoxide and converted to the active ester 5215 using N-hydroxysuccinimide and 1-ethyl-3-[3-(dimethylamino)propyl]carbodiimide. The active ester 5215 reacts with excess ethylenediamine to produce the amino derivative 5401. Pteroic acid 5402 can have its carboxyl group converted to an active ester using N-hydroxysuccinimide and dicyclohexylcarbodiimide, which is followed by the addition of the benzyl ester of glycylglycine to yield the glycylglycyl adduct 5403. Removal of the benzyl protecting group by catalytic hydrogenation with 10% palladium on charcoal and hydrogen is followed by converting the carboxyl group to an active ester 5404 with N-hydroxysuccinimide and 1-ethyl-3-[3-(dimethylamino)propyl]carbodiimide. The active ester 5404 can then react with 5401 to yield the bisindoxylgalactosyl derivative 5405 with the pteroyl targeting agent attached for targeting folate receptors on tumor cells.

FIG. 21 depicts the synthesis to prepare the bisindoxylgalactosyl platform building materials with the additional molecular structure Loracarbef attached. Nα-FMOC-O-benzyl-L-lysine 5406 reacts with pteroyl-glycyl-glycine N-hydroxysuccinimide ester 5404 to yield 5407. The FMOC protecting group is removed from 5407 with base to yield 5408, which has a free amino side chain that can react with the bisindoxylgalactosyl-L-lysine N-hydroxysuccinimide ester 5215 (FIG. 20) to yield the L-lysyl-L-lysyl-glycyl-glycyl derivative 5409. The benzyl-protecting group is removed by catalytic hydrogenation using 10% palladium on charcoal and hydrogen at atmospheric pressure to yield 5410. The carboxyl group on 5410 is then converted to the active ester 5411 using N-hydroxysuccinimide and 1-ethyl-3-[3-(dimethylamino)propyl]carbodiimide.

As shown in FIG. 22, the carboxyl group on Loracarbef 5210 is protected with a benzhydryl group using biphenyldiazomethane (which had been generated from benzylphenone hydrazine and mercuric oxide) to yield 5412. The carboxyl protected Loracarbef 5412 reacts with the active ester (5411, FIG. 21) to yield 5413. Removal of the benzhydryl group by catalytic hydrogenation using 10% palladium on charcoal and hydrogen yields the pteroyl-targeted platform building material with Loracarbef (as the additional molecular structure) 5414. Infusion of a mixture of 5405 (FIG. 20) and 5414 (FIG. 22) allows the folate receptors to internalize the two derivatives in large amounts in the tumor cells (Reddy and Low, Crit. Rev. Therapeut. Drug Deliver. Sys. 15: 587-627, 1998), and inside the cells the galactosyl groups are hydrolyzed by enzymes and the resulting indoxyls dimerize to form indigo derivatives. Thus the bisindoxylgalactosyl platform building materials results in a polyindigo intracellular aqueous insoluble nano-platform on which Loracarbef side chains are attached as additional molecular structures for binding of the Step 3 Bispecific Reagent, a Loracarbef side chain being incorporated whenever one of the platform building materials generated from 5414 is incorporated into the growing polymer.

Example 5

Synthesis of an EGF-HPMA-Indoxyl Galactoside Loracarbef Conjugate

Figure 23:
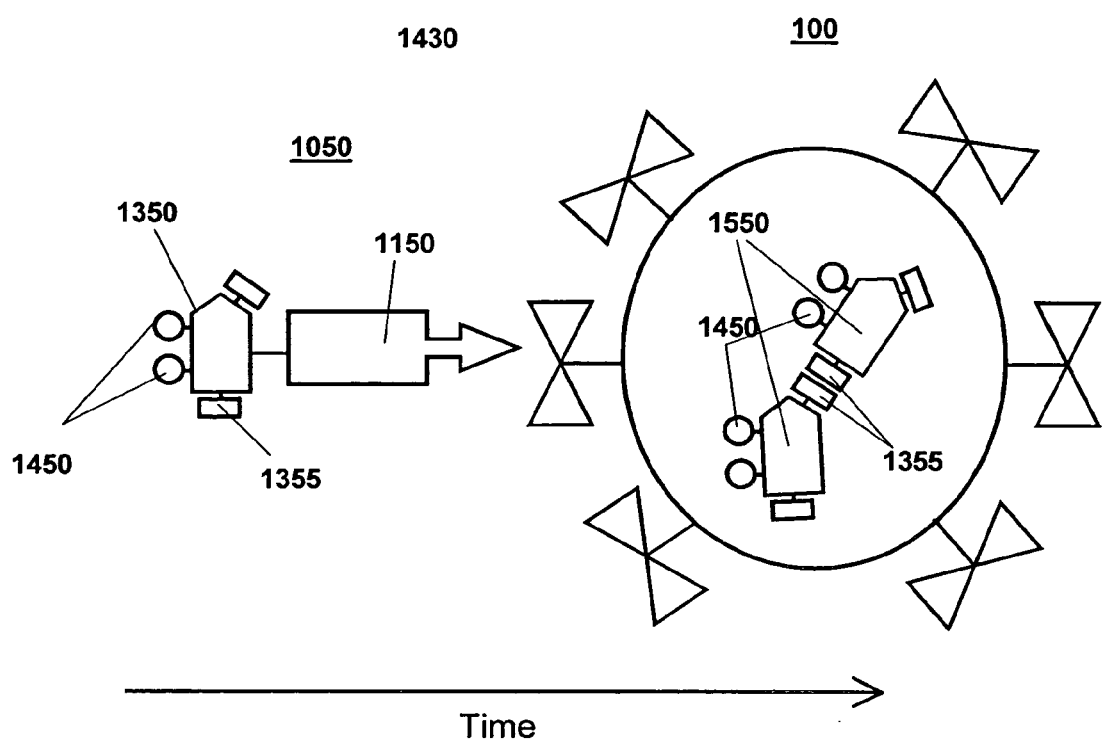
FIG. 23 is an illustration depicting the Step 1 Reagent for the fifth example of a Step 1 Reagent.

A Step 1 Reagent is shown in FIG. 23. The Step 1 Reagent 1050 is comprised of a cell targeting agent 1150, which is an epidermal growth factor (EGF), and a platform building material 1350, which is a synthetic polymer of HPMA that has attached to its surface substituted indoxyl galactoside derivatives 1355, and also has on its surface additional molecular structures 1450 that are the carbacephem analog, Loracarbef, which is an irreversible inhibitor for a mutant β-lactamase. As shown in FIG. 23, the Step 1 Reagent is internalized into the targeted cells 100, and the indoxyl substituents 1355 on the surface of the HPMA platform building materials 1350 form indigos and thereby cross-link the HPMA platform building materials to form the intracellular aqueous insoluble nano-platform 1550.

The Step 1 Reagent forms the intracellular aqueous insoluble nano-platform by cross-linking N-(2-hydroxypropyl)methacrylamide (HPMA) polymers that are the platform building materials, using indigo groups formed by dimerization of indoxyl side chains attached to the surface of the HPMA. The HPMA platform building materials include the additional molecular structure, a derivative of Loracarbef, which is an irreversible inhibitor of a mutant β-lactamase that is the targeting moiety of the Step 3 Bispecific Reagent. The Loracarbefs are attached to the surface of the HPMA as separate side chains from the indoxyl galactoside side chains attached to the surface of the HPMA. The HPMA polymer with attached indoxyl galactoside side chains and attached Loracarbef side chains is targeted by attaching the cell targeting agent epidermal growth factor (EGF), yielding the complete Step 1 Reagent.

Figure 24:
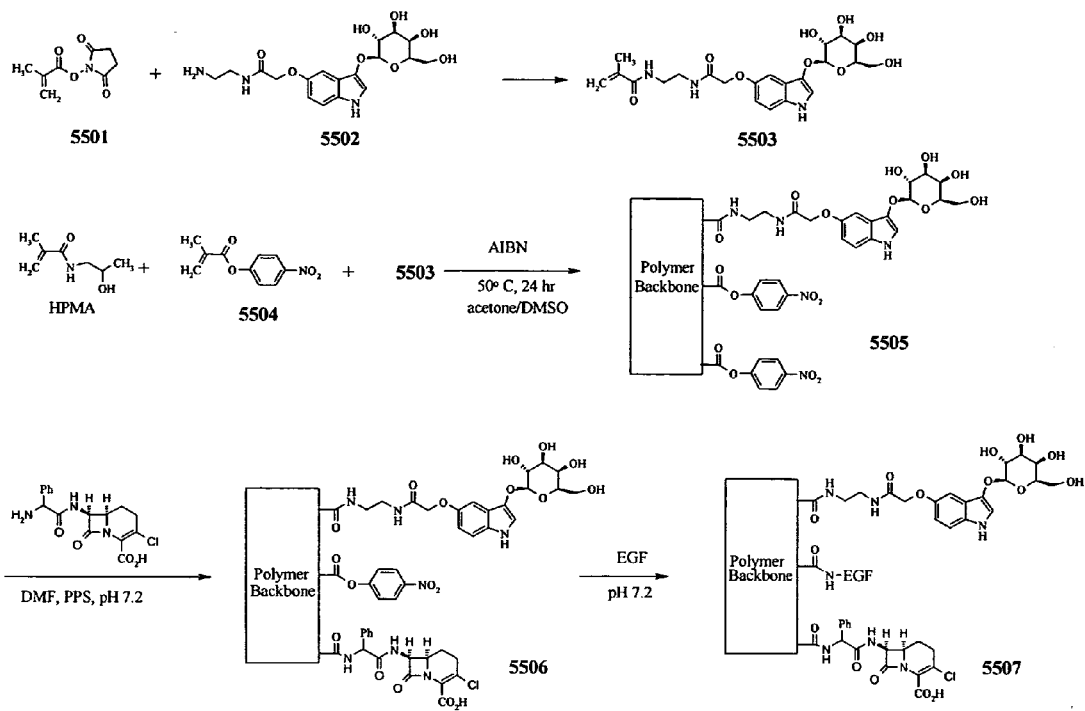
FIG. 24 is an illustration depicting the synthesis of the Step 1 Reagent for the fifth example of a Step 1 Reagent.

As shown in FIG. 24, the HPMA polymers are prepared by co-polymerization of monomer units containing indoxyl galactoside 5503 and monomer units that are p-nitrophenyl esters of acrylic acid 5504. For the acrylic acid-indoxyl galactoside monomer units, acrylic acid is converted into the N-hydroxysuccinimide ester 5501 with dicyclohexylcarbodiimide and allowed to react with the ethylenediamine derivative of 2-(3-β-D-galactosidoxy-indol-5-oxy)acetic acid 5502 to yield the indoxyl galactoside acrylate monomer units 5503. Acrylic acid is converted to the acrylic acid-p-nitrophenyl ester 5504 monomer units using p-nitrophenol and dicyclohexylcarbodiimide. The polymer precursor containing the indoxyl galactosides and the reactive p-nitrophenyl ester groups is prepared as described by Kopecek and his colleagues (Omelyanenko, et al., J. Control. Rel. 52: 25-37, 1998) by co-polymerization of 10 mol % acrylic acid-indoxyl galactoside monomer units 5503, 20 mol % acrylic acid p-nitrophenyl ester monomer units 5504, and N-(2-hydroxypropyl)methacrylamide (HPMA) in acetone/dimethyl sulfoxide at 50° C. for 24 hours using 2,2'-azobisisobutyronitrile (AIBN) as an initiator to yield the polymer intermediate 5505. Loracarbef reacts with some of the p-nitrophenyl ester groups in the polymer intermediate 5505 to yield 5506. The remaining p-nitrophenyl esters on 5506 react with EGF to yield the EGF-targeted polymer with Loracarbef additional molecular structures 5507.

Example 6

Synthesis of a UDP-N-Acetylglucosamine Enolpyruvoyltransferase-Streptavidin Conjugate The targeting moiety of the Step 3 Bispecific Reagent is the enzyme UDP-N-acetylglucosamine enolpyruvoyltransferase. The isotope trapping moiety is Streptavidin, which binds to a radiolabeled biotin derivative that is the Step 4 Reagent.

Figure 35:
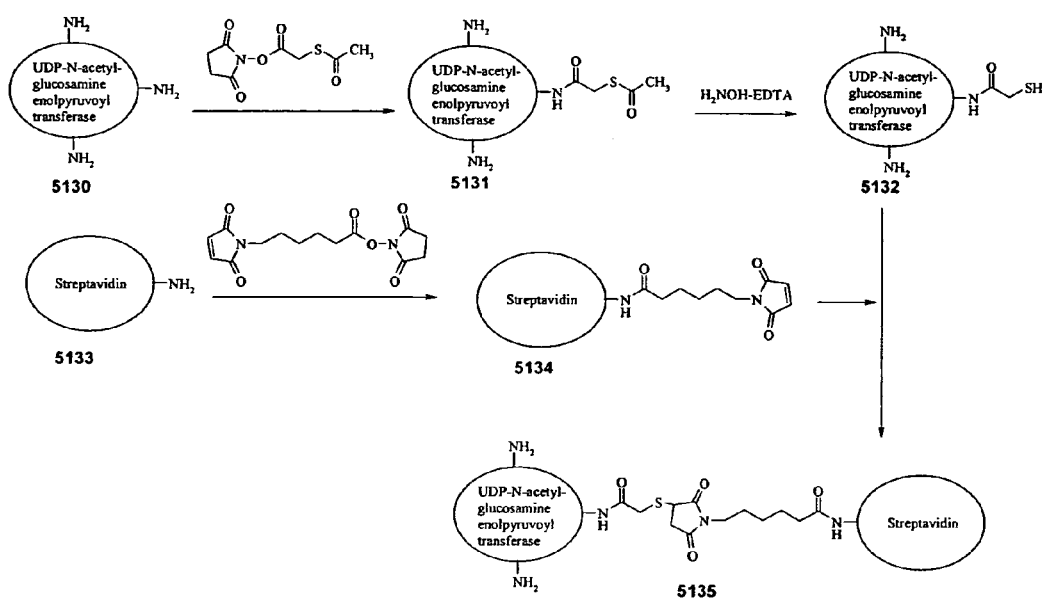
FIG. 35 is an illustration depicting the synthesis of the Step 3 Reagent composed of UDP-N-acetylglucosamine enolpyruvoyltransferase and Streptavidin.

As outlined in FIG. 35, the enzyme UDP-N-acetylglucosamine enolpyruvoyltransferase 5130, which is readily isolated from E. coli Strain JLM16 (Brown, et al., Biochem. 33: 10638-10645, 1994), reacts with the N-hydroxysuccinimide ester of S-acetylthioacetic acid. The thioacetate ester is dissolved in DMSO and added in aliquots to the protein solution in phosphate buffer, pH 7.2, while maintaining the pH between 7 and 7.5 using 0.5N sodium hydroxide. After allowing the reaction to proceed for an hour, the modified protein 5131 is dialyzed against cold phosphate buffer overnight. Streptavidin 5133 is activated with maleimidocaproic acid N-hydroxysulfosuccinimide ester for 30 minutes while maintaining the pH between 7 and 7.5 using 0.5N sodium hydroxide. The modified protein 5134 is separated from reactants by chromatography on a NAP25 column. The S-acetylthioacetate modified UDP-N-acetylglucosamine enolpyruvoyltransferase 5131 is exposed to hydroxylamine for 2 hours to remove the acetyl protecting group to yield 5132, and then the Streptavidin solution 5134 from the column is added to the reaction mixture to allow the proteins to form a conjugate via a thioether linkage. After allowing the proteins to react for 2 hours, the solution is dialyzed overnight against cold phosphate buffered saline, pH 7.2. The conjugate is passed through a Sephacryl S-300 column to separate the conjugates from uncoupled proteins to yield the UDP-N-acetylglucosamine enolpyruvoyltransferase-Streptavidin Step 3 Bispecific Reagent 5135.

Example 7

Synthesis of a Mutant β-Lactamase-β-D-Galactosidase Conjugate

The targeting moiety of the Step 3 Bispecific Reagent is a mutant β-lactamase. Suitable isotope trapping moieties for the Step 3 Bispecific Reagent are outlined in FIG. 26, for example, β-D-galactosidase, which can convert by enzymatic catalytic action the radiolabeled aqueous soluble Step 4 Reagent $^{131}$I-5-iodo-3-indoxylgalactoside into the radiolabeled aqueous insoluble product $^{131}$I-5,5'-diiodoindigo.

The Step 3 Bispecific Reagent was prepared as a fusion protein using recombinant biology. Protein expression vectors were constructed for the production of β-D-galactosidase fusions with the β-lactamase E166A and E166N mutants. The E166A and E166N β-lactamase mutants were constructed using the ung-dut-mutagenesis method (Kunkel, et al., Methods Enzymol. 154: 367-382, 1987) while the E166N mutant was constructed using overlap extension PCR (Ho, et al., Gene 77: 51-59, 1989).

Figure 36:
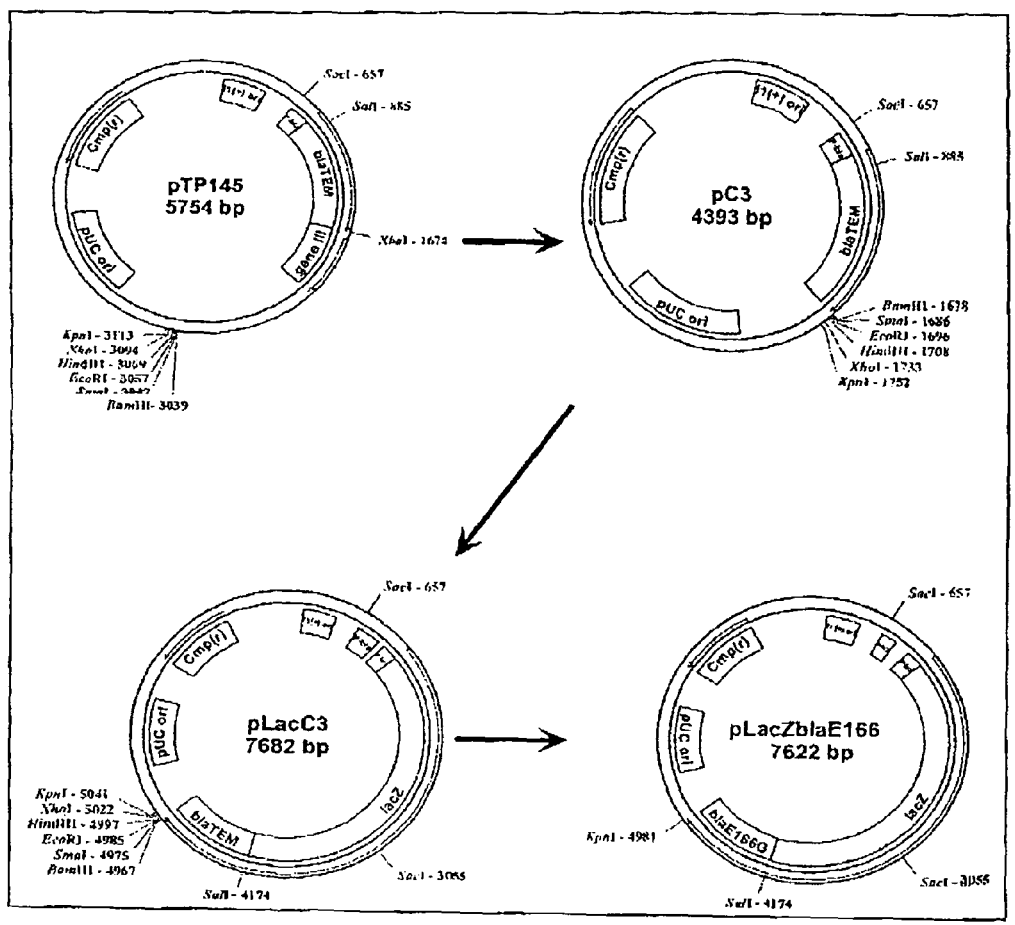
FIG. 36 is an illustration depicting the preparation of plasmid for the β-lactamase mutants.

Two different vectors were used to create fusions of β-D-galactosidase with the β-lactamase mutants. One system was constructed with the phage display plasmid pTP145 (Huang, et al., Gene 251: 187-197, 2000) (FIG. 36). The important feature of this plasmid is that a unique SalI restriction endonuclease site was previously engineered into the β-lactamase gene (bla) downstream of the signal sequence (Huang, et al., J. Mol. Biol. 258: 688-703, 1996). This allows gene fusions to be constructed by insertion genes at the Sal1 site. However, this plasmid is not engineered for protein expression and therefore several additional changes were required. The bacteriophage gene III sequence was removed from pTP145 by restriction endonuclease digestion with BamH1 and Xba1 to release a 1365 base pair (bp) DNA fragment. The 5'-overhangs generated by the enzymes were made blunt ends by treatment with dNTPs and Klenow DNA polymerase. As seen in FIG. 36, the plasmid was recircularized with DNA ligase to create plasmid pC3. The lacZ gene was then amplified by PCR and inserted at the Sal1 site present in the bla gene to create the gene fusion in plasmid pLacC3. The plasmid was introduced into *E. coli* and the presence of the expressed fusion protein in these cells was confirmed by immunoblotting using anti-β-lactamase antibody. Finally, the bla mutations were introduced to create the E166A and E166N substitutions to create the pLacZblaE166 plasmids (FIG. 36). DNA sequencing was performed to ensure the DNA sequence was correct.

Figure 37:
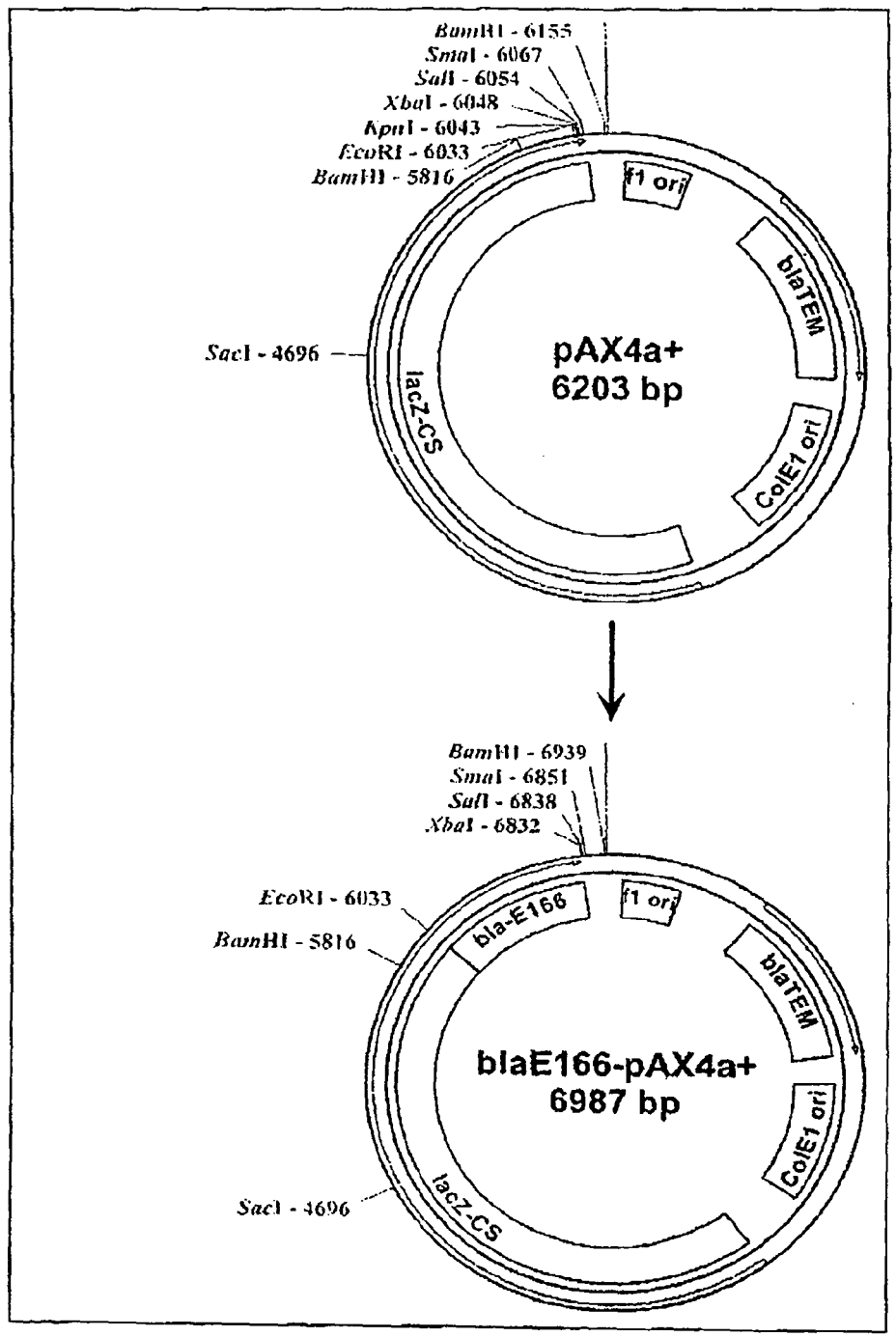
FIG. 37 is an illustration depicting the preparation of the plasmid for the Step 3 Reagent, mutant β-lactamase-β-D-galactosidase.

The second expression system was developed using a commercially available plasmid, pAX4a+ (MoBiTec, Inc.). As seen in FIG. 37, the plasmid was developed specifically to fuse proteins of interest to the lacZ gene. The lacZ gene is fused to a sequence encoding a collagen domain as a spacer between the β-Gal protein and the fused protein of interest. The bla gene encoding the E166N mutant was amplified by PCR and inserted as an EcoRI-XbaI restriction enzyme fragment to create the blaE166-pAX4a+ plasmid. DNA sequencing was performed to ensure the bla gene did not contain other mutations and that the fusion sequence was correct. The plasmid was introduced into *E. coli* and protein expression was verified by immunoblotting using an anti-β-lactamase antibody. Preparative growth of these *E. coli* allowed us to isolate the mutant-β-lactamase-β-D-galactosidase Step 3 Bispecific Reagent via affinity chromatography.

Example 8

Synthesis of Ornithine Decarboxylase Modified with 4-Carboxybenzaldehyde

The targeting moiety of the Step 3 Bispecific Reagent is the enzyme ornithine decarboxylase. The isotope trapping moiety is the small organic molecule, 4-carboxybenzaldehyde, which bears a reactive organic functional group, an aldehyde group, which can covalently bind a radiolabeled aqueous soluble Step 4 Reagent that is a hydrazide derivative, by the formation of a hydrazone.

Figure 38:
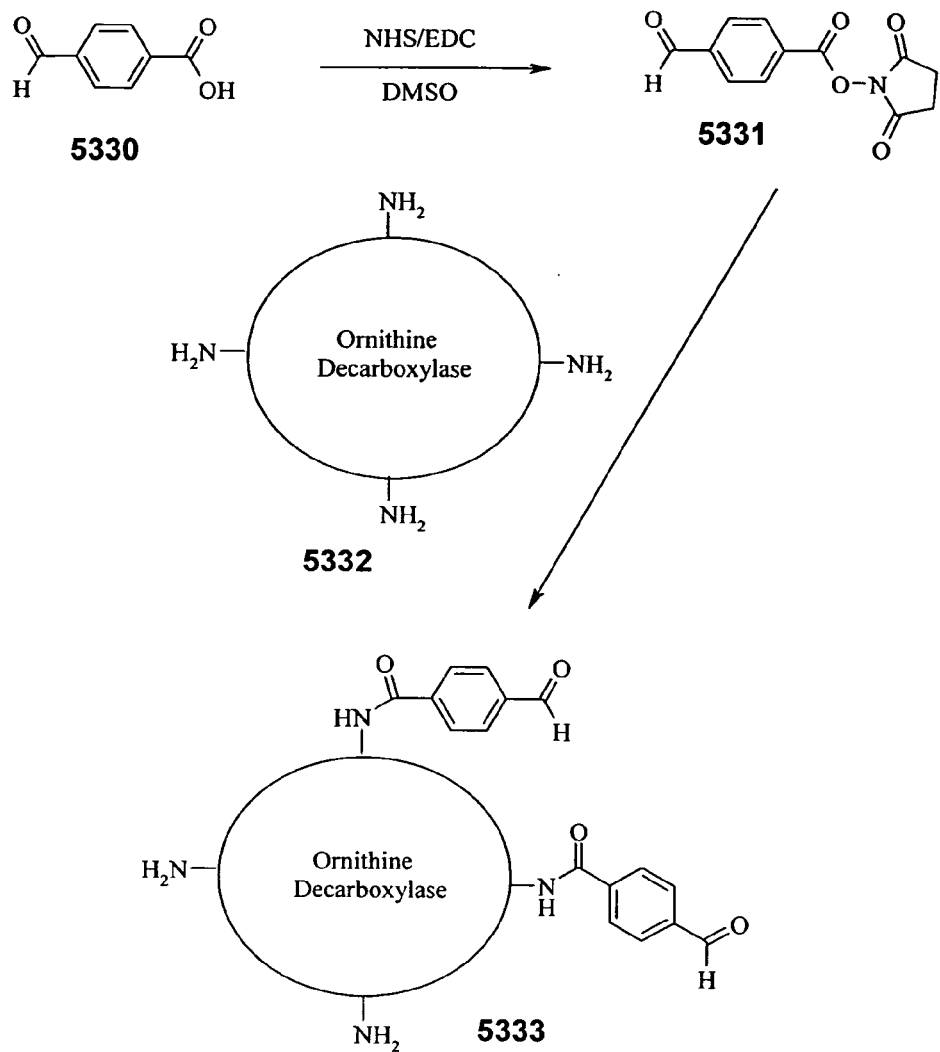
FIG. 38 is an illustration depicting the preparation of Step 3 Bispecific Reagent, ornithine decarboxylase with aldehyde sidechains (i.e. ornithine decarboxylase-4carboxybenzaldehyde).

The preparation of the Step 3 Bispecific Reagent (FIG. 38) involves the addition of a small organic molecule, 4-carboxybenzaldehyde 5330, which bears a reactive organic functional group, an aldehyde group, as the isotope trapping moiety of the Step 3 Bispecific Reagent, to some of the amino acid residues on the enzyme ornithine decarboxylase 5332, the targeting moiety of the Step 3 Bispecific Reagent, without affecting the enzymatic activity of the enzyme. Terephthalaldehydic acid (4-carboxybenzaldehyde 5330) is dissolved in dimethylsulfoxide and activated with N-hydroxysuccinimide and 1-ethyl-3-[3-(dimethylamino)propyl]carbodiimide for 2 hours to yield 5331. Ornithine decarboxylase is dissolved in phosphate buffer, pH 7.2, and the reaction mixture containing activated 4-carboxybenzaldehyde 5331 is added in 100 μL portions while maintaining the pH of the reaction between 7 and 7.5 with 1N sodium hydroxide. Following the reaction, the protein solution is dialyzed at 4° C. in phosphate buffered saline, pH 6.5, to remove low molecular weight reagents.

Example 9

Synthesis of Mutant β-Lactamase-Anti-NIP Antibody Conjugate

The targeting moiety of the Step 3 Bispecific Reagent is a mutant β-lactamase. The isotope trapping moiety is an anti-NIP monoclonal antibody, which can bind a radiolabeled aqueous soluble Step 4 Reagent that contains the haptenic structure $^{131}$I-6-nitro-2-iodophenol ($^{131}$I-NIP), which is recognized by the binding site of the anti-NIP monoclonal antibody.

Figure 39:
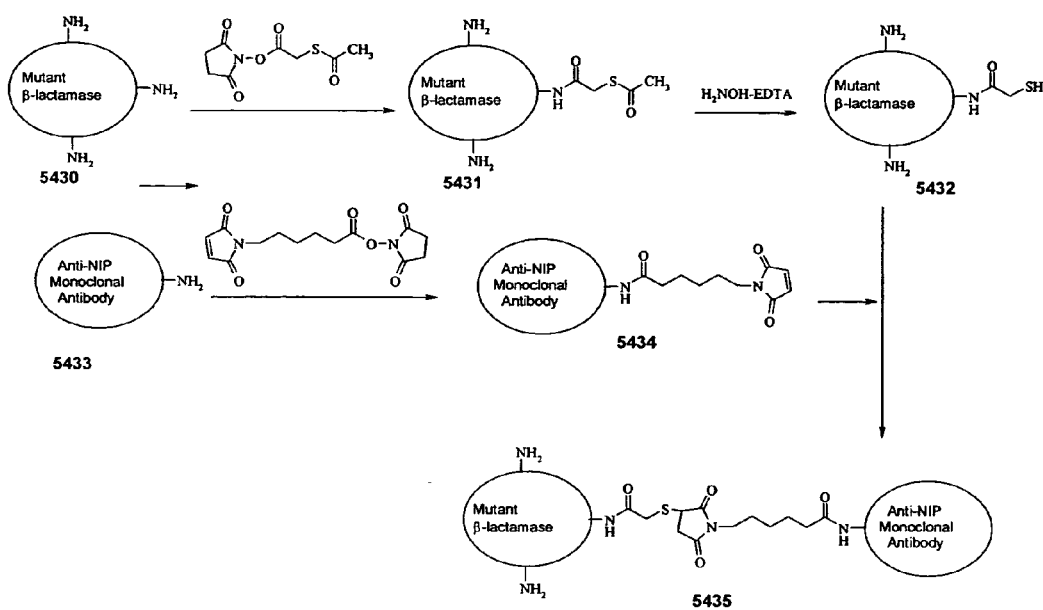
FIG. 39 is an illustration depicting the preparation of Step 3 Bispecific Reagent, mutant β-lactamase-anti-NIP antibody.

Suitable monoclonal antibodies to such a structure as NIP are readily prepared by state-of-the-art monoclonal antibody technologies. Procedures have been developed to prepare the genes corresponding to single chain binding regions from such antibodies and use them with the mutant β-lactamase gene in the production of fusion proteins as discussed above Example 7. Technologies have also been developed that can use the high affinity binding sites developed in murine antibodies to prepare humanized antibodies and reduce immunological responses to such proteins used in therapy. In addition, methods have been worked out to isolate human antibodies with high specificity for a particular antigen, using array technologies. Therefore, there are numerous ways to generate appropriate antibodies for use in Step 3 Bispecific Reagents. As shown in FIG. 39, experience has shown that anti-NIP monoclonal antibody 5433 can react with maleimidocaproic acid N-hydroxysulfosuccinimide ester while maintaining the pH between 7 and 7.5 with 0.5N sodium hydroxide for 30 minutes. The modified protein 5434 is separated from the reagents by passing it through a NAP25 column. A solution of N-hydroxysuccinimidyl S-acetylthioacetate in DMSO is added in aliquots to a solution of the mutant β-lactamase 5430 in phosphate buffer, pH 7.2, while maintaining the pH between 7 and 7.5 with 0.5N sodium hydroxide. The protein solution 5431 is dialyzed against phosphate buffer, pH 7.2, at 4° C. A solution of hydroxylamine is added to the lactamase solution 5431 and allowed to react for 2 hours to remove the acetyl protecting groups to yield 5432, then the maleimidyl modified anti-NIP antibody solution 5434 is added and the two proteins allowed to react for 2 hours. The solution is dialyzed overnight against cold phosphate buffer, pH 7.2, at 4° C. The lactamase-antibody conjugate 5435 is separated from the monomer proteins using Sephacryl S-300 chromatography to yield the mutant β-lactamase-anti-NIP antibody Step 3 Bispecific Reagent 5435.

Example 10

Synthesis of Mutant β-Lactamase-Alkaline Phosphatase Conjugate

The targeting moiety of the Step 3 Bispecific Reagent is a mutant β-lactamase. The isotope trapping moiety of the Step 3 Bispecific Reagent is the enzyme alkaline phosphatase, which will, by enzymatic catalytic action, convert the radiolabeled aqueous soluble Step 4 Reagent $^{131}$I-5-iodo-3-indoxylphosphate into the radiolabeled aqueous insoluble product $^{131}$I-5,5'-diiodoindigo.

Figure 40:
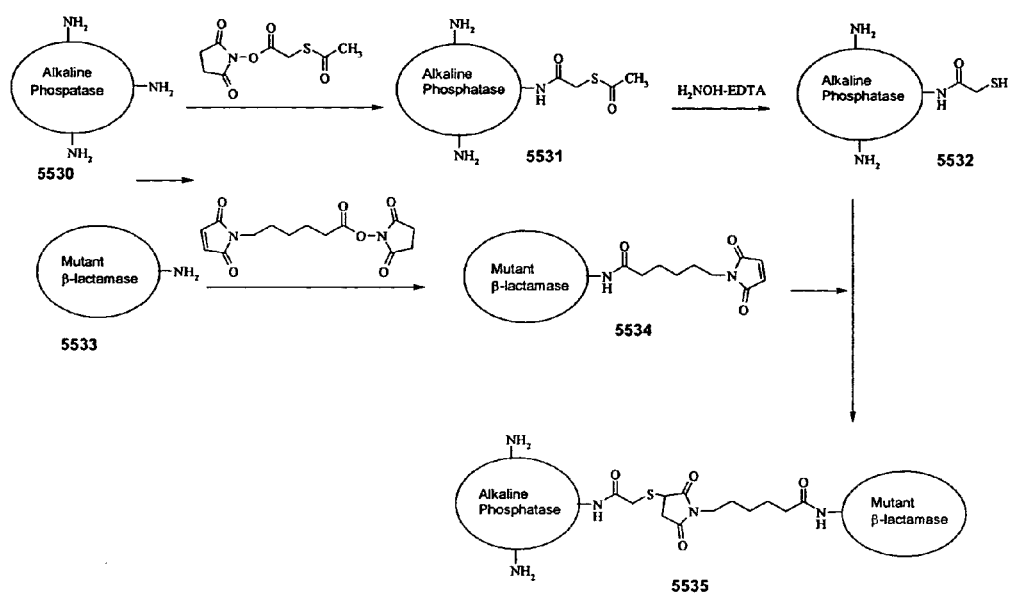
FIG. 40 is an illustration depicting the preparation of Step 3 Bispecific Reagent, mutant β-lactamase-alkaline phosphatase.

As shown in FIG. 40, a mutant β-lactamase 5533 reacts with maleimidocaproic acid N-hydroxysulfosuccinimide ester while maintaining the pH between 7 and 7.5 with 0.5N sodium hydroxide for 30 minutes. The modified protein 5534 is separated from the reagents by passing it through a NAP25 column. A solution of N-hydroxysuccinimidyl S-acetylthioacetate in DMSO is added in aliquots to a solution of alkaline phosphatase 5530 in phosphate buffer, pH 7.2, while maintaining the pH between 7 and 7.5 with 0.5N sodium hydroxide. The protein solution 5531 is dialyzed against phosphate buffer, pH 7.2, at 4° C. A solution of hydroxylamine is added to the alkaline phosphatase solution 5531 and allowed to react for 2 hours to remove the acetyl protecting groups to yield 5532, then the maleimidyl modified mutant β-lactamase solution 5534 is added and the two proteins allowed to react for 2 hours. The solution is dialyzed overnight against cold phosphate buffer, pH 7.2, at 4° C. The lactamase-alkaline phosphatase conjugate 5535 is separated from the monomer proteins using Sephacryl S-300 to yield mutant β-lactamase-alkaline phosphatase, the Step 3 Bispecific Reagent 5535.

Example 11

Synthesis of $^{90}$Y-Biotin-Pentyl-DOTA

Figure 41:
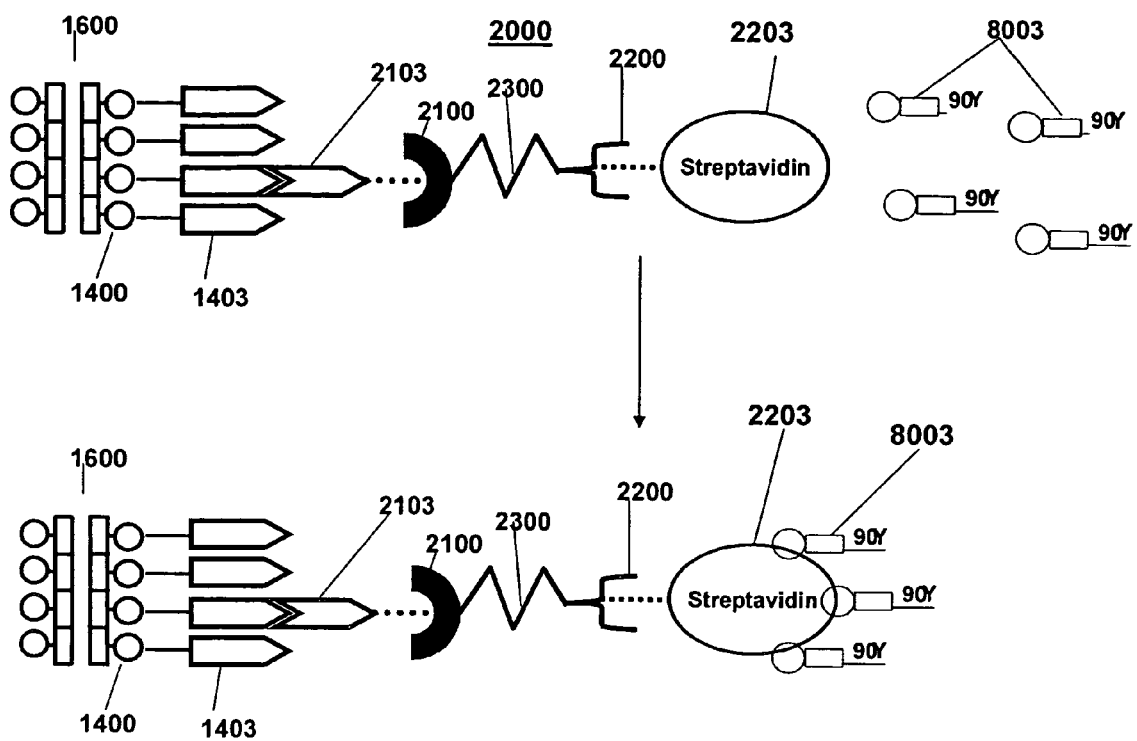
FIG. 41 is an illustration depicting the preparation of first example of a Step 4 Reagent.

The synthesis of a radiolabeled aqueous soluble Step 4 Reagent is outlined in FIG. 41. Previously, the anti-EGF-antibody-dextran-3-indoxyl phosphate-phosphoenol pyruvate Step 1 Reagent was used to build an intracellular nano-platform composed of aggregates of indigo with phosphoenol pyruvate derivatives 1413 on their surfaces as the additional molecular structures 1400. This intracellular nano-platform was relocated into the cancer extracellular space by the action of a Step 2 cell-killing Reagent and/or natural cancer cell-killing to form the extracellular nano-platform 1600. Administration of the Step 3 Bispecific Reagent 2010, a UDP-N-acetylglucosamine enolpyruvoyltransferase 2113-Streptavidin 2213 conjugate, allowed it to become covalently attached to the extracellular nano-platform by the covalent binding of the UDP-N-acetylglucosamine enolpyruvoyltransferase targeting moiety 2113 to its irreversible enzyme inhibitor phosphoenol pyruvate derivative 1413 as the additional molecular structure 1400 on the extracellular nano-platform 1600, thereby attaching the Streptavidin isotope trapping moiety 2213 to the extracellular nano-platform 1600. Administration of the radiolabeled aqueous soluble Step 4 Reagent $^{90}$Y-biotin-pentyl-DOTA 8003 allows it to become bound with very high affinity through the binding of the biotin moieties to several of the four binding sites on the Streptavidin isotope trapping moiety 2213 that is attached to the extracellular nano-platform 1600, thus trapping the radiolabeled aqueous soluble Step 4 Reagent $^{90}$Y radioisotopes within the tumor extracellular matrix for the required period of time to create micro-regional radiation fields (Hot-Spots) to deliver lethal irradiation to the surrounding tumor cells.

Figure 42:
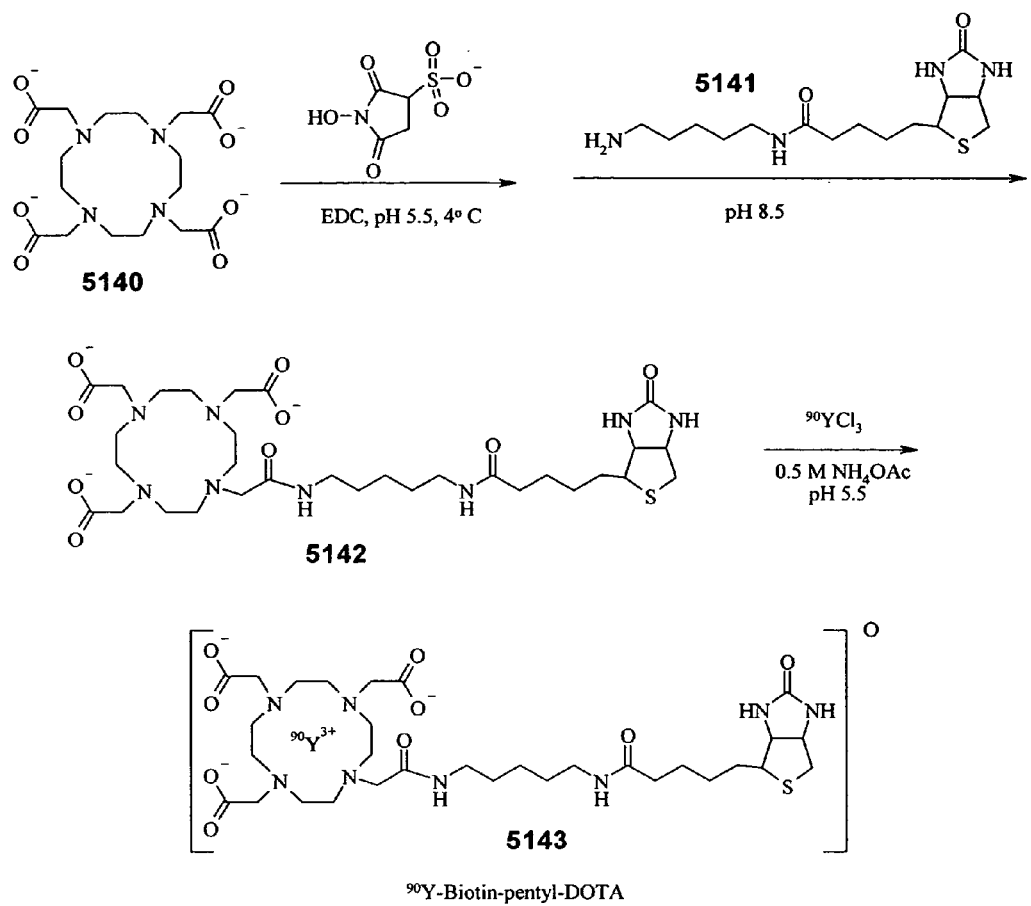
FIG. 42 is an illustration depicting the preparation of $^{90}$Y-biotin-pentyl-DOTA to be used as a Step 4 Reagent.

The synthesis of $^{90}$Y-biotin-pentyl-DOTA 5143, is outlined in FIG. 42. One of the carboxyl groups on DOTA 5140 (1,4,7,10-tetraazacyclododecane-N,N',N'',N'''-tetraacetic acid) is activated as the N-hydroxysulfosuccinimide ester (Lewis, et al., Bioconjugate Chem. 12: 320-324, 2001), which can react with N-(5-aminopentyl)biotinamide 5141 to yield biotin-pentyl-DOTA 5142 (Karacay, et al., Bioconjugate Chem. 8: 585-594, 1997). Exposure to $^{90}$YCl$_3$ allows the molecule to be loaded with the $^{90}$Y radioisotope as a tightly bound chelate to yield the radiolabeled aqueous soluble Step 4 Reagent $^{90}$Y-biotin-pentyl-DOTA 5143.

Example 12

Synthesis of $^{131}$I-5-Iodo-3-Indoxyl Galactoside

The synthesis of a radiolabeled aqueous soluble Step 4 Reagent is outlined in FIG. 43. Previously, the transferrin-human serum albumin-bis-3-indoxyl glycoside-Loracarbef Step 1 Reagent was used to build an intracellular nano-platform composed of aggregates of polyindigo with Loracarbef groups on their surfaces as the additional molecular structures. This intracellular nano-platform was relocated into the cancer extracellular space by the action of a Step 2 cell-killing Reagent and/or natural cancer cell-killing to form the extracellular nano-platform 1600. Administration of the Step 3 Bispecific Reagent mutant β-lactamase-β-D-galactosidase 2020 allowed it to become covalently attached to the extracellular nano-platform through the covalent binding of the mutant β-lactamase targeting moiety 2123 to its irreversible inhibitor Loracarbef 1423 as the additional molecular structure 1400 on the extracellular nano-platform 1600, thus attaching the β-D-galactosidase isotope trapping moiety 2224 to the extracellular nano-platform 1600. Administration of the radiolabeled aqueous soluble Step 4 Reagent $^{131}$I-5-iodo-3-indoxyl galactoside 8004 allows it to come in contact with the β-D-galactosidase isotope trapping moiety 2224 that is attached to the extracellular nano-platform 1600, and the catalytic action of the β-D-galactosidase isotope trapping moiety 2224 cleaves the galactosidyl groups from the radiolabeled aqueous soluble Step 4 Reagent $^{131}$I-5-iodo-3-indoxyl galactoside 8004, releasing the $^{131}$I-5-iodo-3-indoxyls which rapidly undergo oxidative dimerization to form the radiolabeled aqueous insoluble product $^{131}$I-5,5'-diiodoindigo 8005, which becomes trapped within the tumor extracellular matrix for the required period of time to create micro-regional radiation fields (Hot-Spots) to deliver lethal irradiation to the surrounding tumor cells.

Figure 44:
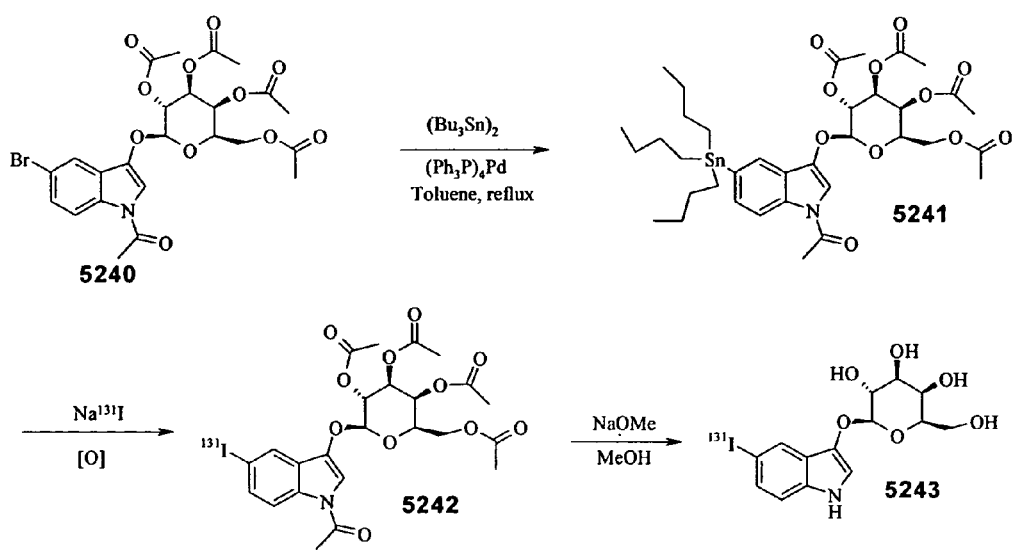
FIG. 44 is an illustration depicting the preparation of $^{131}$I-5-Iodo-3-indoxyl galactoside to be used as a Step 4 Reagent.

The synthesis of $^{131}$I-5-iodo-3-indoxyl galactoside 5243, is outlined in FIG. 44. The acetyl protected 5-bromo-3-indoxyl galactoside 5240 was treated with bis(tributyltin) and palladium tetrakistriphenylphosphine in refluxing toluene to yield the tributyl tin derivative 5241, which was treated with Na$^{131}$I and N-chlorosuccinimide to yield the acetyl protected radiolabeled $^{131}$I-5-iodo-3-indoxyl galactoside 5242. Removal of the acetyl protecting groups with sodium methoxide in methanol yields the radiolabeled aqueous soluble Step 4 Reagent $^{131}$I-5-iodo-3-indoxyl galactoside 5243.

Example 13

Synthesis of $^{131}$I-p-Iodobenzoic Hydrazide

Figure 45:
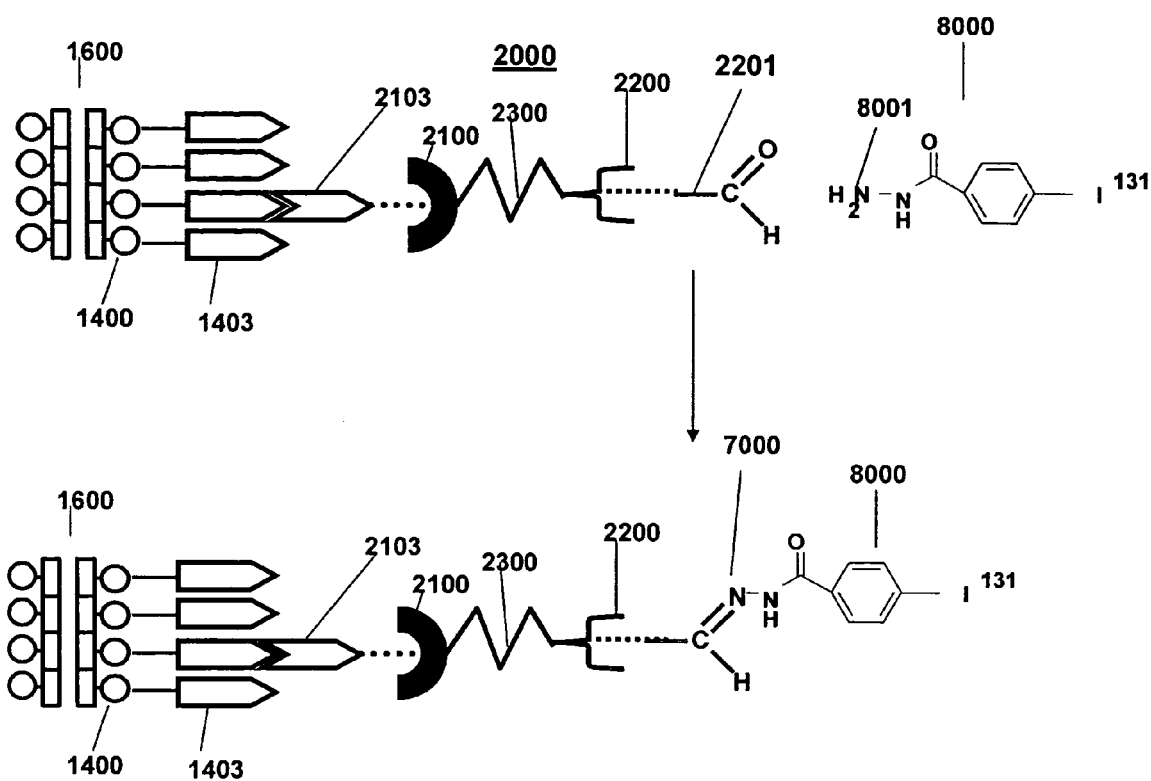
FIG. 45 is an illustration depicting the preparation of third example of a Step 4 Reagent.

The synthesis of a radiolabeled aqueous soluble Step 4 Reagent is outlined in FIG. 45. Previously, the folate—human immunoglobulin—porphyrin-α-difluoromethylornithine Step 1 Reagent was used to build an intracellular nano-platform composed of aggregates of porphyrin derivatives with α-difluoromethylornithine groups on their surfaces as the additional molecular structures. This intracellular nano-platform was subsequently relocated into the cancer extracellular space by the action of a Step 2 cell-killing Reagent and/or natural cancer cell-killing to form the extracellular nano-platform 1600. Administration of the Step 3 Bispecific Reagent 2030 that is ornithine decarboxylase 2133 with attached benzaldehyde groups 2231 allowed it to become covalently attached to the extracellular nano-platform 1600 through the covalent binding of the ornithine decarboxylase targeting moiety 2133 to its irreversible inhibitor α-difluoromethylornithine 1433 as the additional molecular structure 1400 on the extracellular nano-platform 1600, thus attaching the benzaldehyde group isotope trapping moieties 2231 to the extracellular nano-platform 1600. Administration of the radiolabeled aqueous soluble Step 4 Reagent $^{131}$I-p-iodobenzoic hydrazide 8000 allows it to become covalently bound via a hydrazide group 8001 as a hydrazone 7000 to the benzaldehyde group isotope trapping moieties 2231 that are attached to the extracellular aqueous insoluble nano-platform 1600, thus trapping the radiolabeled aqueous soluble Step 4 Reagent radioisotopes within the tumor extracellular matrix for the required period of time to create micro-regional radiation fields (Hot-Spots) to deliver lethal irradiation to the surrounding tumor cells.

Figure 46:
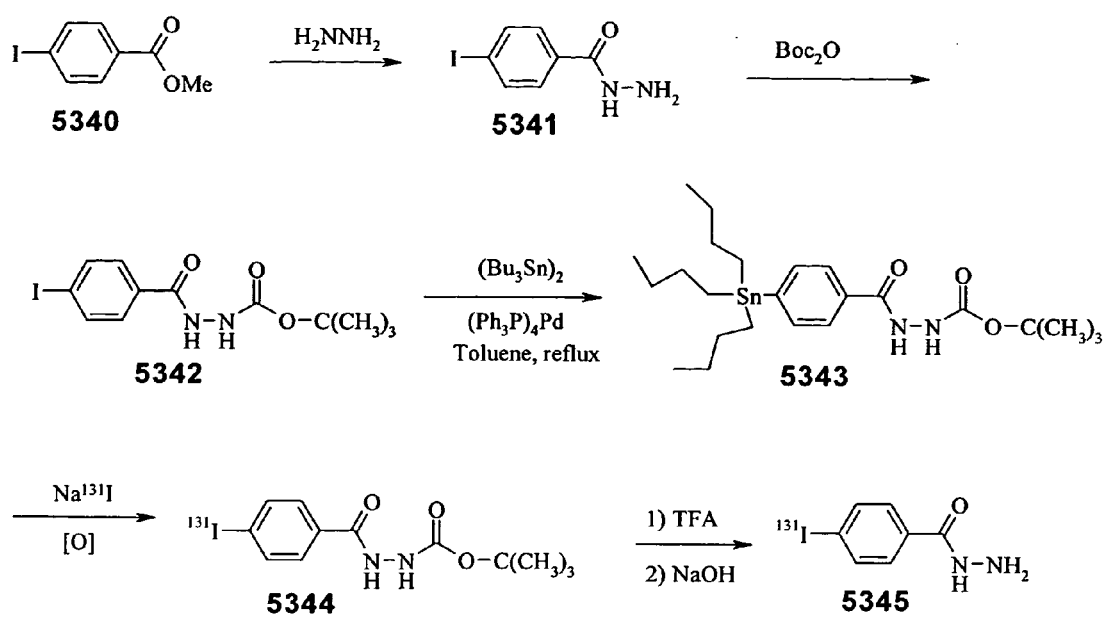
FIG. 46 is an illustration depicting the preparation of $^{131}$I-p-iodobenzoic hydrazide to be used as a Step 4 Reagent.

The synthesis of $^{131}$I-p-iodobenzoic hydrazide 5345, is outlined in FIG. 46. Methyl-p-iodobenzoate 5340 reacts with hydrazine to yield the p-iodobenzoic hydrazide 5341. The hydrazide is then protected as the t-Boc derivative 5342 using di-tert-butyl dicarbonate. The iodo group is displaced using bis(tributyltin) and palladium tetrakistriphenylphosphine in refluxing toluene to yield the tributyl tin derivative 5343, which is treated with Na$^{131}$I and N-chlorosuccinimide to yield the t-Boc protected radiolabeled $^{131}$I-p-iodobenzoic hydrazide 5344. Removal of the t-Boc protecting group with trifluoroacetic acid can yield the radiolabeled aqueous soluble Step 4 Reagent $^{131}$I-p-iodobenzoic hydrazide 5345.

Example 14

Synthesis of $^{131}$I-4-Hydroxy-3-Iodo-5-Nitrophenylacetic Acid

Figure 47:
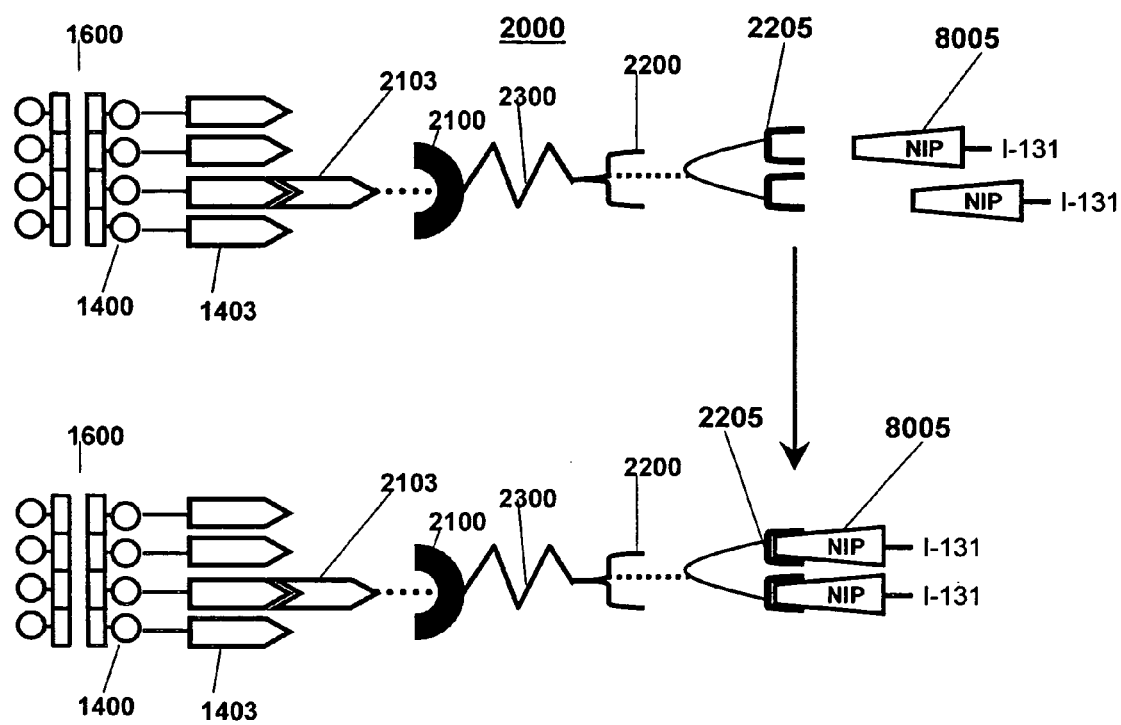
FIG. 47 is an illustration depicting the preparation of fourth example of a Step 4 Reagent.

The synthesis of a radiolabeled aqueous soluble Step 4 Reagent is outlined in FIG. 47. Previously, the folate-bis-3-indoxyl galactoside-Loracarbef Step 1 Reagent was used to build an intracellular nano-platform composed of aggregates of polyindigo with Loracarbef groups on their surfaces as the additional molecular structures. This intracellular nano-platform was subsequently relocated into the cancer extracellular space by the action of a Step 2 cell-killing Reagent and/or natural cancer cell-killing to form the extracellular nano-platform 1600. Administration of the Step 3 Bispecific Reagent 2040 mutant β-lactamase-anti-NIP-antibody allowed it to become covalently attached to the extracellular nano-platform 1600 through the covalent binding of the mutant β-lactamase targeting moiety 2143 to its irreversible inhibitor Loracarbef 1443 as the additional molecular structure 1400 on the extracellular nano-platform 1600, thus attaching the anti-NIP antibody isotope trapping moiety 2245 to the extracellular nano-platform 1600. Administration of the radiolabeled aqueous soluble Step 4 Reagent $^{131}$I-4-hydroxy-3-iodo-5-nitrophenylacetic acid 8005 ($^{131}$I-NIP acid), which is a radiolabeled hapten for the anti-NIP antibody, allows it to bind to the anti-NIP antibody isotope trapping moiety 2245 with high affinity, thus trapping the radiolabeled aqueous soluble Step 4 Reagent radioisotopes within the tumor extracellular matrix for the required period of time to create micro-regional radiation fields (Hot-Spots) to deliver lethal irradiation to the surrounding tumor cells.

Figure 48:
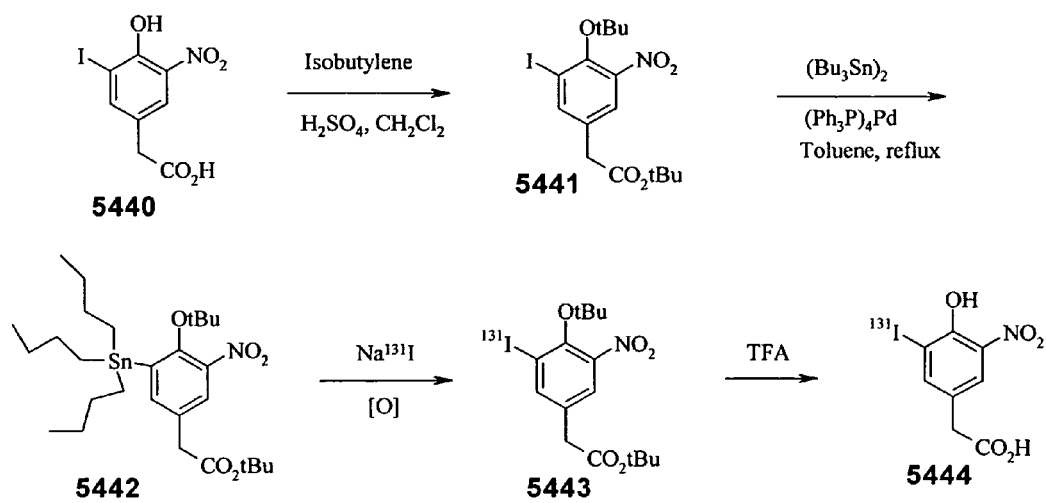
FIG. 48 is an illustration depicting the reparation of $^{131}$I-4-hydroxy-3-iodo-5-nitrophenylacetic acid ($^{131}$I-NIP acid) to be used as a Step 4 Reagent.

The synthesis of $^{131}$I-4-hydroxy-3-iodo-5-nitrophenylacetic acid 5444 ($^{131}$I-NIP acid), is outlined in FIG. 48. It is understood that the carboxyl and phenolic groups on 4-hydroxy-3-iodo-5-nitrophenylacetic acid 5440 (NIP-acid) are protected by attachment of t-butyl groups using isobutylene and sulfuric acid in methylene chloride to yield 5441. The iodo group is displaced using bis(tributyltin) and palladium tetrakistriphenylphosphine in refluxing toluene to yield the tributyl tin derivative 5442, which is treated with Na$^{131}$I and N-chlorosuccinimide to yield the t-butyl protected $^{131}$I-radiolabeled NIP-acid 5443. Removal of the protecting groups with trifluoroacetic acid can yield the radiolabeled aqueous soluble Step 4 Reagent $^{131}$I-4-hydroxy-3-iodo-5-nitrophenylacetic acid ($^{131}$I-NIP acid) 5444.

Example 15

Synthesis of $^{131}$I-5-Iodo-3-Indoxyl Phosphate

Figure 49:
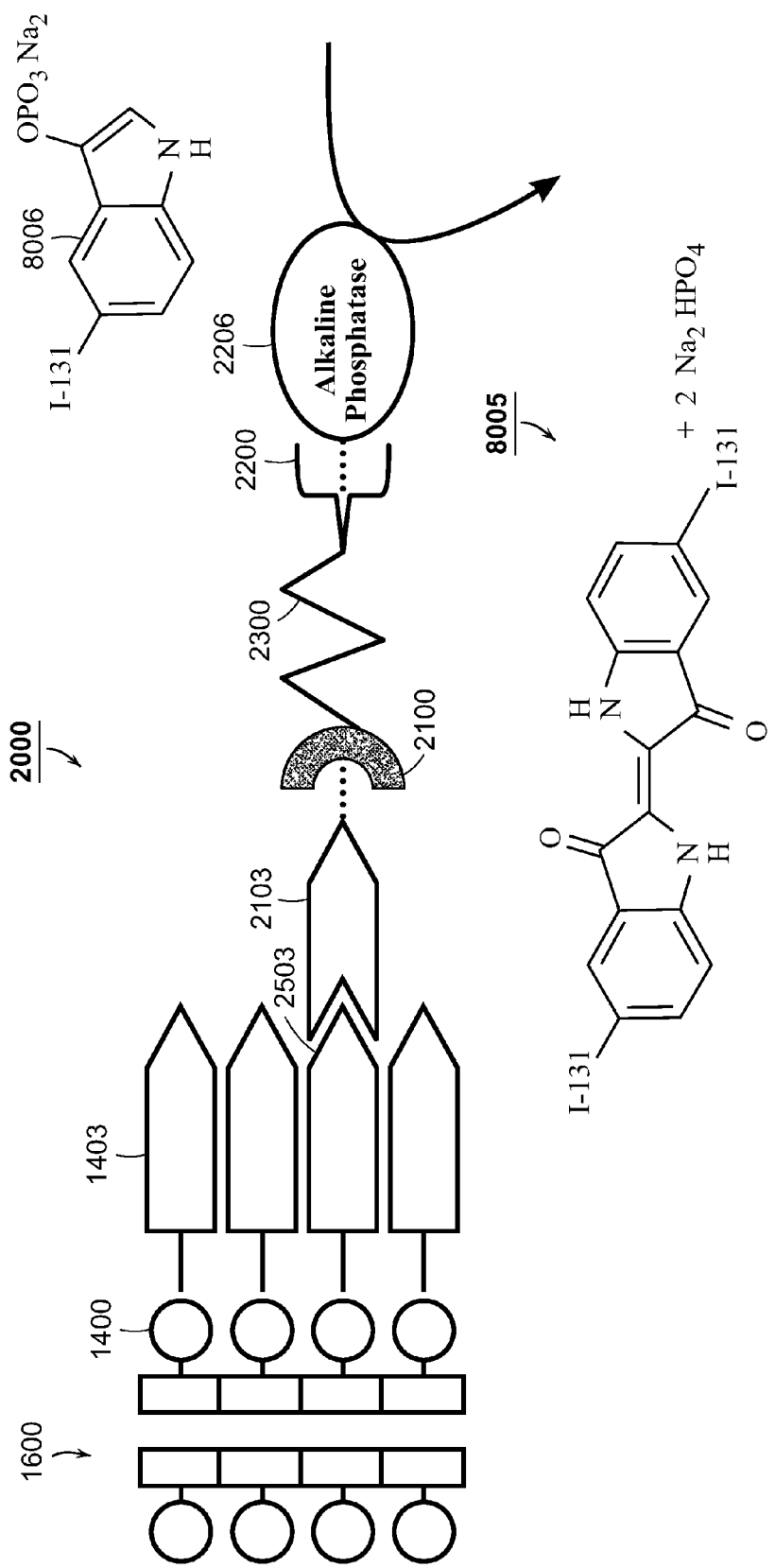
FIG. 49 is an illustration depicting the preparation of fifth example of a Step 4 Reagent.

The synthesis of a radiolabeled aqueous soluble Step 4 Reagent is outlined in FIG. 49. Previously, the EGF-HPMA-3-indoxyl galactoside-Loracarbef Step 1 Reagent was used to build an intracellular nano-platform composed of HPMA polymers cross-linked by indigo groups (like a zipper) with Loracarbef groups on their surfaces as the additional molecular structures. This intracellular nano-platform was subsequently relocated into the cancer extracellular space by the action of a Step 2 cell-killing Reagent and/or natural cancer cell-killing to form the extracellular nano-platform 1600. Administration of the Step 3 Bispecific Reagent 2050 mutant β-lactamase-alkaline phosphatase allowed it to become covalently attached to the extracellular nano-platform 1600 through the covalent binding of the mutant β-lactamase targeting moiety 2153 to its irreversible inhibitor Loracarbef 1453 as the additional molecular structure 1400 on the extracellular nano-platform 1600, thus attaching the alkaline phosphatase isotope trapping moiety 2256 to the extracellular nano-platform 1600. Administration of the radiolabeled aqueous soluble Step 4 Reagent $^{131}$I-5-iodo-3-indoxyl phosphate 8006 allows it to come into contact with the alkaline phosphatase isotope trapping moiety 2256 that is attached to the extracellular aqueous insoluble nano-platform 1600, and the catalytic action of the alkaline phosphatase isotope trapping moiety 2256 cleaves the phosphate groups from the radiolabeled aqueous soluble Step 4 Reagent $^{131}$I-5-iodo-3-indoxyl phosphate 8006, releasing the $^{131}$I-5-iodo-3-indoxyls which rapidly undergo oxidative dimerization to form the radiolabeled aqueous insoluble product $^{131}$I-5,5'-diiodoindigo 8005, which becomes trapped within the tumor extracellular matrix for the required period of time to create micro-regional radiation fields (Hot-Spots) to deliver lethal irradiation to the surrounding tumor cells.

The synthesis of $^{131}$I-5-iodo-3-indoxyl phosphate 5543, is outlined in FIG. 50. The benzyl protected 5-bromo-3-indoxyl phosphate 5540 was treated with bis(tributyltin) and palladium tetrakistriphenylphosphine in refluxing toluene to yield the tributyl tin derivative 5541, which was treated with Na$^{131}$I and N-chlorosuccinimide to yield the benzyl protected radiolabeled $^{131}$I-5-iodo-3-indoxyl phosphate 5542. Removal of the benzyl protecting groups with trifluoroacetic acid yielded the radiolabeled aqueous soluble Step 4 Reagent $^{131}$I-5-iodo-3-indoxyl phosphate 5543.

EQUIVALENTS

From the foregoing detailed description of the specific embodiments of the invention, it should be apparent that unique compositions have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. A method of alleviating a symptom of cancer comprising administering to a subject suffering from said cancer:
   a. a reagent comprising a cell targeting agent which augments cellular uptake of the reagent linked to a platform building material, wherein said platform building material detaches from said cell targeting agent upon uptake of the reagent into the cell and forms an aqueous insoluble nano-platform;
   b. a bi-specific reagent comprising a targeting moiety capable of binding to the aqueous insoluble nano-platform and an isotope trapping moiety; and
   c. a radiolabeled aqueous soluble reagent.

2. The method of claim 1, further comprising administering a cell-killing reagent prior to the administration of (b).

* * * * *